(12) United States Patent
Sell et al.

(10) Patent No.: US 10,695,326 B2
(45) Date of Patent: Jun. 30, 2020

(54) COMPOSITIONS AND METHODS FOR TREATING OR PREVENTING DERMAL DISORDERS

(71) Applicant: DREXEL UNIVERSITY, Philadelphia, PA (US)

(72) Inventors: Christian Sell, Conshohocken, PA (US); Timothy Nacarelli, Norristown, PA (US); Ashley Azar, North Wales, PA (US)

(73) Assignee: Drexel University, Philadelphia, PA (US)

(*) Notice: Subject to any disclaimer, the term of this patent is extended or adjusted under 35 U.S.C. 154(b) by 0 days.

(21) Appl. No.: 15/762,317

(22) PCT Filed: Sep. 19, 2016

(86) PCT No.: PCT/US2016/052442
§ 371 (c)(1),
(2) Date: Mar. 22, 2018

(87) PCT Pub. No.: WO2017/053222
PCT Pub. Date: Mar. 30, 2017

(65) Prior Publication Data
US 2018/0280362 A1 Oct. 4, 2018

Related U.S. Application Data

(60) Provisional application No. 62/232,228, filed on Sep. 24, 2015.

(51) Int. Cl.
| A61K 31/436 | (2006.01) |
| A61P 17/00 | (2006.01) |
| A61K 31/501 | (2006.01) |
| A61K 31/519 | (2006.01) |
| A61K 31/5377 | (2006.01) |

(52) U.S. Cl.
CPC .......... *A61K 31/436* (2013.01); *A61K 31/501* (2013.01); *A61K 31/519* (2013.01); *A61K 31/5377* (2013.01); *A61P 17/00* (2018.01)

(58) Field of Classification Search
CPC .............................. A61K 31/436; A61P 17/00
See application file for complete search history.

(56) References Cited

U.S. PATENT DOCUMENTS

| 5,286,730 A | 2/1994 | Caufield et al. |
| 7,026,374 B2 | 4/2006 | Nathan et al. |
| 7,074,804 B2 | 7/2006 | Zhu et al. |
| 8,946,256 B2 | 2/2015 | Bacus |
| 2004/0180430 A1 | 9/2004 | West et al. |
| 2007/0265294 A1 | 11/2007 | Kleinman et al. |
| 2010/0081681 A1 | 4/2010 | Blagosklonny et al. |
| 2010/0184768 A1 | 7/2010 | Stock et al. |
| 2010/0260733 A1 | 10/2010 | Qi et al. |
| 2011/0150856 A1 | 6/2011 | Bacus et al. |
| 2013/0102572 A1 | 4/2013 | Sugarman et al. |
| 2013/0317053 A1 | 11/2013 | Kaneda et al. |
| 2014/0135330 A1 | 5/2014 | Fairhurst et al. |
| 2014/0377285 A1 | 12/2014 | Liu et al. |
| 2015/0140036 A1* | 5/2015 | Mannick .............. A61K 39/092 424/209.1 |
| 2015/0202187 A1 | 7/2015 | Bacus et al. |
| 2016/0235763 A1* | 8/2016 | Budunova .............. A61K 31/56 |

FOREIGN PATENT DOCUMENTS

| AU | 2013204219 B2 | 5/2015 | |
| EP | 2671583 A1 | 12/2013 | |
| WO | 9924036 A1 | 5/1999 | |
| WO | 2006099390 A1 | 9/2006 | |
| WO | 2008022256 A2 | 2/2008 | |
| WO | WO-2008015539 A2 * | 2/2008 | ........... A61K 9/0014 |
| WO | 2008143928 A1 | 11/2008 | |
| WO | 2009046436 A1 | 4/2009 | |
| WO | 2011079154 A1 | 6/2011 | |

OTHER PUBLICATIONS

Everolimus in Treating Cutaneous T-cell Lymphoma (CTCL). ClinicalTrials.gov Identifier: NCT01637090. Apr. 24, 2016. <https://clinicaltrials.gov/ct2/show/NCT01637090> Accessed Sep. 20, 2016.
International Search Report and Written Opinion for PCT International Application No. PCT/US2016/052442 dated Dec. 16, 2016.
Long-term Trial of Topical Sirolimus to Angiofibroma in Patient With Tuberous Sclerosis Complex. ClinicalTrials.gov Identifier: NCT02634931. Dec. 21, 2015. <https://clinicaltrials.gov/ct2/show/NCT02634931> Accessed Sep. 20, 2016.
Pilot Study of mTOR Inhibitor Therapy in Peutz-Jeghers Syndrome. ClinicalTrials.gov Identifier: NCT00811590. Jul. 19, 2013. <https://clinicaltrials.gov/ct2/show/NCT00811590> Accessed Sep. 20, 2016.
Study of Everolimus in the Treatment of Advanced Malignancies in Patients With Peutz-Jeghers Syndrome (EVAMP). Apr. 21, 2015. ClinicalTrials.gov Identifier: NCT01178151. <https://clinicaltrials.gov/ct2/show/NCT01178151> Accessed Sep. 20, 2016.
Subconjunctival Sirolimus for the Treatment of Autoimmune Active Anterior Uveiti. ClinicalTrials.gov Identifier: NCT00876434. Sep. 26, 2015. <https://clinicaltrials.gov/ct2/show/NCT00876434> Accessed Sep. 20, 2016.
Therapeutic Efficacy of Topical Sirolimus in Early Stage Cutaneous T-cell Lymphoma (CTCL). ClinicalTrials.gov Identifier: NCT01843998. Jun. 3, 2015. <https://clinicaltrials.gov/ct2/show/NCT01843998> Accessed Sep. 20, 2016.

(Continued)

*Primary Examiner* — Sarah Pihonak
*Assistant Examiner* — Jason Deck
(74) *Attorney, Agent, or Firm* — Saul Ewing Arnstein & Lehr LLP; Kathryn Doyle; Domingos J. Silva

(57) ABSTRACT

The present invention includes compositions and methods for treating or preventing certain dermal disorders including dermal atrophy, pseudoscars, actinic keratosis, seborrheic or actinic keratoses, lentigines, focal areas of dermal thickening, and coarse wrinkles. In certain embodiments, the compositions useful within the invention comprise a therapeutically effective amount of a mTORC1 inhibitor and a dermatologically acceptable carrier.

5 Claims, 35 Drawing Sheets

(56) References Cited

OTHER PUBLICATIONS

Topical Sirolimus in Patients With Basal Cell Nevus Syndrome and in Healthy Participants. ClinicalTrials.gov Identifier: NCT00433485. Feb. 14, 2009. <https://clinicaltrials.gov/ct2/show/NCT00433485. Accessed Sep. 20, 2016.

Tuberous Sclerosis Complex: Facial Angiofibroma Skin Cream. ClinicalTrials.gov Identifier: NCT01853423. Aug. 17, 2016. <https://clinicaltrials.gov/ct2/show/NCT01853423> Accessed Sep. 20, 2016.

Phase III Thal of Topical Formulation of Sirolimus to Skin Lesions in Patients With Tuberous Sclerosis Complex (TSC), CinicalTrials. gov Identifier: NCT02635789. Dec. 21, 2015. <https://clinicaltrials.gov/ct2/show/NCT02635789> Accessed Sep. 20, 2016.

Nacarelli, et al., "Inhibition of mTOR Prevents ROS Production Initiated by Ethidium Bromide-Induced Mitochondrial DNA Depletion," Front Endocrinol 5:122 ,Jul. 2014 ,1-8.

Extended European Search Report for European Patent Application No. 16849389.8 dated Mar. 6, 2019.

Bitto, et al., "Long-Term IGF-I Exposure Decreases Autophagy and Cell Viability", PLoS ONE 5(9), Sep. 2010, e12592.

Lerner, et al., "Reduced mammalian target of rapamycin activity facilitates mitochondrial retrograde signaling and increases life span in normal human fibroblasts", Aging Cell (2013) 12, 966-977.

* cited by examiner

Control

NRTI treated

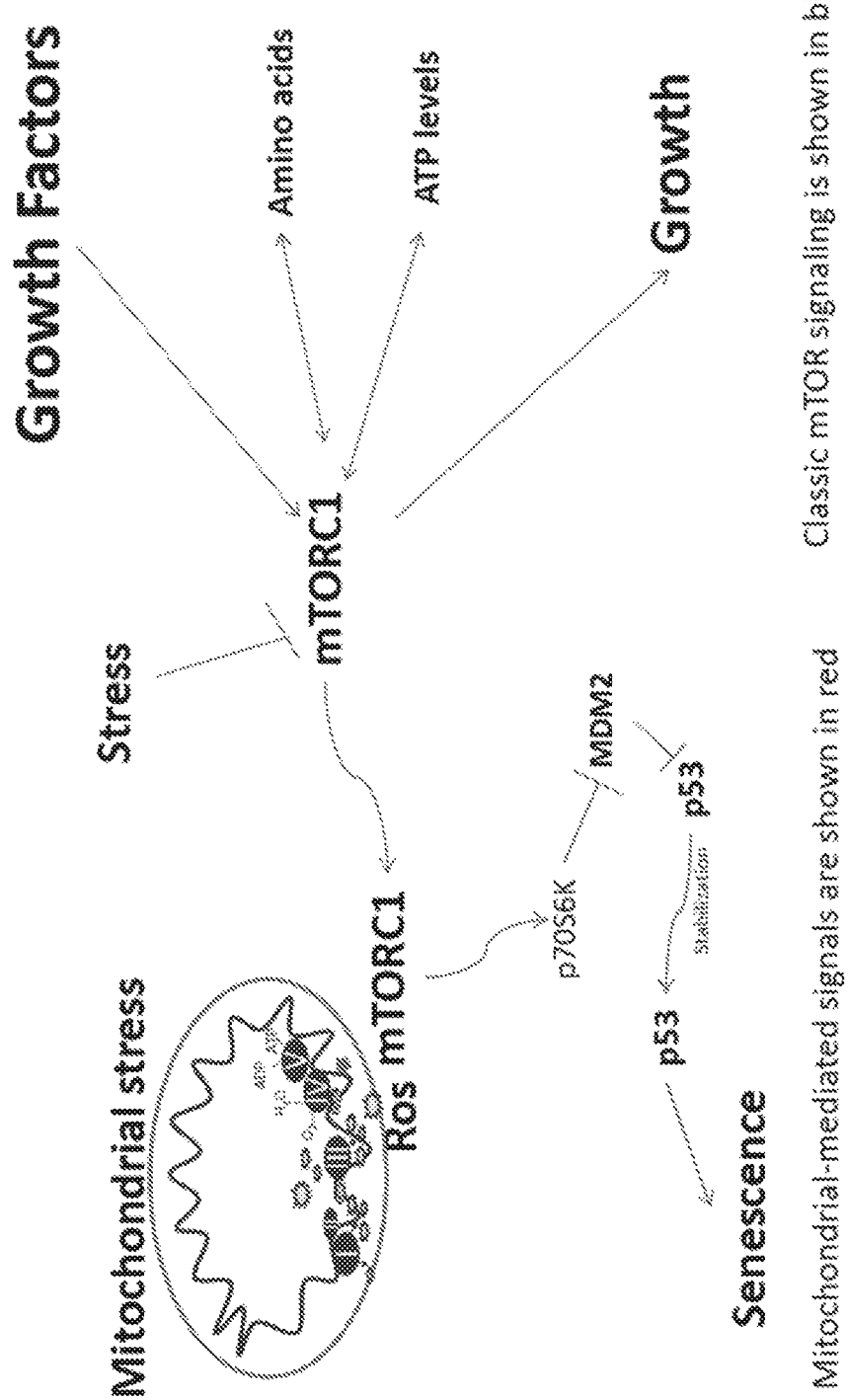

Survival of human cells following mitochondrial stress

COMPOSITIONS AND METHODS FOR TREATING OR PREVENTING DERMAL DISORDERS

CROSS-REFERENCE TO RELATED APPLICATIONS

The present application is a 35 U.S.C. § 371 national phase application from, and claims priority to, International Application No. PCT/US2016/052442, filed Sep. 19, 2016, and published under PCT Article 21(2) in English, which claims priority under 35 U.S.C. § 119(e) to U.S. Provisional Patent Application No. 62/232,228, filed Sep. 24, 2015, all of which applications are incorporated herein by reference in their entireties.

STATEMENT REGARDING FEDERALLY SPONSORED RESEARCH OR DEVELOPMENT

This invention was made with government support under grant number AG039799 awarded by the National Institute of Aging/National Institutes of Health. The government has certain rights in the invention.

BACKGROUND OF THE INVENTION

Aging of the skin is the most prominent feature of the aging process, being caused by multiple factors such as intrinsic aging process and UV light exposure. Age-related dermal disorders include for example dermal atrophy, actinic keratosis, pseudoscars, lentigines, focal areas of dermal thickening, and coarse wrinkles.

Dermal atrophy, also called skin atrophy or atrophy, is a disorder manifesting thinning or depression of skin due to reduction of underlying tissue. Dermal atrophy is a major clinical problem in the elderly population. Loss of dermal integrity leads to increased fragility of the skin and precludes the use of intravenous lines in many cases. Impairment in wound healing is an important clinical sequelae of reduced dermal integrity leading to an increase in the number of the infections and complications following injury. Pseudoscars are stellate lesions that occur spontaneously in elderly individuals which can occur as senile and presenile forms. These lesions can be found in 20% of patients over the age of 70. Lentigines (or liver spots) are areas of hyperpigmentation occurring with age and may represent precursor lesions to lentigo maligna and melanoma. They may increase with age and become common in middle aged and elderly individuals. Seborrheic or actinic keratosis, which comprise focal areas of epidermal thickening, can occur, possibly representing a response to damage. Similarly, coarse wrinkles are thought to arise from a damage response. Currently, treatments for age-related dermal atrophy and related disorders include subdermal hyaluronic acid injection, injection of botulinum toxin or topical application of antioxidant such as vitamin C, green tea extract, and coenzyme Q, but these agents are not able to fully treat these conditions.

Cellular senescence is a stress response activated by mammalian cells upon exposure to several insults, such as oxidative stress, genotoxic stress, telomere attrition, or dysregulated mitogenic signaling. These stresses activate the senescence response by triggering two pathways: the p53/p21$^{CIP1/WAF1}$ and the p16$^{INK4A}$/Rb pathway, which are required to establish and maintain the senescence response. Senescence-inducing stimuli can cause DNA damage and trigger a sustained DNA damage response (DDR): in response to sustained, unresolved DNA damage, the Ataxia Telangiectasia Mutant (ATM) kinase activates p53 and its transcriptional target p21$^{CIP1/WAF1}$, which arrests cellular proliferation by inhibiting cell-cycle-dependent kinases. In addition, the same senescence-inducing stimuli can trigger the activation of the Stress-Activated Protein Kinase p38 MAPK independently of DNA damage. p38 MAPK then can promote the arrest of the cell-cycle and establish senescence by activating the transcription factor HBP1, which increases the expression of p16$^{INK4A}$. These two pathways seem to establish senescence with different kinetics: the DDR pathway usually mediate the initial arrest by increasing the levels of p21$^{CIP1/WAF1}$, and only at later times senescence is reinforced by expression of p16$^{INK4A}$. Furthermore, the p53 and the p38 MAPK pathways appear to be mostly independent of one another and are thus redundant, even though cross-talk between them may exist.

Mammalian/mechanistic target of rapamycin (mTOR) is an intracellular protein complex that is responsive to both growth factors and nutrient availability, and which also impacts mitochondrial function. It is comprised of the TOR kinase (originally identified in yeast, and known as mTOR in mammals), accessory proteins, and downstream mediators including the ribosomal S6 kinase (p70S6K) a key downstream target of TOR. The TOR signaling pathway is highly conserved in eukaryotes and is functionally defined as the target of the highly-specific antifungal, rapamycin.

The proteins that comprise the core mTOR complex are the ser-thr kinase mTOR, also known as the FKBP-12-rapamycin associated protein (FRAP1), and mammalian lethal with SEC 13 protein 8 (mLST8). These core components have the capability of forming either of two complexes, mTORC1 or mTORC2, which are distinguishable by their sensitivity to rapamycin. The rapamycin-sensitive mTORC1 contains the scaffolding protein regulatory-associated protein of mTOR (Raptor), whereas the rapamycin-insensitive complex mTORC2 contains the scaffolding protein rapamycin-insensitive companion of mTOR (Rictor). These scaffolding proteins function to direct mTORC1 and mTORC2 to their respective targets. Additional components are unique to each complex. For example, proline-rich Akt/PKB substrate 40 KDa (PRAS40) is an inhibitory protein associated with mTORC1, whereas the stress-activated MAP kinase-interacting protein 1 (Sin1) and the protein observed with Rictor-1 (proctor) protein are associated with mTORC2. The primary function attributed to the mTOR complex is the promotion of cell proliferation and growth of cells.

There is thus a need in the art for novel compositions and methods that can be used to treat or prevent certain age-related dermal conditions in a mammalian subject in need thereof, such as a human. The present invention fulfills this need.

BRIEF SUMMARY OF THE INVENTION

The invention provides a method of treating or preventing an age-related dermal disorder in a mammalian subject in need thereof. The invention further provides a method of increasing the lifespan of a mammalian fibroblast. The invention further provides a method of preserving cell organization of a mammalian fibroblast. The invention further provides a method of preventing or minimizing senescence of a mammalian fibroblast. The invention further provides a kit for treating or preventing an age-related dermal disorder in a mammalian subject in need thereof.

In certain embodiments, the method comprises topically administering to the subject a composition comprising a therapeutically effective amount of a mTORC1 inhibitor or a salt, solvate, enantiomer or diastereoisomer thereof.

In certain embodiments, the method comprises contacting the fibroblast with a composition comprising an effective amount of a mTORC1 inhibitor or a salt, solvate, enantiomer or diastereoisomer thereof.

In certain embodiments, the age-related dermal disorder is at least one selected form the group consisting of dermal atrophy, seborrheic or actinic keratosis, pseudoscars, lentigines, focal areas of dermal thickening, and coarse wrinkles.

In certain embodiments, the mTORC1 inhibitor is at least one selected from the group consisting of BEZ235, rapamycin, everolimus, AZD8055, Temsirolimus, KU-0063794, P1-103. Torkinib, Tacrolimus, Ridaforolimus, INK-128, Voxtalisib. Torin-1, Omipalisib, OSI-027, PF-04691502, Apitolisib, GSK1059615, WYE-354, Gedatolisib, AZD-2014, Torin-2, WYE-125132, BGT226, Palomid-529, PP121, WYE-687, CH5132799, Way-600, ETP-46464, GDC-0349, XL388, and Zotarolimus, or a salt, solvate, enantiomer or diastereoisomer thereof. In other embodiments, the mTORC1 inhibitor is at least one selected from the group consisting of rapamycin, Ridaforolimus, and Everolimus, or a salt, solvate, enantiomer or diastereoisomer thereof. In yet other embodiments, the mTORC1 inhibitor is rapamycin, or a salt, solvate, enantiomer or diastereoisomer thereof.

In certain embodiments, the subject is a human. In other embodiments, the composition is applied topically to the skin of the subject.

In certain embodiments, the composition comprises about 0.001-1% by weight of the mTORC1 inhibitor, or a salt, solvate, enantiomer or diastereoisomer thereof. In other embodiments, the mTORC1 inhibitor is rapamycin, or a salt, solvate, enantiomer or diastereoisomer thereof. In yet other embodiments, the composition further comprises a dermatologically acceptable carrier. In yet other embodiments, the dermatologically acceptable carrier is at least one selected from the group consisting of a solvent, lubricant, emollient, emulsifier, moisturizer, thickening wax, softener, fragrance, preservative, and artificial color. In yet other embodiments, the dermatologically acceptable carrier comprises petrolatum.

In certain embodiments, the fibroblast is a dermal fibroblast. In other embodiments, the dermal fibroblast is in vivo and part of a mammalian subject's skin.

In certain embodiments, the kit comprises a composition comprising a therapeutically effective amount of a mTORC1 inhibitor, or a salt, solvate, enantiomer or diastereoisomer thereof. In other embodiments, the kit further comprises an applicator. In yet other embodiments, the kit further comprises instructions for topically administering the composition to the subject.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A is a bar graph illustrating mitochondrial membrane potential as assessed by tetramethylrhodamine ethyl ester, perchlorate (TMRE) staining. FIG. 1B is a bar graph illustrating mitochondrial ROS levels. FIG. 1C is a bar graph illustrating mitochondrial mass. FIG. 1D is a bar graph illustrating total cellular ROS. FIG. 1E is a graph illustrating oxygen consumption/cell as a function of time following the addition of the mitochondrial inhibitors oligomycin, carbonyl cyanide p-triflouromethoxyphenylhydrazone (FCCP), or a combination of rotenone and antimycin A. FIG. 1F is a bar graph illustrating the calculated rates of basal respiration. FIG. 1G is a bar graph illustrating the calculated rates of maximal respiration. FIG. 1H is a bar graph illustrating the calculated rates of ATP-linked respiration. FIG. 1I is a bar graph illustrating the calculated rates of proton leak. Each measurement represents a minimum of triplicate cultures and all measurements were repeated a minimum of 2 times with similar results. Bars marked with an asterisk represent values that are significantly different from relative control values at $P<0.05$ and bars marked with an # represent values that are significantly different between rapamycin-treated and untreated cells within the same treatment group (control or exposed to NRTIs).

FIG. 2A depicts steady state levels of the indicated electron transport chain (ETC) proteins, along with the outer mitochondrial membrane protein voltage-dependent anion channel (VDAC), assessed by immunoblot in cardiac fibroblasts exposed to NRTIs. FIG. 2B depicts the steady state levels of Pink1, the Pink 1 cleavage product, and Parkin. FIG. 2C depicts the steady state levels p62 and actin. FIG. 2D depicts the results of a nanostring analysis of mRNA levels for the ETC subunits included in NADH dehydrogenase (ubiquinone) 1 beta subcomplex, 8 (NDUFB8) (complex 1). FIG. 2E depicts the results of a nanostring analysis of mRNA levels for ETC subunits included in ubiquinol-cytochrome c reductase core protein II (UQCRC2) (complex 3). FIG. 2F depicts the results of a nanostring analysis of mRNA levels for the ETC subunits included in succinate dehydrogenase (ubiquinone) ironsulfur subunit (SDHB) (complex 2). FIG. 2G depicts the results of a nanostring analysis of mRNA levels for the ETC subunits included in cytochrome c oxidase subunit I (mt-Co 1) (complex 4). FIG. 2H depicts the results of a nanostring analysis of mRNA levels for the ETC subunits included in ATP5A1 (complex 5). Each immunoblot represents a minimum of two independent experiments with similar results. Gray bars represent data from control cultures while black bars represent data from rapamycin-treated cultures. Bars marked with an asterisk represent values that are significantly different from relative control values at $P<0.05$ and bars marked with an # represent values that are significantly different between rapamycin-treated and untreated cells within the same treatment group (control or exposed to NRTIs). Nanostring results are representative of 2 independent experiments.

FIG. 3A illustrates data from human cardiac fibroblasts showing steady state levels of p16, p21, p53, lamin B1, and IL-6 known to be altered during the senescence response. Actin levels are presented as a loading control. FIG. 3B is a bar graph illustrating the percentage of cells staining positive for SA-β galactosidase activity. FIG. 3C is a bar graph illustrating steady state mRNA levels for p21 determined by nanostring analysis in cells exposed to NRTIs. FIG. 3D is a bar graph illustrating steady state mRNA levels for lamin B1 determined by nanostring analysis in cells exposed to NRTIs. FIG. 3E is a bar graph illustrating a comparative analysis of p21, comparing early passage cells with cells that have undergone replicative senescence as well as cells that were maintained in rapamycin containing medium allowing lifespan extension. FIG. 3F is a bar graph illustrating a comparative analysis of lamin B1, comparing early passage cells with cells that have undergone replicative senescence as well as cells that were maintained in rapamycin containing medium allowing lifespan extension. Grey bars represent cells maintained under standard culture conditions and black bars represent cells maintained in the presence of rapamycin. Bars marked with an asterisk represent values that are significantly different from relative control values at $P<0.05$ and bars marked with an # represent values that are significantly different between rapamycin-treated and untreated cells within the same treatment group (e.g. control or exposed to NRTIs).

FIG. 4A depicts the steady state levels of p16, p21, p53 and lamin B1 known to be altered during the senescence response. FIG. 4B is a bar graph illustrating the percentage of cells staining positive for lysosomal SA-β galactosidase activity. FIG. 4C depicts the results of an immunoblot analysis showing steady state levels of p16, p21, p53, actin, and catalase known to be altered during the senescence response, after human cardiac fibroblasts were infected with an adenoviral vector expressing the mt-catalase protein or an empty vector during exposure to NRTIs. Immunoblot represents a minimum of two independent experiments with similar results. FIG. 4D is a bar graph illustrating the percentage of cells staining positive for lysosomal SA-β galactosidase activity, after human cardiac fibroblasts were infected with an adenoviral vector expressing the mt-catalase protein or an empty vector during exposure to NRTIs. FIG. 4E depicts steady state levels of p16, p21, and lamin B1 associated with senescence. Grey bars represent cells maintained under standard culture conditions and black bars represent cells maintained in the presence of rapamycin. Bars marked with an asterisk represent values that are significantly different from relative control values at $P<0.05$. Bars marked with an # represent values that are significantly different between rapamycin-treated and untreated cells within the same treatment group (control or exposed to NRTIs).

FIG. 5A depicts the phosphorylation status of the ribosomal S6 protein and MDM2 in response to NRTI exposure as assessed by immunoblot analysis in human cardiac fibroblasts. Extracts from cultures maintained under standard culture conditions are shown in the left 3 lanes while cultures maintained in the presence of 1 nM rapamycin are shown in the 2 right hand lines. Cultures were exposed to 10 or 20 μM NRTIs for 7 days in the case of control cultures while rapamycin treated cultures were exposed to 20 μM NRTIs for 7 days. FIG. 5B depicts the phosphorylation status of the ribosomal S6 protein and MDM2 after cells were exposed to NRTIs for 7 days followed by incubation with specific kinase inhibitors targeting either the p70 S6 kinase (PF-4708671) or MEK1/2 (U0126) for the final 2 hours. FIG. 5C depicts the phosphorylation status of the ribosomal S6 protein and MDM2 after cells were exposed to NRTIs for 7 days followed by incubation with specific kinase inhibitors targeting MEK1/2 (U0126), Raf (GW5047), or p90RSK (BI-D1870), for the final 2 hours. An additional set of cultures was treated with the free radical scavengers Trolox and N-acetylcysteine in combination during exposure to NRTIs. FIG. 5D depicts the phosphorylation status of the ribosomal S6 protein and MDM2 after cells were treated with a specific p38 MAPK inhibitor (SB203580) during exposure to NRTIs. With the exception of FIG. 5D, each immunoblot represents a minimum of two independent experiments with similar results. Each immunoblot is shown with actin as a loading control.

FIG. 6A depicts an immunoblot analysis of the phosphorylation status of the ribosomal S6 protein and MDM2 in cardiac fibroblasts cultured in the presence of mito-Q or the inactive carrier thiamine pyrophosphate (TPP) for the duration of NRTI exposure. FIG. 6B depicts an immunoblot analysis for phosphorylation of the ribosomal S6 protein and MDM2 in cardiac fibroblasts infected with adenoviral particles harboring a construct expressing the mt-catalase or an empty viral vector prior to NRTI exposure. Each immunoblot represents a minimum of two independent experiments with similar results and is shown with actin as a loading control. FIG. 6C is a Seahorse Bioanalyzer analysis illustrating calculated rates of basal respiration after cardiac fibroblasts treated with mito-Q or TPP during exposure to NRTIs. FIG. 6D is a Seahorse Bioanalyzer analysis illustrating calculated rates of maximal respirations after cardiac fibroblasts treated with mito-Q or TPP during exposure to NRTIs. FIG. 6E is a Seahorse Bioanalyzer analysis illustrating calculated rates of ATP-linked respiration after cardiac fibroblasts treated with mito-Q or TPP during exposure to NRTIs. FIG. 6F is a Seahorse Bioanalyzer analysis illustrating calculated rates of proton leak after cardiac fibroblasts treated with mito-Q or TPP during exposure to NRTIs. FIG. 6G is a bar graph illustrating the mean fluorescence intensity of mitochondrial ROS. Bars with an asterisk represent values that are significantly different from relative control values at $P<0.05$ and bars marked with an # represent values that are significantly different between TPP and mito-Q-treated cells within the same treatment group (control or exposed to NRTIs).

FIG. 7A depicts phosphorylation status of the ribosomal S6 protein and MDM2 after serum-deprived cardiac fibroblasts exposed to increasing concentrations of hydrogen peroxide for 2 hours. Serum-stimulated cultures are included in the right hand lane as a positive control for growth factor stimulation of ribosomal S6 phosphorylation. FIG. 7B depicts the phosphorylation status of the ribosomal S6 protein in cells exposed to the indicated concentrations of rotenone for 16 hours. Serum deprived cardiac fibroblasts were exposed to rotenone at concentrations ranging from 1 to 50 nM. Steady state levels of actin are presented as a control for equal protein loading.

FIG. 8A is a set of images illustrating cells infected with an adenoviral construct harboring an expression construct that produces a GFP protein fused to a mitochondrial targeting sequence (green). These cells were fixed and stained with an antibody that recognizes Raptor (red) and counter stained with 4',6-diamidino-2-phenylindole (DAPI) to visualize DNA (blue). FIG. 8B is a representative confocal image of control fibroblasts (not exposed to NRTIs) illustrating a co-localization event in fibroblasts expressing the mitochondrial GFP following exposure to NRTIs for 7 days. FIG. 8C is a bar graph illustrating the quantification of co-localization events as determined by both confocal and deconvolution microscopy. Bars marked with an asterisk represent values that are significantly different from relative control values at P<0.05 and bars marked with an # represent values that are significantly different between rapamycin-treated and untreated cells within the same treatment group (control or exposed to NRTIs). Co-localization experiments were performed by four independent evaluators over a series of experiments examining Raptor and mt-GFP co-localization by both confocal microscopy and deconvolution microscopy. Quantitative data were generated from counts using deconvolution microscopy.

FIG. 9A is a bar graph illustrating the levels of mitochondrial ROS in early passage and senescent cardiac fibroblasts. FIG. 9B is a bar graph illustrating the levels of total cellular ROS in early passage and senescent cardiac fibroblasts. Grey bars represent cells maintained under standard culture conditions and black bars represent cells maintained in the presence of 1 nM rapamycin. FIG. 9C is a graph illustrating oxygen consumption rate normalized to cell number, as a function of time following the addition of the mitochondrial inhibitors oligomycin. FCCP, or a combination of rotenone and antimycin A. FIG. 9D is a Seahorse Bioanalyzer analysis illustrating basal respiration of mitochondrial function in human cardiac fibroblasts. FIG. 9E is a Seahorse Bioanalyzer analysis illustrating maximal respiration of mitochondrial function in human cardiac fibroblasts. FIG. 9F is a Seahorse Bioanalyzer analysis illustrating ATP-linked respiration of mitochondrial function in human cardiac fibroblasts. FIG. 9G is a Seahorse Bioanalyzer analysis illustrating proton leak of mitochondrial function in human cardiac fibroblasts. FIG. 9H depicts protein lysates derived from cells at increasing population doublings probed for markers of senescence, p21 and p16, as well as the phosphorylated forms of the ribosomal S6 and MDM2 proteins. FIG. 9I depicts protein lysates probed for the phosphorylation status of the ribosomal S6 protein and MDM2, after fully senescent cultures were treated with the ROS scavengers Trolox and N-acetylcysteine, the p90RSK inhibitor BI-D1870, or infected with adenoviral particles harboring a construct that expresses the mt-catalase protein or an empty vector control. Bars marked with an asterisk represent values that are significantly different from relative control values at P<0.05, and bars marked with an # represent values that are same treatment group (control or exposed to NRTIs).

FIG. 10 is a schematic illustration of a model for mTORC1 integration of multiple signals to generate growth response or senescence arrest. As demonstrated herein, additional inputs to mTORC1 exist in the form of cellular redox status and mitochondrial function that may redirect mTORC1 to support a senescent growth arrest through the p70 S6 kinase mediated modulation of MDM2 and p53 activity. These connections are shown in red (mTORC1→p70S6K-|MDM2-|p53→stabilization→p53→senescence).

FIG. 11A is a bar graph illustrating comet assay results for cells exposed to NRTIs or hydrogen peroxide as a positive control. The white bar represents control data; grey bar represents data from cells exposed to 10 or 20 µg/ml NRTI for 7 days; and the black bar represents data from cells exposed to 200 µM hydrogen peroxide for 2 hours. An asterisk represents values that are significantly different from relative control values at P<0.05. FIG. 11B depicts the results of an immunoprecipitation experiment using antibodies against p53. Cell lysates from control and rapamycin-treated cultures, with or without NRTI exposure for 7 days, were subjected to immunoprecipitation using anti-p53 antibodies followed by immunoblot analysis for MDM2 and subsequently for p53. FIG. 11C depicts levels of p53, MDM2, and phosphorylated MDM2 in the samples used for immunoprecipitation in FIG. 11A. FIG. 11D depicts levels of p53 after control and rapamycin-treated cultures were exposed to NRTIs for 7 days followed by a 2-hour incubation with MG132 to inhibit proteasome activity. Modified p53 refers to higher molecular weight forms recognized by the anti-p53 antibody. FIG. 11E is an image illustrating cytosolic level of MDM2 without exposure to NRTIs, and an image illustrating cytosolic level of MDM2 with exposure to NRTIs. Representative photomicrographs of cells stained for MDM2 (red) and counter stained for DNA (blue). FIG. 11F is a bar graph illustrating relative intensity of cytosolic MDM2 staining as determined by Image J Analysis.

FIGS. 12A-12B depict representative photomicrographs of cells expressing the mt-GFP protein (green) stained for Raptor (red) under control conditions. FIGS. 12C-12D depict representative photomicrographs of cells expressing the mt-GFP protein stained for Raptor following exposure to NRTIs. Co-localization events are indicated by arrows.

DETAILED DESCRIPTION OF THE INVENTION

Figure 1A:
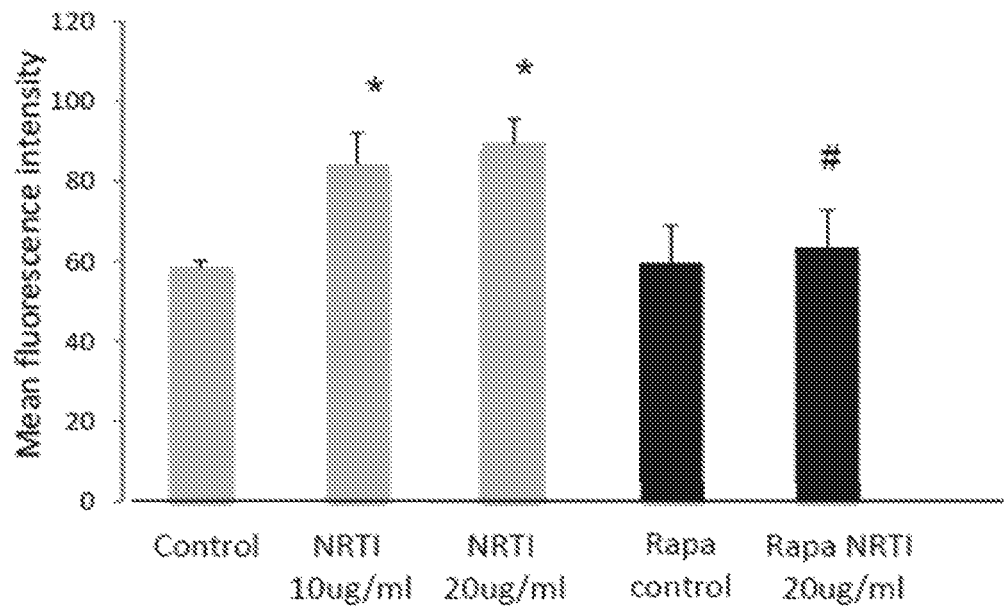
FIGS. 1A-1I are a set of graphs illustrating changes in mitochondrial parameters in response to NRTIs and rapamycin. Human cardiac fibroblasts were maintained with or without rapamycin (1 nM). After 7 days exposure to NRTIs, parameters of mitochondrial status and function were examined. Grey bars represent cells maintained under standard culture conditions and black bars represent cells maintained in the presence of rapamycin.

The present invention relates, in one aspect, to the unexpected discovery that the compositions and methods of the invention can be used to treat or prevent age-related dermal disorders including, but not limited to, dermal atrophy, seborrheic keratosis, actinic keratosis, pseudoscars, lentigines, focal areas of dermal thickening, and coarse wrinkles. In certain embodiments, the compositions and methods of the invention are useful for treating or preventing dermal atrophy in a subject in need thereof. In other embodiments, the compositions of the invention comprises therapeutically effective amounts of at least one mTORC1 inhibitor. In yet other embodiments, the compositions of the invention comprise the mTORC1 inhibitor as the only ingredient that is active against the age-related dermal condition. In yet other embodiments, the mTORC1 inhibitor is also a mTORC2 inhibitor.

The compositions and methods of the invention enhance lifespan of fibroblasts and improve the growth and stress resistance of normal fibroblasts. Without wishing to be limited by any theory, this may be associated with a decrease in inflammatory cytokine production. In certain embodiments, delivery of therapeutically effective amounts of a mTORC1 inhibitor to the dermal layers induces mesenchymal responses that influence dermal homeostasis. In other embodiments, delivery of therapeutically effective amounts of a mTORC1 inhibitor to the dermal layers produces an increase in dermal thickness and improvement in skin function.

As demonstrated herein, mitochondrial ROS was identified as a novel input for mTORC1. Based upon both fluorescent indicators and the impact of ROS scavengers, the present results support the finding that mitochondrial-generated ROS serves to activate mTORC1 (FIG. 10). This is reflected by increased phosphorylation of both the ribosomal S6 protein and MDM2 observed in the experimental setting. Inhibition of mTORC1 by rapamycin prevented these responses, as did interventions aimed at reducing mitochondrial ROS, such as the expression of a mitochondrial-targeted catalase or treatment with ROS scavengers. Analysis of oxygen consumption as a measure of mitochondrial activity revealed an increase in basal and ATP-linked respiration in both settings, cells exposed to NRTIs as well as in those in replicative senescence. Similarly, in both settings proton leak and mitochondrial ROS production were increased. These findings suggest that the generation of mitochondrial ROS serves as a trigger for the activation of mTORC1. This interpretation is supported by the fact that interventions designed to reduce mitochondrial ROS reduced phosphorylation of the ribosomal S6 protein.

In terms of downstream consequences of mitochondrial ROS induction of mTORC1/p70S6K activity, MDM2 phosphorylation appeared to lead to a stabilization of p53 and increased expression of downstream targets such as p21. Consistent with this, decreased association of p53 with MDM2 was shown by co-immunoprecipitation and increased cytosolic MDM2 in cells exposed to NRTIs. In addition, it was observed a decrease in high molecular weight forms of p53 in cells exposed to NRTIs, while rapamycin-treated cells contained elevated levels of these high molecular weight forms of p53 that were visible only following inhibition of the proteasome. This effect of rapamycin on p53 may underlay the lack of activation of p53 target genes, such as p21, in rapamycin-treated cells and contributed to the delayed senescence observed when cells were cultured in the presence of rapamycin at concentrations sufficient to influence mTORC1 signaling but not sufficient to completely block proliferation.

In certain aspects, the present results show that mTORC1 signaling through the p70S6K may be responsive to ROS generated by mitochondria. Activation of mTORC1/p70S6K occurred in settings of mitochondrial dysfunction, replicative senescence, and in aged tissue. Rapamycin ameliorated both the mitochondrial ROS production and blocks the mTORC1/p70S6K response. These effects of rapamycin supported the beneficial effects observed in terms of longevity and in age-related disorders like dermal atrophy following rapamycin treatment.

Definitions

As used herein, each of the following terms have the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics and chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount a temporal duration, and the like, the term "about" is meant to encompass variations of ±20% or ±10%, ±5%, ±1%, or ±0.1% from the specified value, as such variations are appropriate to perform the disclosed methods.

As used herein, "dermatologically acceptable carrier" or "dermatologically acceptable excipient" refers to the compositions or components that are suitable for use in contact with human keratinous tissue without undue toxicity, incompatibility, instability, allergic response, and the like.

A "disease" is a state of health of an animal wherein the animal cannot maintain homeostasis, and wherein if the disease is not ameliorated, the animal's health continues to deteriorate. A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount" or "therapeutically effective amount" or "pharmaceutically effective amount" of a compound are used interchangeably to refer to the amount of the compound sufficient to provide a beneficial effect to the subject to which the compound is administered. The term to "treat," as used herein, means reducing the frequency with which symptoms are experienced by a patient or subject or administering an agent or compound to reduce the severity with which symptoms are experienced. An appropriate therapeutic amount in any individual case may be determined by one of ordinary skill in the art using routine experimentation.

As used herein, the term "FTC" refers to emtricitabine or a salt or solvate thereof.

As used herein, an "instructional material" includes a publication, a recording, a diagram, or any other medium of expression that can be used to communicate the usefulness of a compound, composition, assay or method of the invention in a kit for suppressing or reducing systemic immune response in a subject. The instructional material of the kit of the invention can, for example, be affixed to a container which contains the identified compound, composition, assay, or methods of the invention or be shipped together with a container that contains the identified compound, composition, assay, or method. Alternatively, the instructional material can be shipped separately from the container with the intention that the instructional material and the compound, composition, assay, or method be used cooperatively by the recipient.

As used herein, the term "modulate" means, with respect to disease states or conditions associated with binding of a compound of the present invention to a receptor contemplated in the present invention, to produce, either directly or indirectly, an improvement or lessening of a condition or disease state which was, prior to administration of a compound according to the present invention, sub-optimal and in many cases, debilitating and even life threatening. Modulation may occur by virtue of agonist activity, antagonist activity or mixed agonist/antagonist activity (depending on the receptor site).

As used herein, the term "NRTI" refers to a nucleotide/nucleoside reverse transcriptase inhibitor.

As used herein, the term "pharmaceutically acceptable" refers to a material, such as a carrier or diluent, which does not abrogate the biological activity or properties of the composition, and is relatively non-toxic, i.e., the material may be administered to an individual without causing undesirable biological effects or interacting in a deleterious manner with any of the components of the composition in which it is contained.

As used herein, the term "pharmaceutical composition" or "composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary, intracranial and topical administration. In certain embodiments, the administration comprises topical administration.

As used herein, a "subject" refers to a human or non-human mammal. Non-human mammals include, for example, livestock and pets, such as ovine, bovine, porcine, canine, feline and murine mammals. In certain embodiments, the subject is human.

As used herein, the term "TDF" refers to tenofovir disoproxil fumarate, or a salt or solvate thereof.

As used herein, "topical administration" or "topical application" refers to a medication applied to body surfaces such as the skin or mucous membranes.

As used herein, the term "treatment" or "treating" is defined as the application or administration of a therapeutic agent, i.e., a composition useful within the invention (alone or in combination with another pharmaceutical agent), to a subject, or application or administration of a therapeutic agent to an isolated tissue or cell line from a subject (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder or the potential to develop the disease or disorder. Such treatments may be specifically tailored or modified, based on knowledge obtained from the field of pharmacogenomics.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions

The composition of the invention comprises a therapeutically effective amount of a mTORC1 inhibitor, or salt, solvate, enantiomer or diastereoisomer thereof. In certain embodiments, the mTORC1 inhibitor is at least one selected from the group consisting of BEZ235, rapamycin, everolimus, AZD8055, Temsirolimus, KU-0063794, PI-103, Torkinib, Tacrolimus, Ridaforolimus, INK-128. Voxtalisib, Torin-1, Omipalisib, OSI-027, PF-04691502, Apitolisib, GSK1059615, WYE-354, Gedatolisib, AZD-2014, Torin-2, WYE-125132, BGT226, Palomid-529, PP121, WYE-687, CH5132799, Way-600, ETP-46464, GDC-0349, XL388, and Zotarolimus.

BEZ235 is also known as 2-methyl-2-(4-(3-methyl-2-oxo-8-(quinolin-3-yl)-2,3-dihydroimidazo[4,5-c]quinolin-1-yl)phenyl)propanenitrile, and has a formula of:

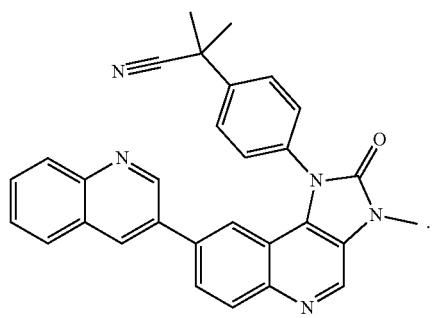 [SMILES: Cn1c(=O)n(-c2ccc(C(C)(C)C#N)cc2)c2c3cc(-c4cnc5ccccc5c4)ccc3ncc21]

Rapamycin is also known as (3S,6R,7E,9R,1R,12R,14S,15E,17E,19E,21 S,23S, 26R,27R,34aS)-9,10,12,13,14,21,22,23,24,25,26,27,32,33,34,34a-Hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4-oxaazacyclo hentriaconine-1,5,11,28,29(4H,6H,31H)-pentone, and has a formula of:

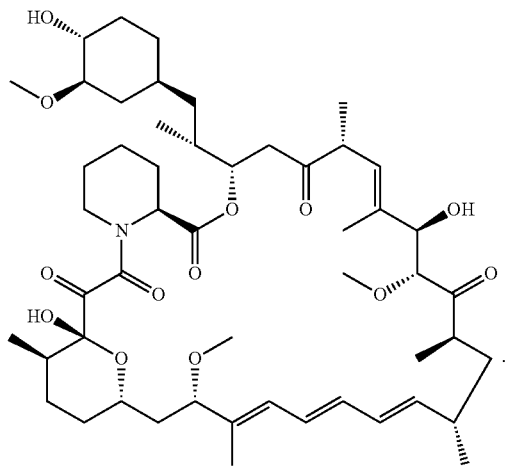 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

Everolimus is also known as dihydroxy-12-[(2R)-1-[(1S,3R,4R)-4-(2-hydroxy ethoxy)-3-methoxycyclohexyl]propan-2-yl]-19,30-dimethoxy-15,17,21,23,29,35-hexamethyl-11,36-dioxa-4-azatricyclo[30.3.1.0 hexatriaconta-16,24,26,28-tetraene-2,3,10,14,20-pentone, and has a formula of:

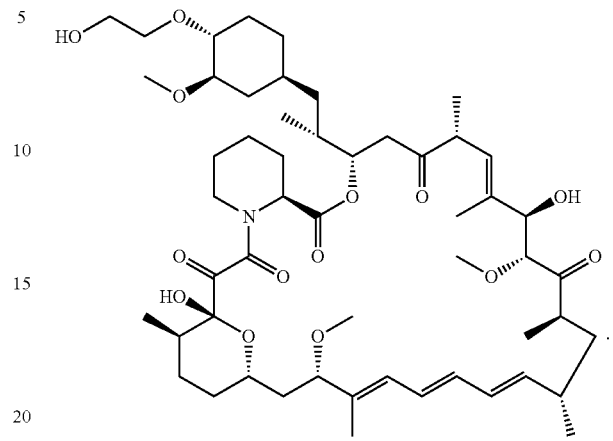

AZD8055 is also known as 5-(2,4-bis((S)-3-methylmorpholino)pyrido[2,3-d]pyrimidin-7-yl)-2-methoxyphenyl)methanol, and has a formula of:

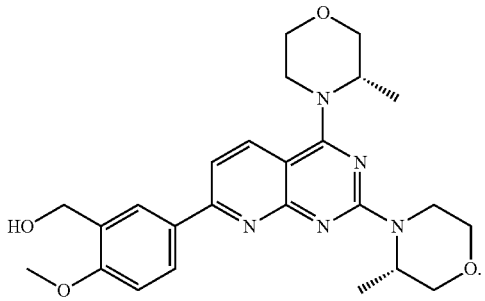 [SMILES: COc1ccc(-c2ccc3c(N4CCOC[C@@H]4C)nc(N4CCOC[C@@H]4C)nc3n2)cc1CO]

Temsirolimus is also known as 42-[3-hydroxy-2-(hydroxymethyl)-2-methyl propanoate]-rapamycin, and has a formula of:

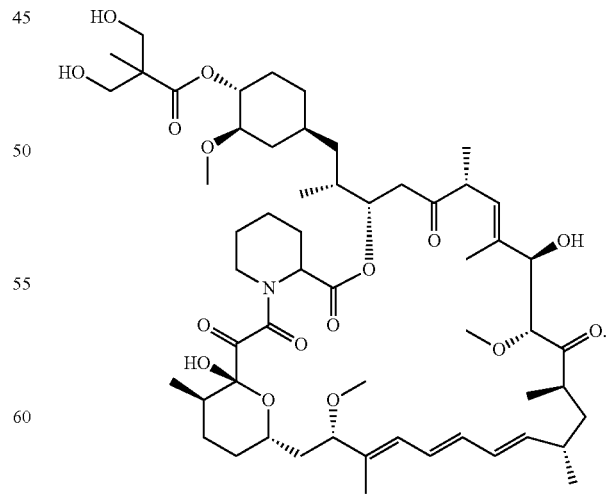

PI-103 is also known as 3-[4-(4-morpholinyl)pyrido[3',2':4,5]furo[3,2-d]pyrimidin-2-yl]-phenol, and has a formula of:

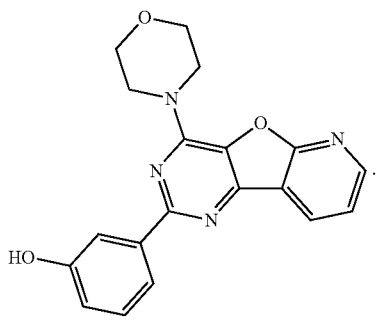 [SMILES: Oc1cccc(-c2nc(N3CCOCC3)c3oc4ncccc4c3n2)c1]

KU-0063794 is also known as (5-(2-((2R,6S)-2,6-dimethylmorpholino)-4-morpholinopyrido[2,3-d]pyrimidin-7-yl)-2-methoxyphenyl)methanol, and has a formula of:

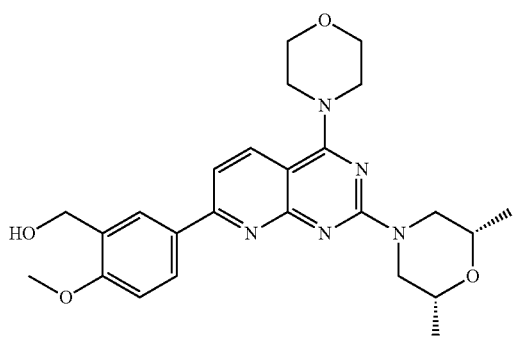

Torkinib is also known as 2-(4-amino-1-isopropyl-1H-pyrazolo[3,4-d]pyrimidin-3-yl)-1H-indol-5-ol, and has a formula of:

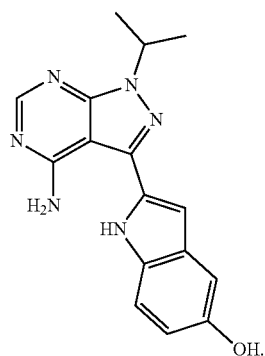 [SMILES: CC(C)n1nc(-c2cc3cc(O)ccc3[nH]2)c2c(N)ncnc21]

Tacrolimus is also known as 3S-13R*[E(1S*,3S*,4S*)], 4S*,5R*,8S*,9E,12R*, 14R*,15S*,16R*,18S*,19S*, 26aR*-5,6,8,11,12,13,14,15,16,17,18,19,24,25,26,26a-hexadecahydro-5, 19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c][1,4]oxaazacyclotricosine-1,7,20,21(4H,23H)-tetrone, and has a formula of:

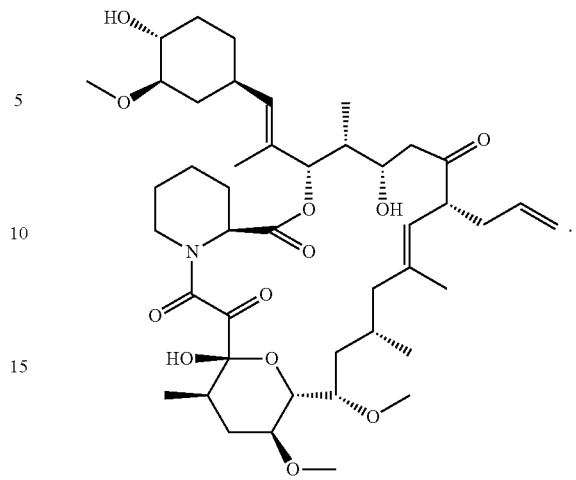

Ridaforolimus is also known as 42-(dimethylphosphinate)-rapamycin, and has a formula of:

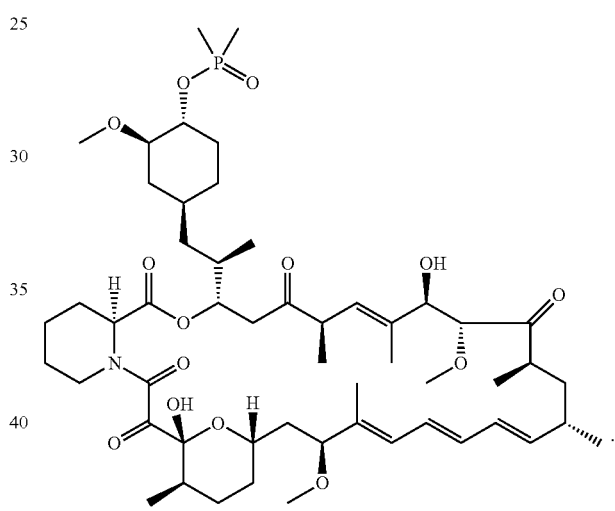

INK-128 is also known as 3-(2-aminobenzo[d]oxazol-5-yl)-1-isopropyl-1H-pyrazolo[3,4-d]pyrimidin-4-amine, and has a formula of:

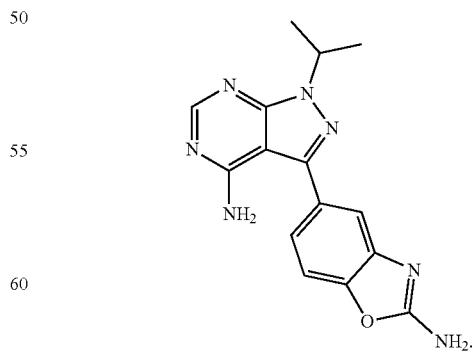

Voxtalisib is also known as N-[4-[[[3-[(3,5-dimethoxyphenyl)amino]-2-quinoxalinyl]amino]sulfonyl]phenyl]-3-methoxy-4-methyl-benzamide, and has a formula of:

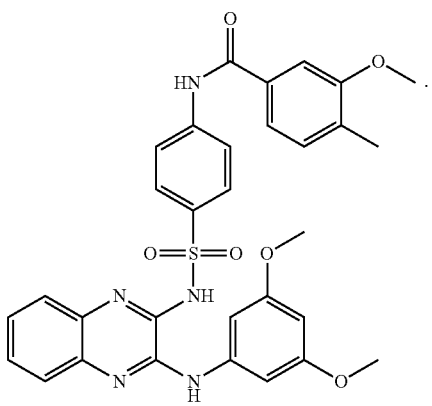 [SMILES: COc1cc(Nc2nc3ccccc3nc2NS(=O)(=O)c2ccc(NC(=O)c3ccc(C)c(OC)c3)cc2)cc(OC)c1]

Torin-1 is also known as 1-[4-[4-(1-Oxopropyl)-1-piperazinyl]-3-(trifluoromethyl) phenyl]-9-(3-quinolinyl)-benzo[h]-1,6-naphthyridin-2(1H)-one, and has a formula of:

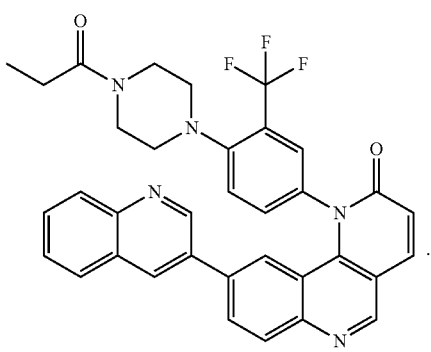 [SMILES: CCC(=O)N1CCN(c2ccc(-n3c(=O)ccc4cnc5ccc(-c6cnc7ccccc7c6)cc5c43)cc2C(F)(F)F)CC1]

Omipalisib is also known as 2,4-difluoro-N-(2-methoxy-5-(4-(pyridazin-4-yl) quinolin-6-yl)pyridin-3-yl)benzenesulfonamide, and has a formula of:

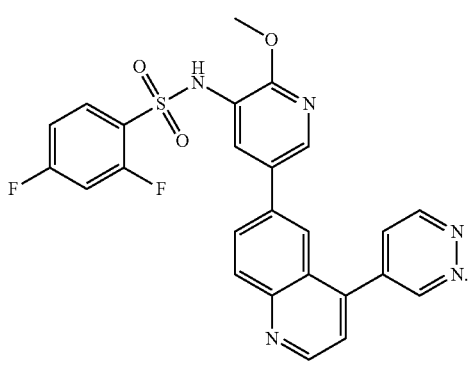 [SMILES: COc1ncc(-c2ccc3nccc(-c4ccnnc4)c3c2)cc1NS(=O)(=O)c1ccc(F)cc1F]

OSI-027 is also known as (1r,4r)-4-(4-amino-5-(7-methoxy-1H-indol-2-yl) imidazo[5,1-f][1,2,4]triazin-7-yl) cyclohexane-1-carboxylic acid, and has a formula of:

PF-04691502 is also known as 2-amino-8-((1r,4r)-4-(2-hydroxyethoxy)cyclohexyl)-6-(6-methoxypyridin-3-yl)-4-methylpyrido[2,3-d]pyrimidin-7(8H)-one and has a formula of:

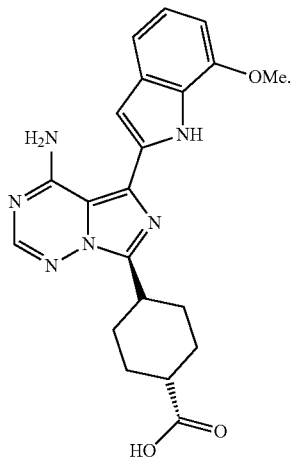

Apitolisib is also known as (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one, and has a formula of:

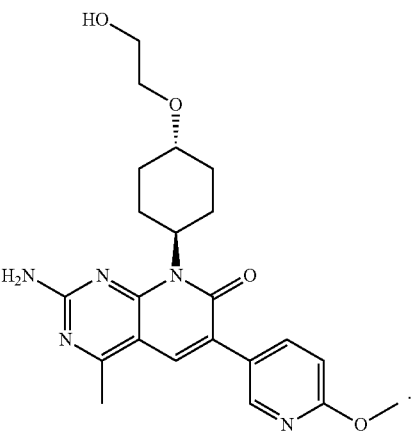 [SMILES: COc1ccc(-c2cc3c(C)nc(N)nc3n([C@H]3CC[C@H](OCCO)CC3)c2=O)cn1]

GSK1059615 is also known as (Z)-5-((4-(pyridin-4-yl)quinolin-6-yl)methylene) thiazolidine-2,4-dione, and has a formula of:

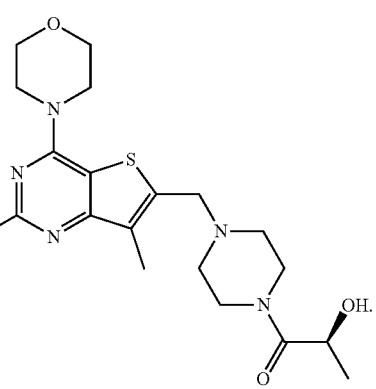

19

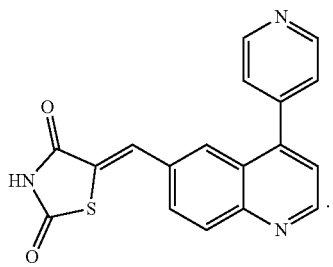 [SMILES: O=C1NC(=O)/C(=C/c2ccc3nccc(-c4ccncc4)c3c2)S1]

WYE-354 is also known as 4-[6-[4-[(methoxycarbonyl)amino]phenyl]-4-(4-morpholinyl)-1H-pyrazolo[3,4-d]pyrimidin-1-yl]-1-piperidinecarboxylic acid methyl ester, and has a formula of:

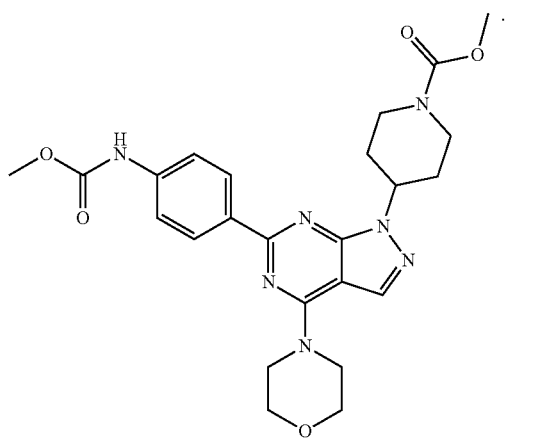

Gedatolisib is also known as 1-(4-(4-(dimethylamino)piperidine-1-carbonyl)phenyl)-3-(4-(4,6-dimorpholino-1,3,5-triazin-2-yl)phenyl)urea, and has a formula of:

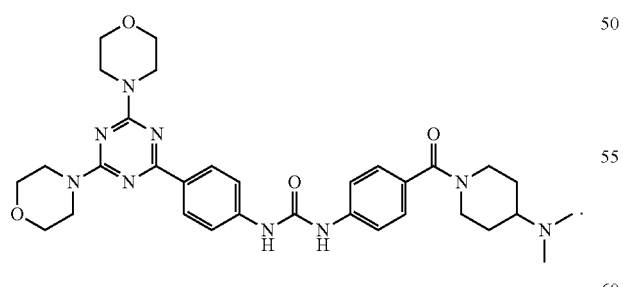

AZD-2014 is also known as 3-(2,4-bis((S)-3-methylmorpholino)pyrido[2,3-d]pyrimidin-7-yl)-N-methylbenzamide, and has a formula of:

20

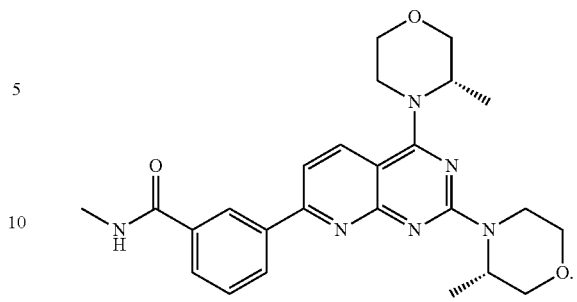

Torin-2 is also known as 9-(6-amino-3-pyridinyl)-1-[3-(trifluoromethyl)phenyl]-benzo[h]-1,6-naphthyridin-2(1H)-one, and has a formula of:

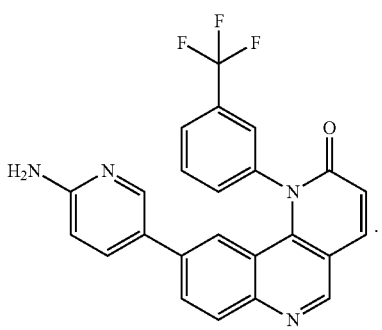 [SMILES: Nc1ccc(-c2ccc3ncc4ccc(=O)n(-c5cccc(C(F)(F)F)c5)c4c3c2)cn1]

WYE-125132 is also known as N-[4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl]-N'-methyl-urea, and has a formula of:

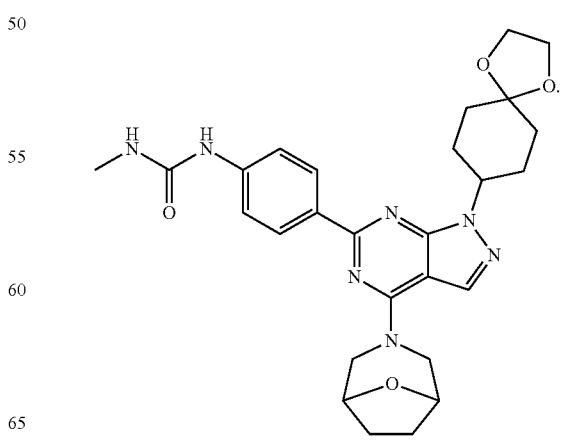

BGT226 is also known as 8-(6-methoxypyridin-3-yl)-3-methyl-1-(4-(piperazin-1-yl)-3-(trifluoromethyl)phenyl)-1H-imidazo[4,5-c]quinolin-2(3H)-one, and has a formula of:

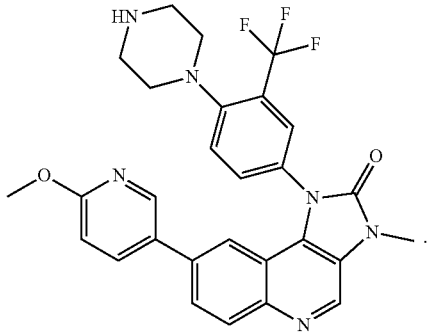

Palomid-529 is also known as 3-(4-methoxybenzyloxy)-8-(1-hydroxyethyl)-2-methoxy-6H-benzo[c]chromen-6-one, and has a formula of:

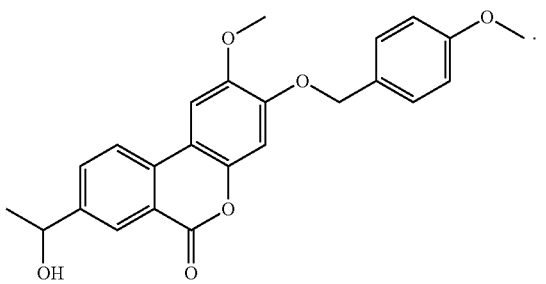 [SMILES: COc1ccc(COc2cc3oc(=O)c4cc(C(C)O)ccc4c3cc2OC)cc1]

PP121 is also known as 1-cyclopentyl-3-(1H-pyrrolo[2,3-b]pyridin-5-yl)-1H-pyrazolo[3,4-d]pyrimidin-4-amine, and has a formula of:

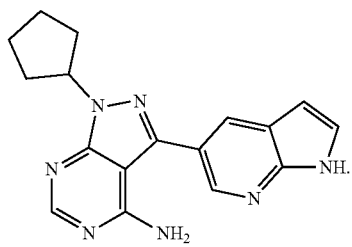 [SMILES: Nc1ncnc2c1c(-c1cnc3[nH]ccc3c1)nn2C1CCCC1]

WYE-687 is also known as methyl 4-(4-morpholino-1-(1-(pyridin-3-ylmethyl) piperidin-4-yl)-1H-pyrazolo[3,4-d]pyrimidin-6-yl)phenylcarbamate, and has a formula of:

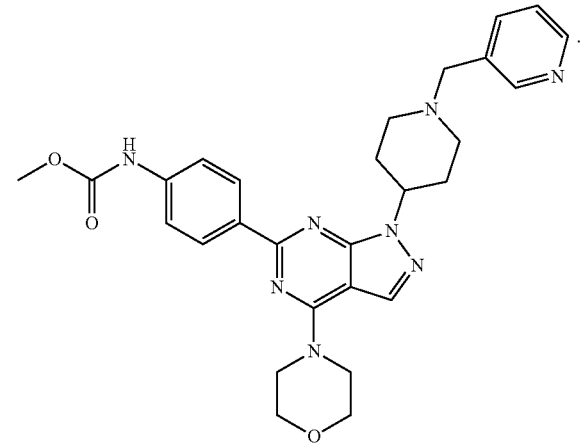 [SMILES: COC(=O)Nc1ccc(-c2nc(N3CCOCC3)c3cnn(C4CCN(Cc5cccnc5)CC4)c3n2)cc1]

CH5132799 is also known as 5-(7-(methylsulfonyl)-2-morpholino-6,7-dihydro-5H-pyrrolo[2,3-d]pyrimidin-4-yl)pyrimidin-2-amine, and has a formula of:

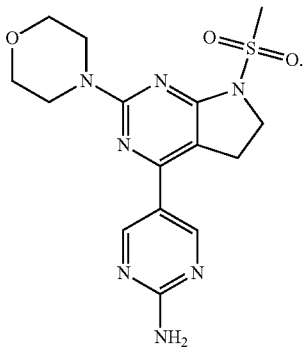 [SMILES: CS(=O)(=O)N1CCc2c(-c3cnc(N)nc3)nc(N3CCOCC3)nc21]

WAY-600 is also known as 6-(1H-indol-5-yl)-4-morpholino-1-(1-(pyridin-3-ylmeth)piperidin-4-yl)-1H-pyrazolo[3,4-d]pyrimidine, and has a formula of:

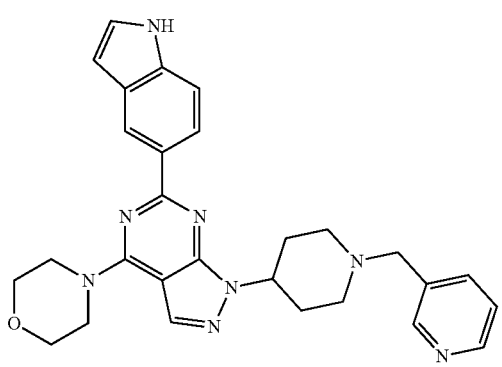 [SMILES: c1cncc(CN2CCC(n3ncc4c(N5CCOCC5)nc(-c5ccc6[nH]ccc6c5)nc43)CC2)c1]

ETP-46464 is also known as α,α-dimethyl-4-[2-oxo-9-(3-quinolinyl)-2H-[1,3]oxazino[5,4-c]quinolin-1(4H)-yl]-benzeneacetonitrile, and has a formula of:

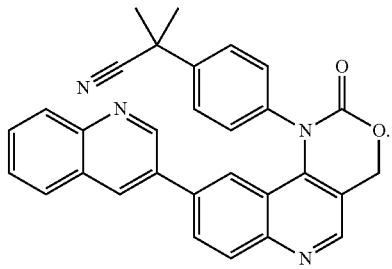 [SMILES: CC(C)(C#N)c1ccc(N2C(=O)OCc3cnc4ccc(-c5cnc6ccccc6c5)cc4c32)cc1]

GDC-0349 is also known as N-ethyl-N'-[4-[5,6,7,8-tetrahydro-4-[(3S)-3-methyl-4-morpholinyl]-7-(3-oxetanyl)pyrido[3,4-d]pyrimidin-2-yl]phenyl]-urea, and has a formula of:

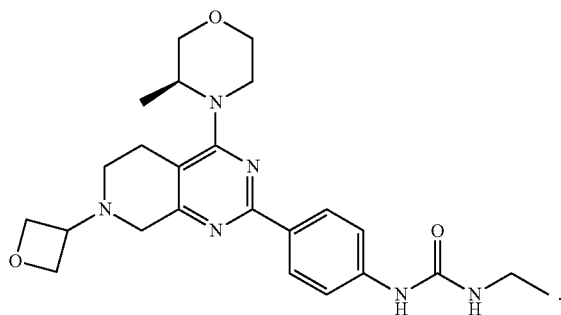 [SMILES: CCNC(=O)Nc1ccc(-c2nc3c(c(N4CCOC[C@@H]4C)n2)CCN(C2COC2)C3)cc1]

XL388 is also known as [7-(6-amino-3-pyridinyl)-2,3-dihydro-1,4-benzoxazepin-4(5H)-yl][3-fluoro-2-methyl-4-(methylsulfonyl)phenyl]-methanone, and has a formula of:

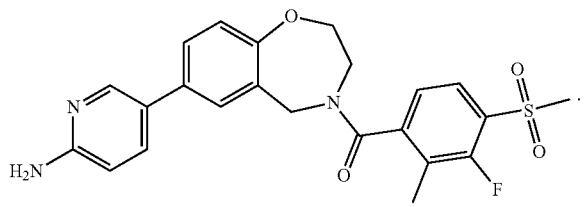 [SMILES: Cc1c(C(=O)N2CCOc3ccc(-c4ccc(N)nc4)cc3C2)ccc(S(C)(=O)=O)c1F]

Zotarolimus is also known as 42-deoxy-42-(1H-tetrazol-1-yl)-(42S)-rapamycin, and has a formula of:

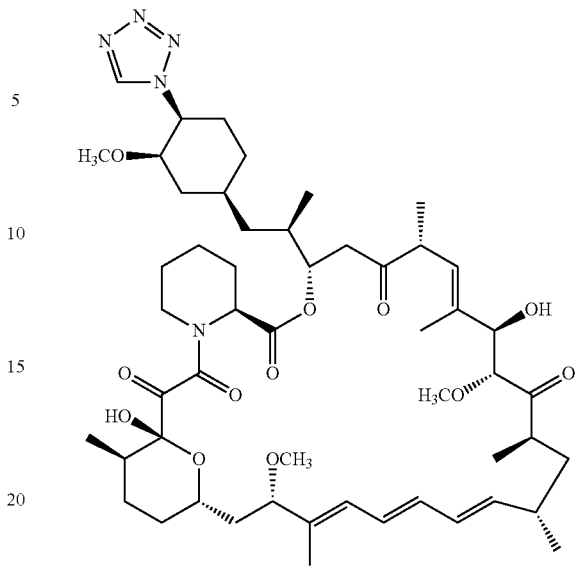

In certain embodiments, the mTORC1 inhibitor contemplated in the invention is rapamycin. In other embodiments, the mTORC1 inhibitor may be a modified form of rapamycin with improved delivery to specific intracellular compartments or organelles, such as the mitochondria, the nucleus, the lysosome, and/or the endoplasmic reticulum.

In certain embodiments, the therapeutically effective amount of a mTORC1 inhibitor in the composition ranges from about 0.001% to about 1% by weight. In other embodiments, the therapeutically effective amount by weight of the mTORC1 inhibitor in the composition ranges from about 0.002% to about 0.75%, about 0.005% to about 0.5%, about 0.008% to about 0.25%, about 0.01% to about 0.2%, about 0.02% to about 0.15%, or about 0.03% to about 0.1%.

In certain embodiments, the composition of the invention further comprises a dermatologically acceptable carrier. The compositions of the present invention may comprise from about 60% to about 99.9%, alternatively from about 70% to about 95%, and alternatively from about 80% to about 90%, of a dermatologically acceptable carrier. In certain embodiments, the dermatologically acceptable carrier is at least selected from the group consisting of solvent, lubricant, emollient, emulsifier, moisturizer, thickening wax, softener, fragrance, preservative, and artificial color(s). In other embodiments, the dermatologically acceptable carrier is at least one selected from the group consisting of water, fatty alcohols, and volatile organic alcohols. One non-limiting example of the dermatologically acceptable carrier is petrolatum.

Methods

In one aspect, the invention provides methods of increasing the lifespan of mammalian fibroblasts. In another aspect, the invention provides methods of preserving cell organization in mammalian fibroblasts. In yet another aspect, the invention provides methods of preventing or minimizing senescence in mammalian fibroblasts. In yet another aspect, the invention provides methods of treating or preventing age-related dermal disorders including dermal atrophy, pseudoscars, seborrheic or actinic keratosis, lentigines, focal areas of dermal thickening, and coarse wrinkles in a mammalian subject.

In certain embodiments, the methods of the invention comprise topically administering to the subject a therapeutically effective amount of a mTORC1 inhibitor, which is optionally formulated in a dermally acceptable composition. In other embodiments, the compositions of the invention comprises a therapeutically effective amount of a mTORC1 inhibitor. In yet other embodiments, the composition further comprises a dermatologically acceptable carrier. In yet other embodiments, the composition is applied topically to the affected skin area of the subject.

In certain embodiments, topical formulations of the compositions contemplated within the invention are used for treating dermal atrophy. In other embodiments, the invention provides a topical cream comprising a therapeutically effective amount of rapamycin for treating or preventing dermal atrophy.

In certain embodiments, dermal atrophy is evaluated by measurement of the dermal layer utilizing a calibrated digital caliper measurement of the dermal layer. In other embodiments, improvement in seborrheic keratosis, lentigines, pseudoscars, coarse wrinkles, and epidermal thickening is evaluated through an investigator evaluation rating scale of 1-4, in which 1 is normal with no sign of lesion; 2 represents minor lesions; 3 represents lesions that are distinct features relative to normal skin; and 4 represents lesions that are of high severity. In yet other embodiments, lesions can be examined visually or with the aid of image analysis software such as ImageJ, an open source image analysis software available from the National Institutes of Health. In yet other embodiments, lesions are evaluated by area measurement using manual measurement of the lesion or through analysis of images taken by investigators or research study staff.

Formulations

The relative amounts of the active ingredient, the dermatologically acceptable carrier, and any additional ingredients in a pharmaceutical composition of the invention will vary, depending upon the identity, size, and condition of the subject treated. By way of example, the composition may comprise between about 0.001% and about 1% (w/w) of a mTORC1 inhibitor. In other embodiments, the therapeutically effective amount by weight of the mTORC1 inhibitor in the composition ranges from about 0.002% to about 0.75%, about 0.005% to about 0.5%, about 0.008% to about 0.25%, about 0.01% to about 0.2%, about 0.02% to about 0.15%, or about 0.03% to about 0.1%.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

The composition of the invention can be administered to a mammal as frequently as several times daily, or it may be administered less frequently, such as once a day, once a week, once every two weeks, once a month, or even less frequently, such as once every several months or even once a year or less.

Dosing regimens for administering the compositions of the invention may be once a day or twice a day. The frequency of the application and the concentration of the active agent is dependent on the skin condition and the response of the dermis. Application can be continued to achieve the desired effect on the dermis and the frequency of application can be reduced after a satisfactory result has been obtained. In certain embodiments, the administration lasts a minimum of 2 weeks to achieve results. Applications can continue beyond the initial 2 week period to obtain continued improvement and the frequency of application can be reduced once this result has been achieved. Applications may continue over the course of years with variable levels of application based upon the relative severity of lesions at any one time.

It is understood that the amount of the composition of the invention dosed per day may be administered, in non-limiting examples, every day, every other day, every 2 days, every 3 days, every 4 days, or every 5 days. The frequency of the dose will be readily apparent to the skilled artisan and will depend upon any number of factors, such as, but not limited to, the type and severity of the disease being treated, the type and age of the animal, and so forth.

In certain embodiments, the compositions of the invention are formulated using one or more dermatologically acceptable excipients or carriers. In certain embodiments, the pharmaceutical compositions of the invention comprise a therapeutically effective amount of a mTORC1 inhibitor and a dermatologically acceptable carrier. Dermatologically acceptable carriers, which are useful, include, but are not limited to, glycerol, water, saline, ethanol and other dermatologically acceptable salt solutions such as phosphates and salts of organic acids. Examples of these and other dermatologically acceptable carriers are described in Remington's Pharmaceutical Sciences (1991. Mack Publication Co., New Jersey).

The compositions of the present invention may comprise from about 60% to about 99.9%, alternatively from about 70% to about 95%, and alternatively from about 80% to about 90%, of a dermatologically acceptable carrier. In certain embodiments, the dermatologically acceptable carrier is at least selected from the group consisting of solvent, lubricant, emollient, emulsifier, moisturizer, thickening wax, softener, fragrance, preservative, and artificial color(s). In other embodiments, the dermatologically acceptable carrier is at least one selected from the group consisting of water, fatty alcohols, and volatile organic alcohols. One non-limiting example of the dermatologically acceptable carrier is petrolatum.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for topical administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating. Preferred antioxidants for some compounds are BHT, BHA, α-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include aminopolycarboxylic acid salts (e.g. disodium ethylenediaminetetraacetic acid) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Such formulations may be applied to the skin directly or through the use of swabs, applicators, spatulas and the like, as well as in the form of transdermal patches. In certain embodiments, the patch minimizes loss of pharmaceuticals through washing, friction, scratching and/or rubbing of the skin. In other embodiments, the patch increases absorption of the pharmaceutical through the skin, while minimizing the exposure of the skin to the pharmaceutical.

Topically administrable formulations contemplated within the invention may, for example, comprise from about 0.001% to about 1% (w/w) a mTORC1 inhibitor, although the concentration of the mTORC1 inhibitor may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, U.S. Pat. No. 6,323,219).

In alternative embodiments, the topical formulation further comprises other ingredients such as adjuvants, antioxidants, chelating agents, surfactants, foaming agents, wetting agents, emulsifying agents, viscosifiers, buffering agents, preservatives, and the like. In other embodiments, a permeation or penetration enhancer is included in the formulation and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the topical formulation may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

Additional non-active ingredients in the topical formulation are well known in the art. These ingredients include, but are not limited to, humectants, emollients, pH stabilizing agents, chelating agents, gelling agents, thickening agents, emulsifiers, binders, buffers, carriers, anti-oxidants, etc. Additional examples of such ingredients are included in the U.S. Food & Drug Administration, Inactive Ingredients for Approved Drugs, available online. Addition discussion and potential non-active ingredients that may be included in formulations can be found in "The Science and Practice of Pharmacy", 21st Edition. Lippincott Williams & Wilkins, Philadelphia, Pa. (2006).

In certain embodiments, a gel formulation of the invention comprises about 0.001% to about 1% (w/w) of a mTORC1 inhibitor, about 20-50% (w/w) dimethyl sulfoxide (DMSO), about 10-20% (w/w) polypropylene glycol, about 10-40% (w/w) polyethylene glycol (PEG) with a molecular weight from 100-800 (PEG100-PEG800), about 1-2% (w/w) gelling agents, and about 0-50% Water.

In other embodiments, a gel formulation of the invention comprises about 0.001% to about 1% (w/w) of rapamycin, about 20-50% (w/w) dimethyl sulfoxide (DMSO), about 10-20% (w/w) polypropylene glycol, about 10-40% (w/w) polyethylene glycol (PEG) with a molecular weight from 100-800 (PEG100-PEG800), about 1-2% (w/w) gelling agents, and about 0-50% Water.

In yet other embodiments, a solution or spray formulation of the invention comprises about 0.001% to about 1% (w/w) of a mTORC1 inhibitor in an aqueous solution having about 10-50% (w/w) of DMSO and about 10-50% (w/w) of PEG.

In yet other embodiments, a solution or spray formulation of the invention comprises about 0.001% to about 1% (w/w) of rapamycin in an aqueous solution having about 10-50% (w/w) of DMSO and about 10-50% (w/w) of PEG.

In yet other embodiments, a cream or lotion formulation of the invention comprises about 0.001% to about 1% (w/w) of a mTORC1 inhibitor, mineral oil, any type of alcohol, a non-ionic detergent such as Triton X-100, emulsifying wax, glycerol monostearate (GMS), isopropyl myristate (IPM), and about 60-80% water.

In yet other embodiments, a cream or lotion formulation of the invention comprises about 0.001% to about 1% (w/w) of rapamycin, mineral oil, any type of alcohol, a non-ionic detergent such as Triton X-100, emulsifying wax, glycerol monostearate (GMS), isopropyl myristate (IPM), and about 60-80% water.

In yet other embodiments, an ointment formulation of the invention comprises about 0.001% to about 1% (w/w) of a mTORC1 inhibitor in an aqueous solution having about 10-50% (w/w) of DMSO and about 10-50% (w/w) of PEG and about 1-60% (w/w) petrolatum.

In yet other embodiments, an ointment formulation of the invention comprises about 0.001% to about 1% (w/w) of rapamycin in an aqueous solution having about 10-50% (w/w) of DMSO and about 10-50% (w/w) of PEG and about 1-60% (w/w) petrolatum.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for topical administration, such as liniments, lotions, oil-in-water or water-in-oil emulsions such as creams, ointments or pastes, transdermal patches, and solutions or suspensions that are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material which provides sustained release properties to the compounds.

In certain embodiments of the invention, the compositions of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Unless otherwise noted, all cell lines, starting materials, reagents and cell lines were obtained from commercial suppliers and used without further manipulation.

Cell Culture and Cell Culture Reagents

Cell culture experiments utilizing NRTIs were of the following design. Cultures of either human lung or cardiac fibroblasts were cultivated according to standard culture protocols for these cells (Cristofalo, et al., Journal of Tissue Culture Methods 1980, 6:117-121). Parallel sets of cultures were maintained in normal growth media or in normal growth media with the addition of 1 nM rapamycin. Cultures were maintained with 1 nM rapamycin (Enzo Biologicals) for two weeks before exposure to NRTIs. Cell cultures were exposed to NRTIs at indicated concentrations in individual experiments (generally 10-20 µg/ml) for 7 days, with a change of media and fresh NRTIs at day 4. Mitochondrial measurements, bioanalyzer measurements, immunoblotting for protein expression and phosphorylation status, and assays for senescence were performed at the end of this 7-day period.

Cell culture reagents were from Cellgro, unless indicated. WI-38 fetal-lung primary human fibroblasts or human cardiac fibroblasts were grown in MEM supplemented with 10% fetal bovine serum, 1% L-glutamine, MEM vitamins, and MEM non-essential amino acids. Cells were maintained in a 37° C. in 5% $CO_2$ incubator. For treatment studies, cells were treated with 1 nM rapamycin (Enzo Biologicals) for two weeks before treatment with NRTIs. Cells were maintained by trypsinization and reseeding at a cell density of $1 \times 10^4/cm^2$ every 7 to 10 days. Emtricitabine (FTC) and tenofovir disoproxil fumarate (TDF) were kindly provided by the NIH AIDS Research & Reference Reagent program. During the 7-day exposure to the NRTIs, the pharmacologic inhibitors PD98059 (10 µM, Santa Cruz Biotechnologies), BI-D1870, GW5074, and SB203580 (10 µM, Enzo Biologicals) were added to the culture medium either during the final 48 hours or for the final 2 hours depending upon the experiment. During the 7-day exposure to NRTIs, Trolox (500 µM) and N-acetylcysteine (100 µM, Acros Organics) were added every other day. Mito-Q (20 nM) and TPP (20 nM) were kindly provided by Dr. Brett Kaufmann at the University of Pennsylvania School of Veterinary Medicine. Vector and mt-catalase adenoviruses (MOI's 25, 50, and 75) were purchased from Gene Transfer Vector Core from the University of Iowa.

Western Blotting and Co-Immunoprecipitation

Cell protein extracts were prepared by extracting with radioimmunoprecipitation assay (RIPA) buffer containing a protease inhibitor cocktail (Sigma-Aldrich) and phosphatase inhibitors, NaF and sodium orthovanadate. Protein concentration was quantified using a bicinchoninic acid (BCA) assay (Pierce Biotechnology). Western blot analysis was performed using 15 to 30 µg of protein extracts that were run on SDS-PAGE and transferred onto nitrocellulose (Biorad) membranes. Blots were incubated with antibodies specific for: beta-actin (Sigma-Aldrich), TFAm, parkin, p16, phospho(S82)HSP27, HSP27 (Santa Cruz Biotechnologies), p53, 21, catalase, MDM2 (EMD Millipore), VDAC, phospho (S235/236)-ribosomal protein S6, ribosomal protein S6, phospho(S166)-MDM2, phospho(S473)-AKT, AKT, beta-tubulin (Cell Signaling), p62 (Enzo Biologicals), IL-6 (Neo-Biolab), lamin B1, PINK 1, and Mitoprofile Total OXPHOS Cocktail (complex I-NDUFB8 subunit, CII-SDHB subunit, CIIIUQCRC2 subunit, and CIV-mitochondrial COX1 subunit) (Abcam) according to manufacturers' instructions. Western blots were visualized using IRDye 680 and 800 LI-COR secondary antibodies on a LI-COR Odyssey using LI-COR Odyssey software version 3.0 (LI-COR Biosciences). For co-immunoprecipitation, cell protein extracts were prepared in HNTG buffer containing a protease inhibitor cocktail and quantified using BCA assay. Protein extracts at the concentration of 0.5 mg were pre-cleared with protein A/G beads (Santa Cruz Biologicals) for 30 minutes. After centrifugation at 2,000 rpm for 5 minutes at 4° C. the supernatant was incubated with the primary antibody at manufacturer's recommended concentration overnight at 4° C. An IgG antibody (Cell Signaling) was used as a nonspecific control. Immunocomplexes were precipitated using 100 µl of protein A/G beads overnight at 4° C. Immunocomplexes bound to the beads were centrifuged at 2000 rpm for 5 minutes at 4° C. and washed three times using HNTG buffer. Following the addition of 2× sample buffer and boiling at 100° C., protein samples were used for western blotting.

Total ROS, Mitochondrial Membrane Potential, Mitochondrial Mass, and Superoxide Anion Assessments Mitochondrial membrane potential was detected by incubating cells with 25 nM TMRE (Molecular Probes). Mitochondrial mass was evaluated by incubating the cells with 100 nM Mitotracker Green FM (Molecular Probes). Mitochondrial superoxide anion levels were detected by incubating the cells with 5 µM MitoSox Red (Molecular Probes). Total cellular levels of ROS were detected by incubating the cells with 10 µM 2',7'-dichlorofluoroscein diacetate (DCF-DA; Sigma-Aldrich) in 1% fetal bovine serum supplemented MEM and washing twice with Krebs Ringer phosphate glucose buffer (145 mM NaCl, 5.7 mM $NaH_2PO_4$, 4.86 mM KCL, 0.54 mM $CaCl_2$, 1.22 mM $MgSO_4$, and 5.5 mM glucose) following the incubation period. For the aforementioned assessments, incubation was performed at 37° C. in 5% $CO_2$ for 30 minutes and cells were harvested in 2.5% trypsin-EDTA with serum-containing medium. Cells were immediately analyzed with a Guava EasyCyte Mini employing the Guava Express Plus program (Guava Technologies).

Mitochondrial Respiration Measurements

Mitochondrial function was measured using the XF cell mito stress test kit on a Seahorse XF24 Bioanalyzer (Seahorse Bioscience). Cells were seeded at a density of 15,000 cells per well in an XF24 microplate. Following acquisition, results were normalized based upon $10^6$ cells counted using a Guava EasyCyte Mini (Millipore), where applicable. Plates were loaded into the Bioanalyzer that had been pre-loaded with the sensor cartridge containing oligomycin, carbonyl cyanide p-triflouromethoxyphenylhydrazone (FCCP), and rotenone/antimycin A. Oxygen consumption was measured in triplicate prior to and following sequential addition of oligomycin, FCCP, and rotenone/antimycin A. Respiration rates and proton leak were assessed as outlined in published methods (Hill, et al., Biological chemistry 2012, 393:1485-1512). Mitochondrial respiration was calculated based upon oxygen consumption rate measurements in triplicates from cells seeded in at least quadruplicates. Basal respiration represents the initial oxygen consumption rate measurements and maximal respiration represents the oxygen consumption rate measurements following FCCP addition. ATP-linked respiration is represented as the oligomycin-sensitive oxygen change to basal oxygen consumption rate. Proton leak represents the oligomycin insensitive oxygen consumption rate. Non-mitochondrial sources of oxygen consumption were subtracted by normalizing to the rotenone/antimycin A-insensitive oxygen consumption rate measurements. All data was normalized to cell number by counting cells in each well at the completion of the mitochondrial assessments.

Senescence Associated Beta Galactosidase Detection

Assessment of SA-β-gal activity was performed by plating cells following respective treatments at low density ($0.5 \times 10^4/cm^2$) to prevent false positive staining known to occur in high density cultures. Seeding was performed for SA-β-gal staining following NRTI treatment for one week and staining was performed 24 hours following seeding. Cells were washed with PBS, fixed with 2% formaldehyde-0.2% glutaraldehyde for 5 minutes at room temperature, washed with PBS once more, and incubated overnight at 37° C. in a staining solution containing 50 mg/ml X-gal, 100 mM potassium ferricyanide, 100 mM potassium ferrocyanide, 5 M NaCl, 1 M $MgCl_2$, and 0.2 M citric acid/phosphate buffer (pH 6.0). Following incubation, cells were washed three times with PBS and at least 500 cells were counted for each sample in triplicates. Positive cells (blue cells) were expressed as a percentage of total cells.

Immunofluorescence

Cells were seeded onto acid-washed coverslips at standard density following the designated treatment. Following 24 hours, cells were fixed using 4% paraformaldehyde, permeabilized using 0.1% Triton-PBS, and blocked with applicable animal serum. Immunofluorescence was performed to visualize the mitochondria using a cytochrome C antibody (EMD Millipore) and co-stained with a FRAP antibody (Santa Cruz). Mitochondria were also visualized using lentiviral transduction of a mitochondrial tagged GFP (Vector Core, University of Pittsburgh) and selected using puromycin. Following applicable experimental treatment, immunofluorescence was performed on mitochondrial-expressing cells using a Raptor antibody (Bethyl Laboratories). Following primary antibody incubation, staining was performed using Alexa-Flour Secondaries (LICOR Biosciences) and DAPI as a nuclear stain (10 ng/ml) and preserved with VectaShield mounting media (Fisher Scientific). Cells were imaged using deconvolution or confocal microscopy for co-localization event quantification.

Statistical Analysis

Results are representative of at least three independent experiments and statistical significance was determined using an unpaired two-tailed Student's t-test. Data sets were subjected to normality tests to verify normal distribution of data. One-way Anova with Bonferroni post-hoc analysis was performed on multiple comparison groups involving control, NRTI, rapamycin, and rapamycin NRTI where appropriate.

Formulations

An exemplary non-limiting emulsion formulation of the invention (referred to as "Formulation R" hereinafter) comprises about 0.001% to about 1% (w/w) of rapamycin, palmitate at about 4-6%, glycerin at about 6-8%, and the balance consisting of water.

Administration to Patients

Patients presenting to a physician with a diagnosis of dermal atrophy, seborrheic keratosis, actinic keratosis, lentigines, senile pseudoscars, or coarse wrinkles were selected for administration of a composition of the invention. Dermal thickness was quantified using a Mitoutoyo digital caliper with certified accuracy to 0.001 mm. Lesions (actinic keratosis, psuedoscars, coarse wrinkles, were evaluated utilizing the Investigator evaluation rating scale for severity. Formulation R was provided to the patient with instruction for administration 1-2 times per day for an initial 2-week period. Patients were advised to cease application of Formulation R at any sign of adverse reaction in the area of application. Following the 2-week application period, dermal thickness and lesion severity was monitored on a weekly basis.

Figure 1B:
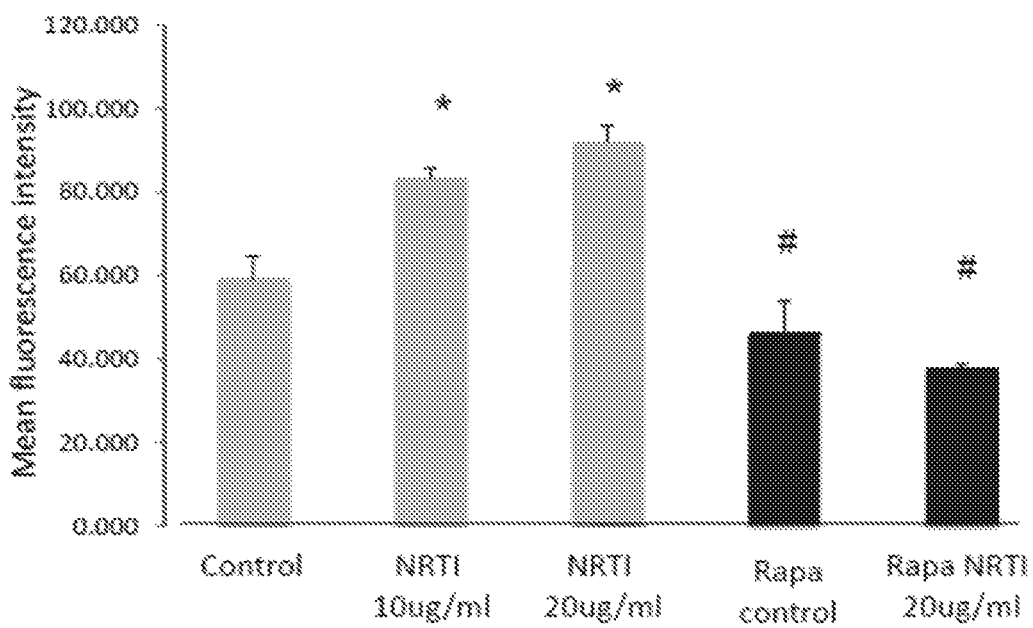
Figure 1C:
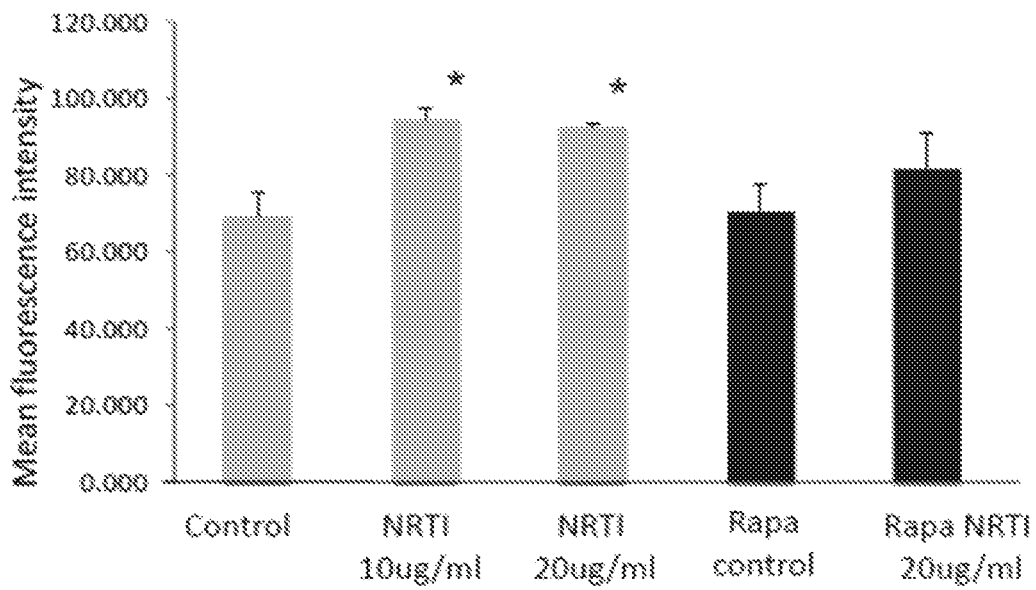
Figure 1D:
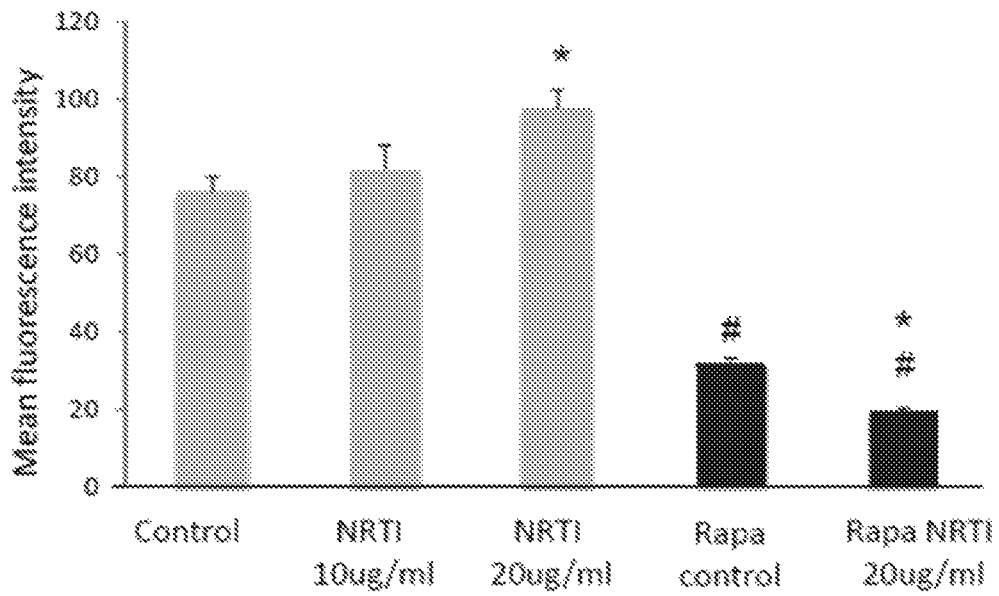
Figure 1E:
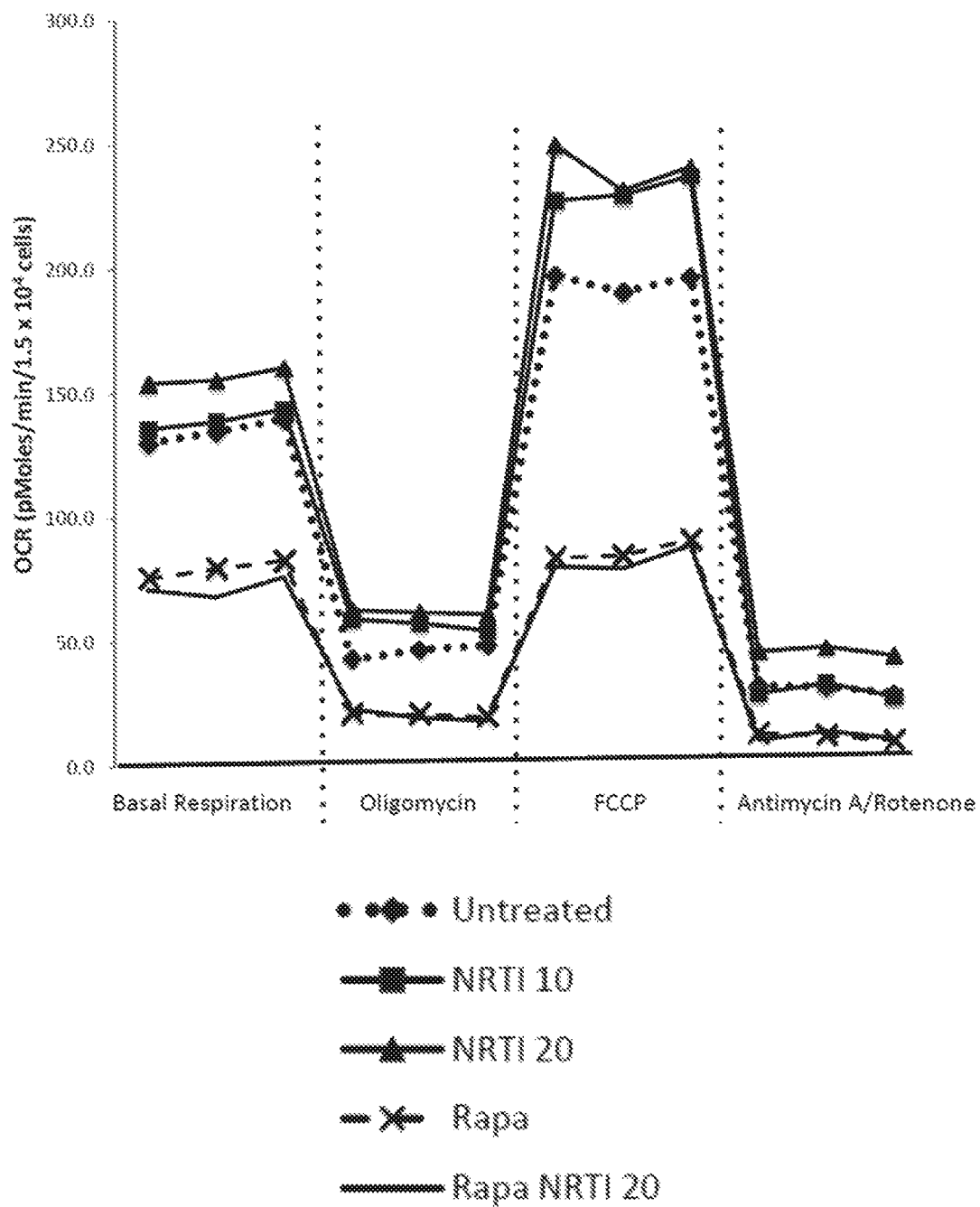

Example 1: Mitochondrial Effects of Nucleoside/Nucleotide Analogs are Relieved by Rapamycin The effects of combination treatment with TDF and FTC (referred to as NRTIs for simplicity) were examined at concentrations relevant to serum levels in patients receiving anti-retroviral therapy, on mitochondria in both human cardiac and lung fibroblasts. Parallel cultures were grown in the additional presence of 1 nM rapamycin. This concentration of rapamycin was found to extend replicative lifespan and improve the mitochondrial profile of human fibroblasts. Exposure to NRTIs for 7 days produced a significant increase in mitochondrial membrane potential, mitochondrial ROS production, and mitochondrial mass in the human cardiac fibroblasts (FIGS. 1A-1C). Similar results were observed in the human lung fibroblasts. Additionally, total cellular ROS increased significantly following exposure to NRTIs in both fibroblast populations (FIG. 1D). Cultures grown in the presence of rapamycin did not exhibit the same level of increase in mitochondrial membrane potential, mitochondrial ROS, or total cellular ROS following exposure to NRTIs.

Figure 1F:
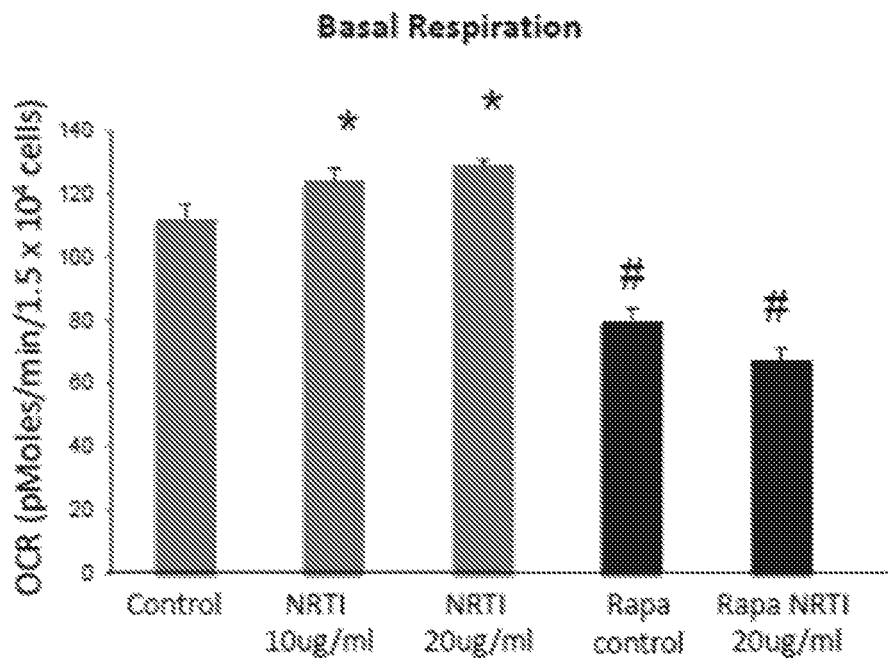
Figure 1G:
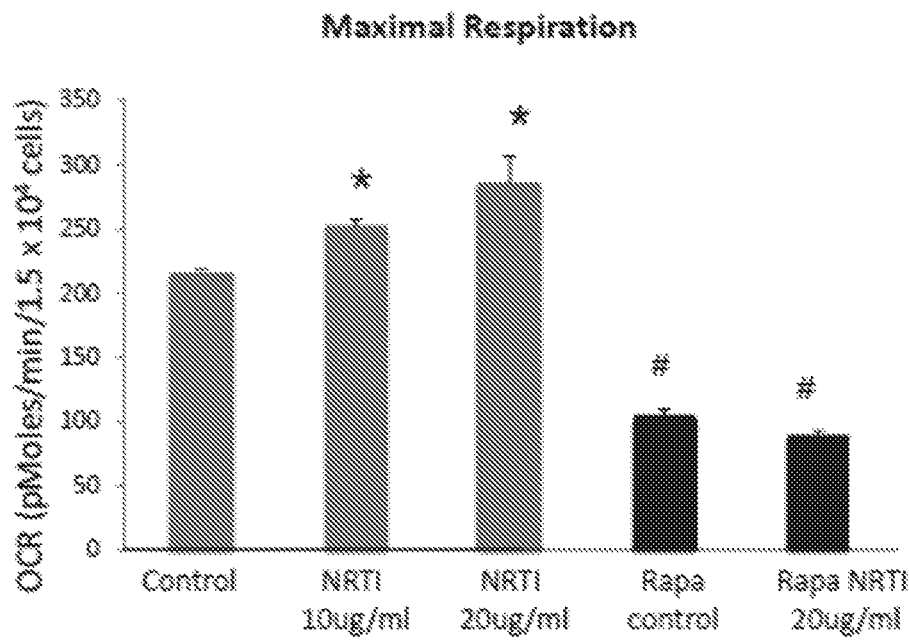
Figure 1H:
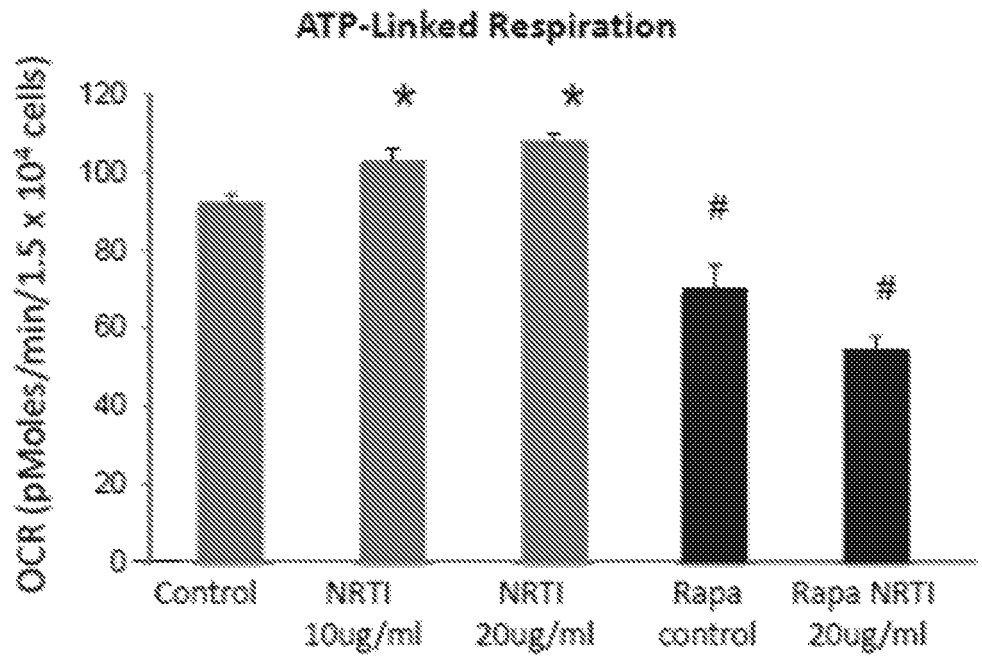
Figure 1I:
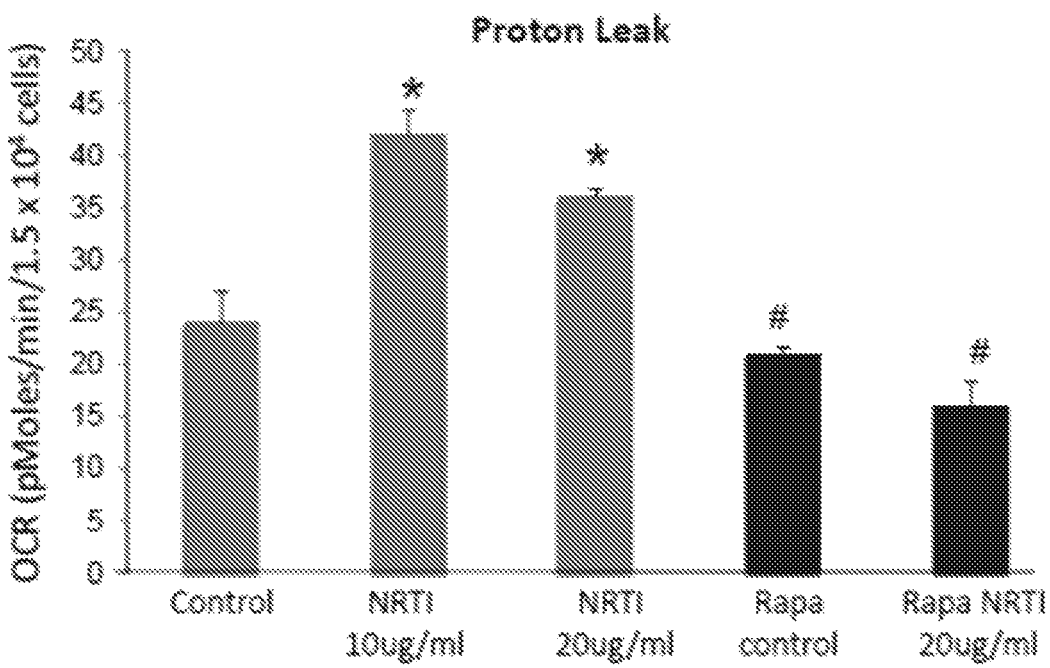

An indirect assessment of mitochondrial activity was performed using a Seahorse Bioanalyzer using cultures maintained in standard culture medium or maintained in the presence of rapamycin. The calculated rates of basal respiration, maximal respiration, ATP-linked respiration, and proton leak increased significantly when human cardiac fibroblasts were exposed to NRTIs (FIGS. 1E-1I). Rapamycin-treated cells had significantly lower basal respiration and did not exhibit an increase in basal or maximal respiration when exposed to NRTIs (FIGS. 1F-1G). ATP-linked respiration was increased by NRTI exposure and was reduced in rapamycin-treated cultures (FIG. 1H). In addition, the rapamycin-treated cells did not exhibit an increase in proton leak following exposure to NRTIs (FIG. 1I). Human lung fibroblasts gave similar results when subjected to the same analyses (i.e., basal and maximal respiration increased significantly, as did proton leak in cells treated with NRTIs). Similar to the cardiac fibroblasts, rapamycin-treated lung fibroblasts exhibited no increase in these parameters following exposure to NRTIs.

Figure 2A:
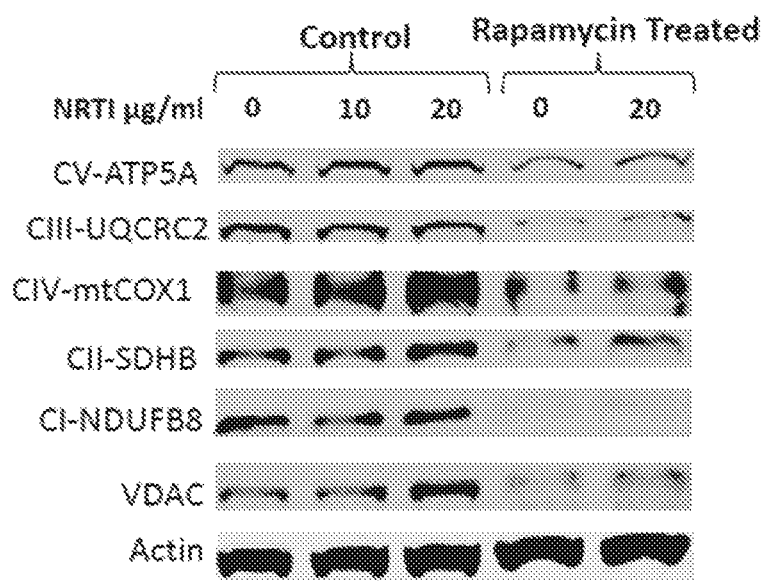
FIGS. 2A-2H illustrate steady state levels of electron transport chain subunits and mitochondrial proteins.

Example 2: Alterations in Electron Transport Chain Components in Response to Nucleoside/Nucleotide Analogs and Rapamycin The effect of NRTI exposure on steady state levels of a subset of electron transport chain proteins was examined. Levels of NADH dehydrogenase (ubiquinone) 1 beta subcomplex, 8 (NDUFB8) of complex I, succinate dehydrogenase (ubiquinone) ironsulfur subunit (SDHB) of complex II, ubiquinol-cytochrome c reductase core protein II (UQCRC2) of complex III, and cytochrome c oxidase subunit I (mt-CO1) of complex IV all increased following exposure to NRTIs (FIG. 2A). Similarly, the steady state level of the outer membrane voltage dependent channel (VDAC) increased in cells exposed to NRTIs while in contrast, steady state levels of the ATP synthase alpha subunit 1 (ATP5A) were unchanged (FIG. 2A).

Cells treated with rapamycin expressed lower steady state levels of NDUFB8, SDHB, UQCRC2, and mt-CO1, while levels of ATP5A were similar to control cells. In addition, ETC protein levels were not elevated when rapamycin-treated cells were exposed to NRTIs (FIG. 2A).

Figure 2B:
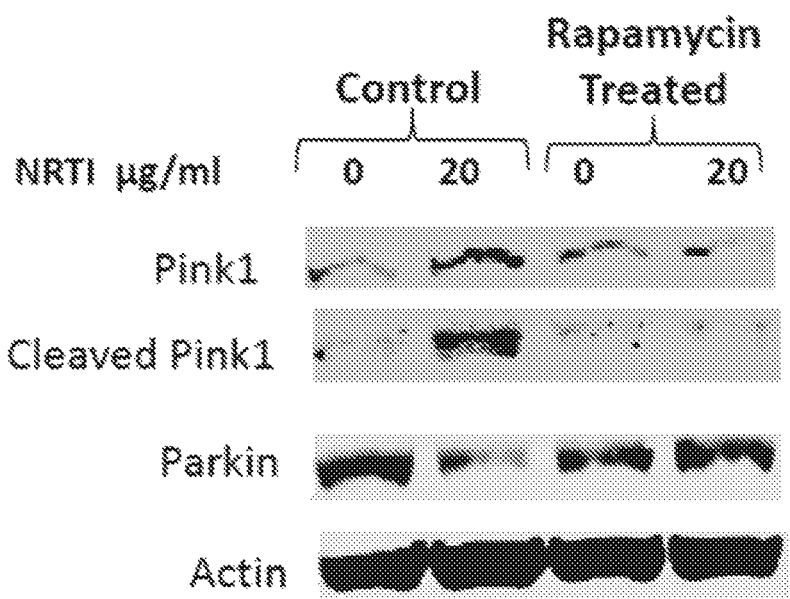
Figure 2C:
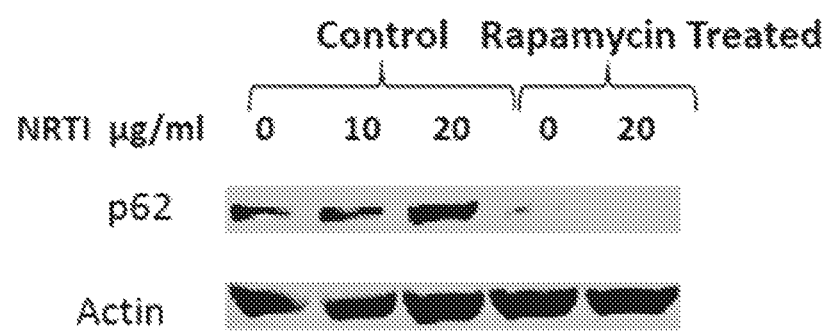
Figure 2D:
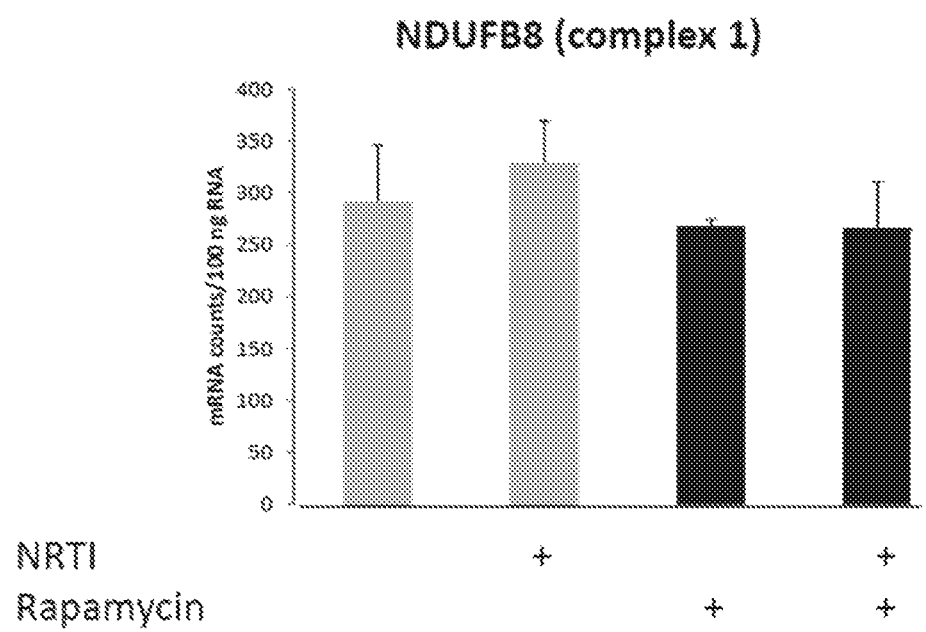
Figure 2E:
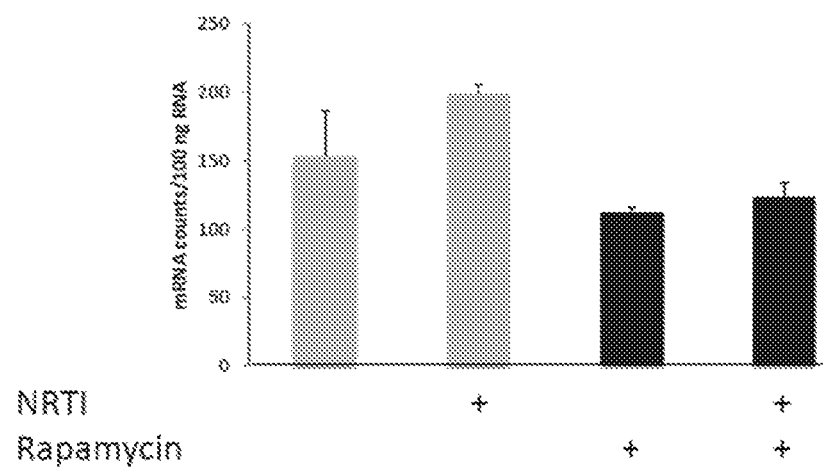
Figure 2F:
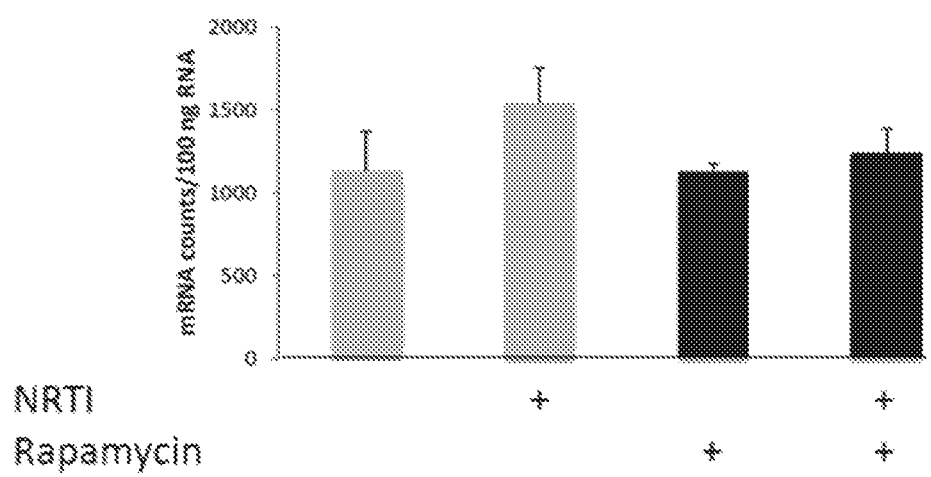
Figure 2G:
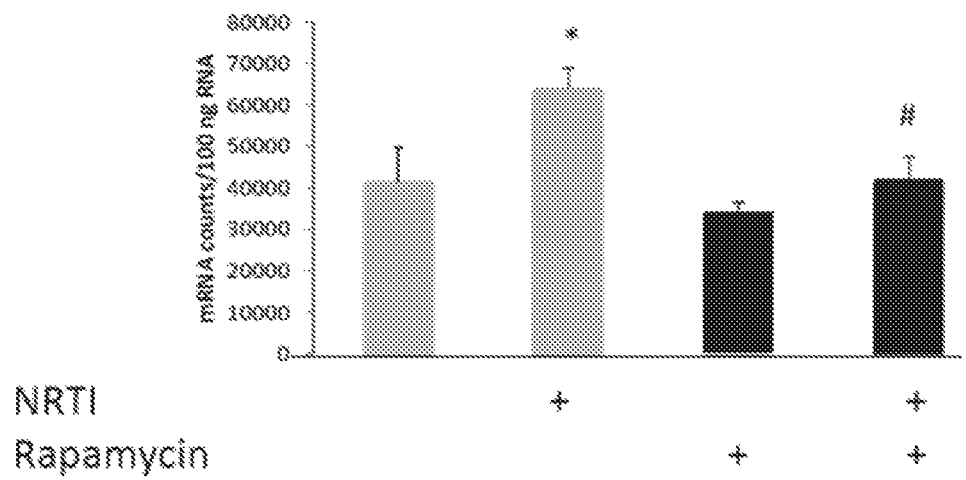
Figure 2H:
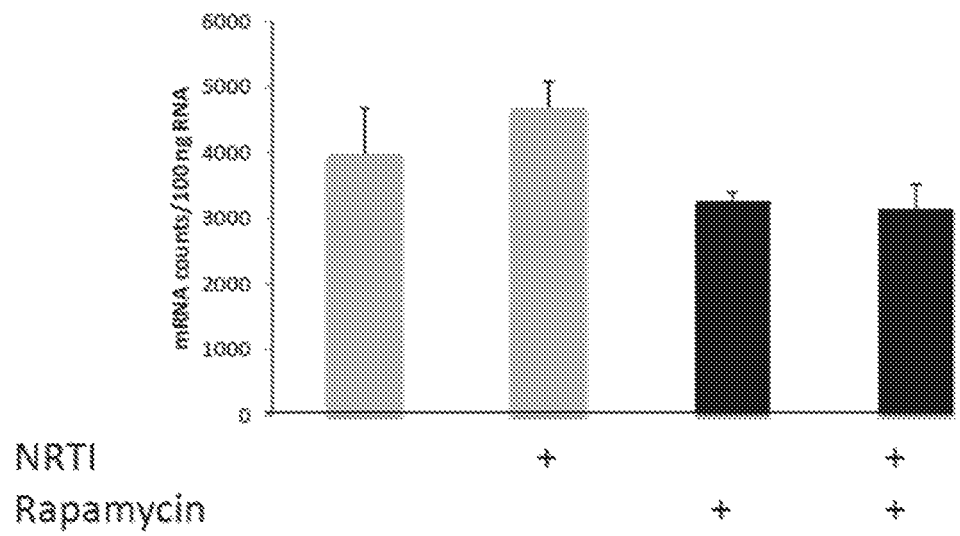

Levels of proteins involved in mitochondrial clearance, Pink 1 and Parkin, were also examined (FIG. 2B). Exposure to NRTIs caused an increase in Pink and the cleaved form of Pink 1, as well as a decrease in Parkin. The level of the autophagy cargo loading protein p62/SQSTM1 increased in response to NRTIs, but decreased in response to rapamycin (FIG. 2C).

Differences in mitochondria-related gene expression was examined using a nanostring approach which allows multiplex evaluation of mRNA species in the absence of amplification and provides a direct count of mRNA molecules. The mRNA levels paralleled the changes observed in protein levels as mRNA levels for all subunits increased in cells exposed to NRTIs while rapamycin decreased mRNA levels for all subunits (FIGS. 2D-2H).

Figure 3A:
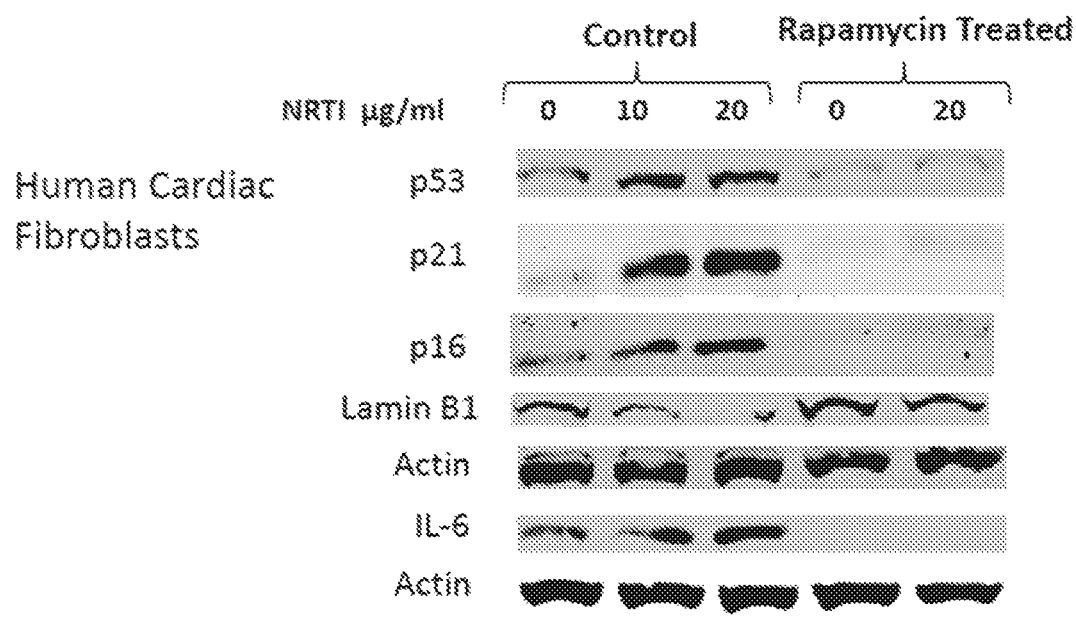
FIGS. 3A-3F illustrate the finding that NRTI exposure induces the senescence response, which is prevented by rapamycin. Human cardiac fibroblasts were maintained with or without rapamycin (1 nM) following exposure to NRTIs for 7 days. Markers of senescence were examined.
Figure 3B:
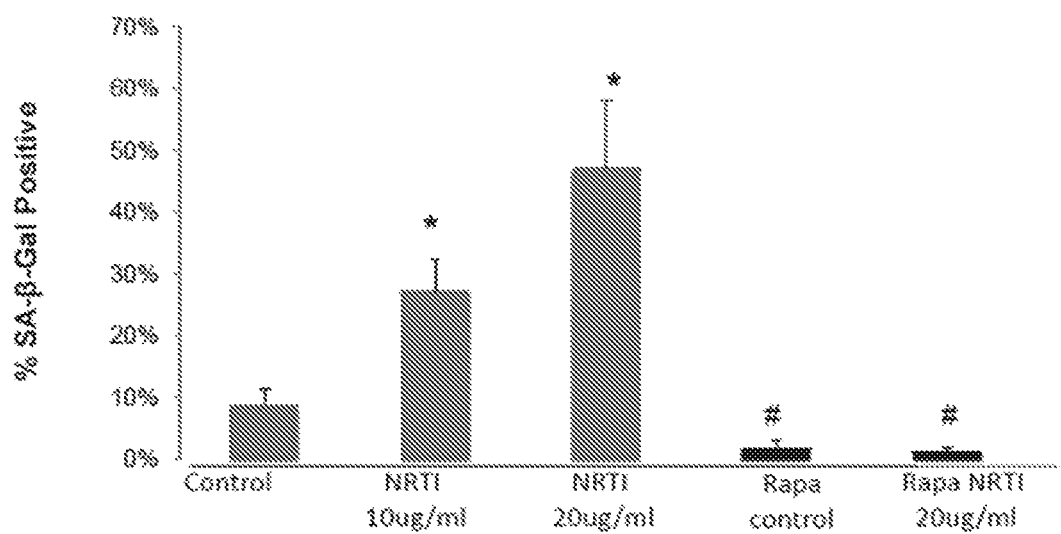
Figure 3C:
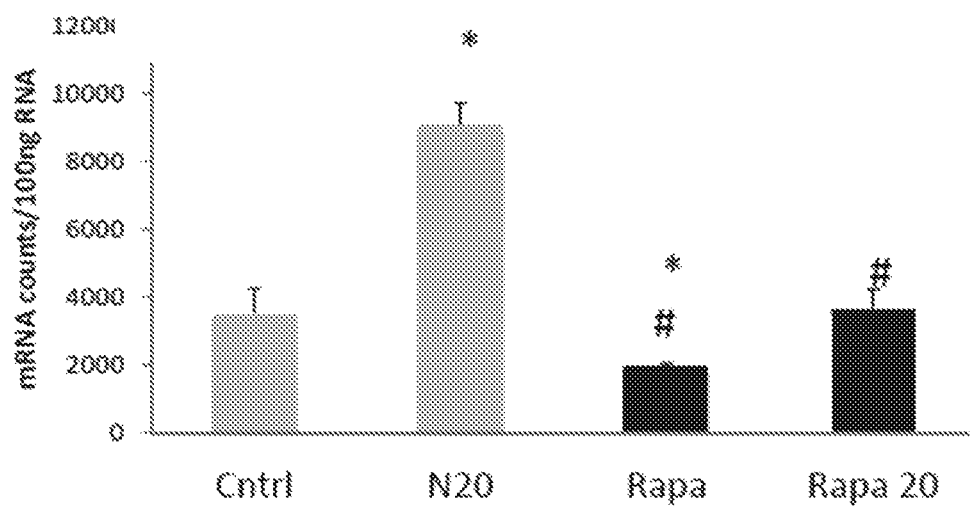
Figure 3D:
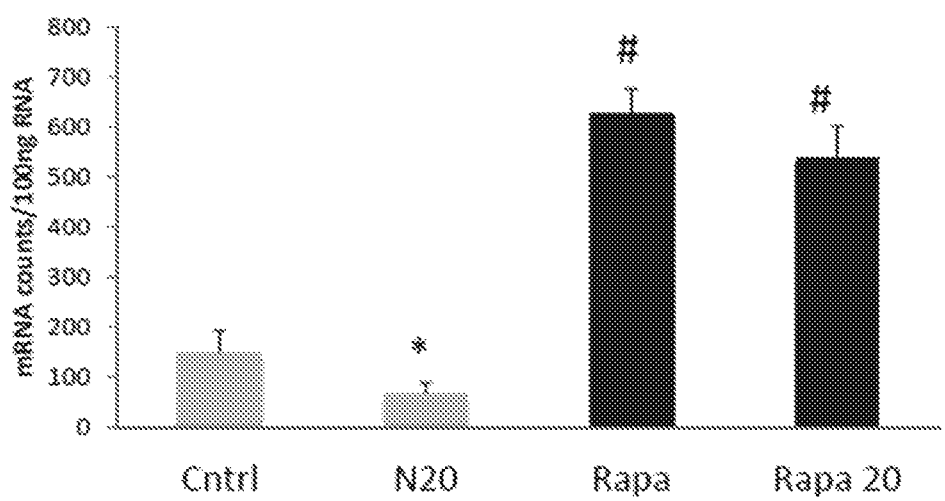
Figure 3E:
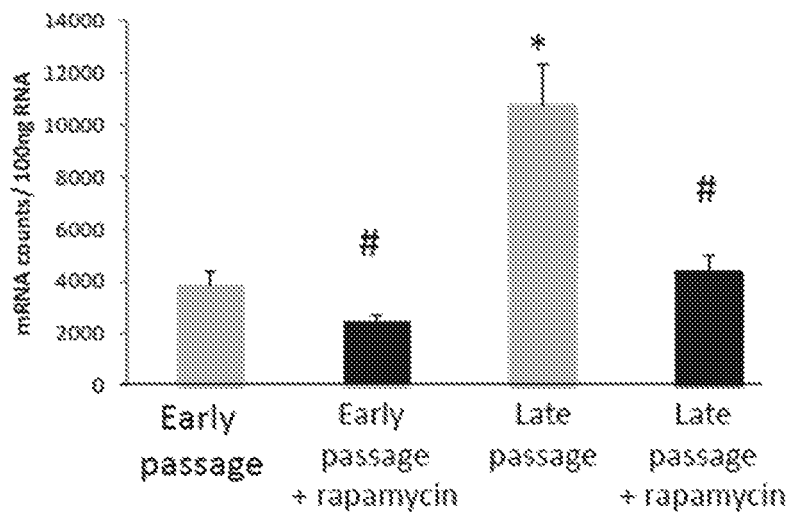
Figure 3F:
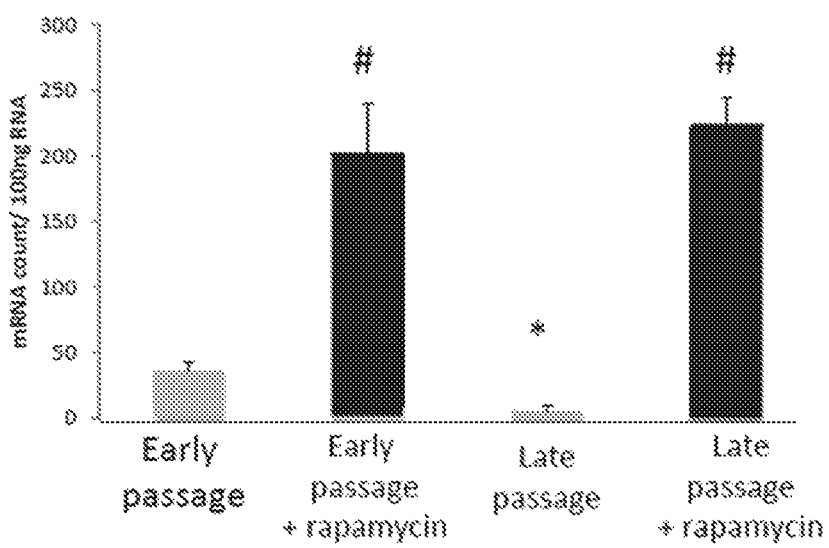

Example 3: Senescence Response to Mitochondrial Dysfunction and Protection by Rapamycin Molecular markers of the senescence program were examined following exposure to NRTIs (FIGS. 3A-3F). Levels of p53, p21, and p16 increased in fibroblasts exposed to NRTIs, while in rapamycin treated cells the levels of these senescence associated proteins did not increase (FIG. 3A). In addition, levels of lamin B1, which is known to decrease during senescence, decreased in cells exposed to NRTIs. Rapamycin prevented this decrease (FIG. 3A). Additionally, intracellular levels of IL-6, which is a component of the senescence associated secretory program, increased following exposure to NRTIs. Consistent with a block in the senescence program, rapamycin treated cells showed no increase in the levels of IL-6 following exposure to NRTIs (FIG. 3A). The percentage of the cell population expressing the senescence marker, senescence associated β-galactosidase (SA-β-gal) following exposure to NRTIs was examined. A dose dependent increase in the percent of cardiac fibroblasts expressing SA-β-gal was observed (9% in control cells compared to 28% and 48% in cells exposed to 10 or 20 ug/ml of NRITs respectively, FIG. 3B). In contrast, rapamycin treated cultures showed no increase in SA-β-gal (FIG. 3B). Analysis of mRNA levels for p21 and lamin B1 by nanostring revealed that steady state mRNA levels varied in parallel with protein levels, p21 mRNA significantly increased in response to NRTIs while lamin B1 mRNA levels significantly decreased (FIGS. 3C-3D), which was similar to the effect on the expression of p21 and lamin B1 during replicative senescence (FIGS. 3E-3F).

Lung fibroblasts showed identical changes in response to NRTIs in terms of senescence markers and the protection afforded by rapamycin treatment. There was no reduction in viability of cells exposed to NRTIs as judged by vital dye exclusion assay under any of the conditions tested and no apparent markers of apoptosis, such as caspase cleavage. Alkaline comet assay showed no evidence of increased DNA damage, indicating that the response to NRTIs was primarily a growth inhibition and not due to DNA damage. The interaction between p53 and its key regulator, MDM2, was also examined following NRTI exposure. Exposure to NRTIs reduced the association between p53 and MDM2 and increased MDM2 phosphorylation at serine 166. In addition, the use of a proteasome inhibitor revealed high molecular weight forms of p53 that were prominent in rapamycin-treated cultures but reduced following NRTI exposure.

Figure 4A:
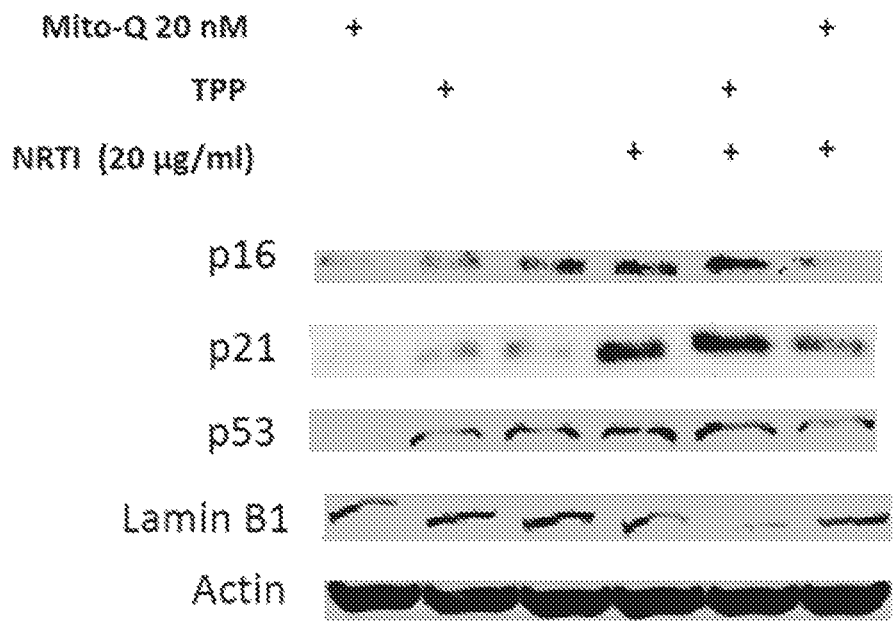
FIGS. 4A-4E illustrate the finding that ROS scavengers prevent expression of senescence markers in cells exposed to NRTIs. Human cardiac fibroblasts were treated with the mitochondrial ROS scavenger mito-Q during exposure to NRTIs.
Figure 4B:
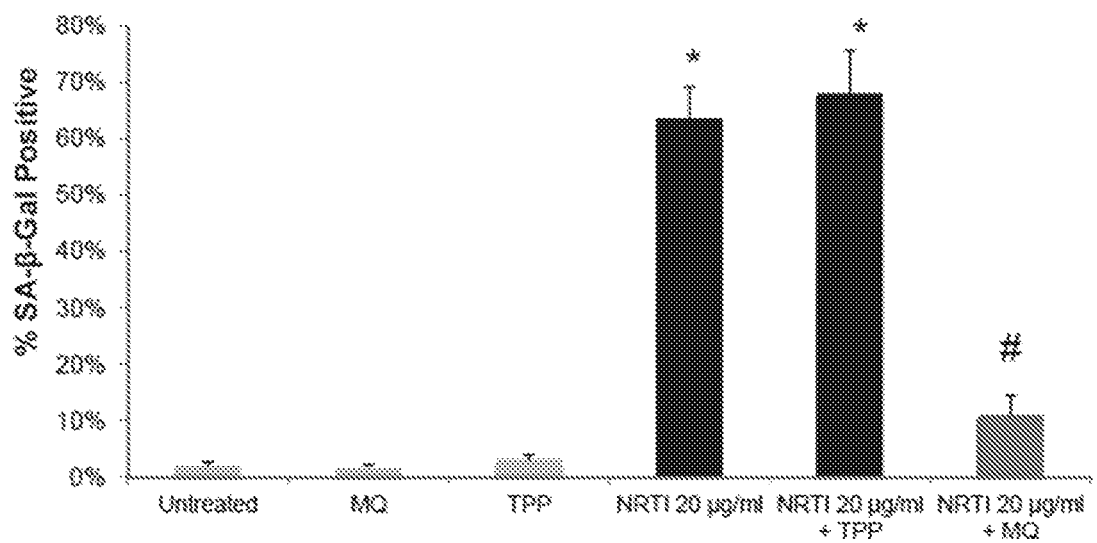
Figure 4C:
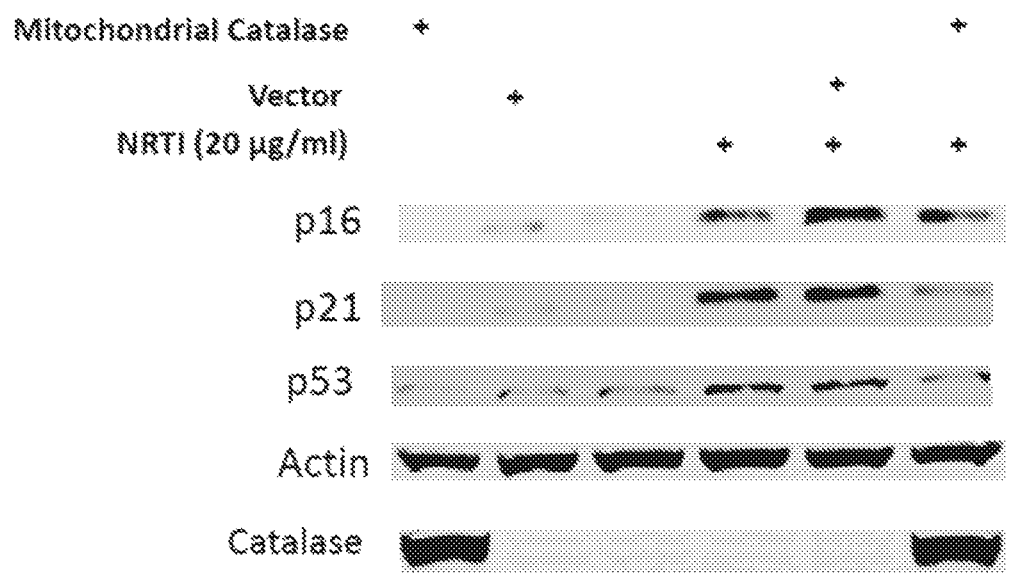
Figure 4D:
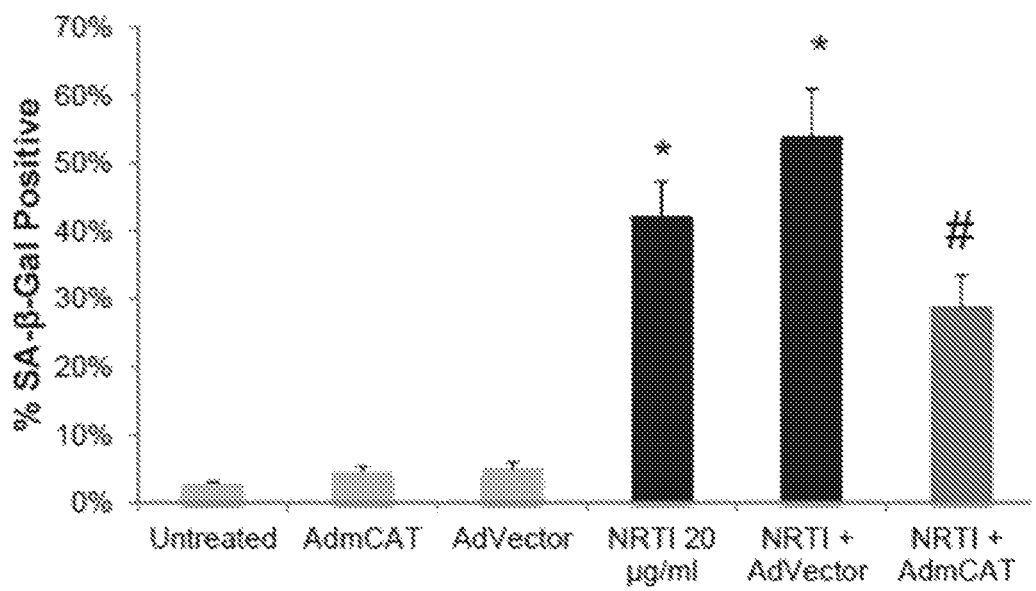
Figure 4E:
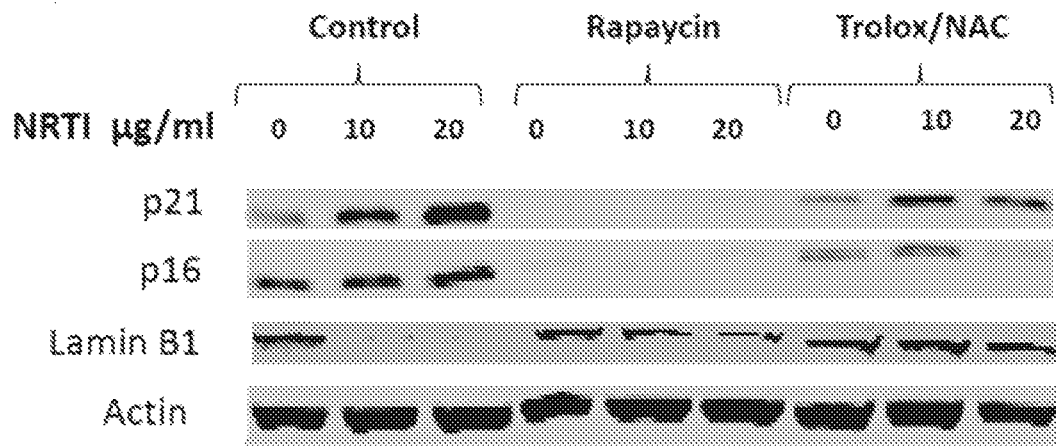

The role of mitochondrial ROS in the NRTI-induced senescence response was examined by treating control cultures (grown without rapamycin) with mito-Q, a ROS scavenger that targets mitochondrial ROS or by introducing a mitochondrial targeted catalase (mt-catalase) into cardiac fibroblasts. Mito-Q ameliorated both mitochondrial ROS production following exposure to NRTIs and the increase in senescence-associated proteins p53, p21, and p16 (FIG. 4A). In addition, the percentage of cells positive for SA-β-gal staining was reduced in cells treated with mito-Q (FIG. 4B). Similar results were obtained when cells were infected with the mt-catalase construct. The increase in senescence-associated proteins p16 and p21 following NRTI exposure was prevented and the percentage of cells staining positive for SA-β-gal was significantly reduced (FIGS. 4C-4D). The treatment of cells exposed to NRTIs with a combination of the antioxidants trolox and N-acetylcysteine (trolox/NAC) also prevented the induction of senescence. Markers of senescence were reduced including SA-β-gal expression and levels of p16 and p21, while the levels of lamin B1 were maintained, consistent with an inhibition of the senescence program (FIGS. 4E-4F).

Example 4: Activation of mTORC1/p70S6K Signaling in Senescence

Figure 5A:
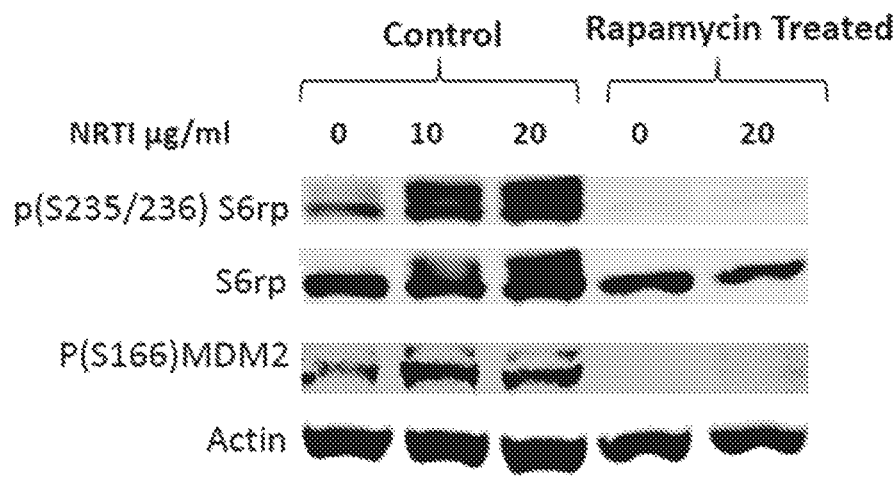
FIGS. 5A-5D illustrate phosphorylation of ribosomal S6 protein and MDM2 in response to NRTI exposure.
Figure 5B:
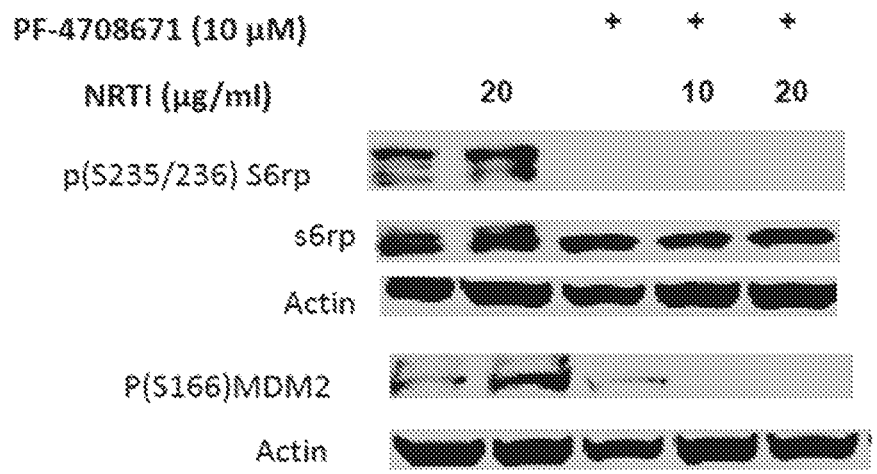

The possibility that MDM2 phosphorylation, mediated by p70S6K, is a component of the cellular response to NRTIs was investigated. It was first verified that exposure to NRTIs increased both p70S6K activity (by examining the phosphorylation status of the ribosomal S6 protein) and phosphorylation status of MDM2. Phosphorylation of both the ribosomal S6 protein and MDM2 increased in cardiac fibroblasts following exposure to NRTIs (FIG. 5A). Consistent with the inhibition of senescence, rapamycin-treated cultures showed a complete lack of ribosomal S6 phosphorylation and no increase in MDM2 phosphorylation (FIG. 5A). The role of p70S6K in MDM2 phosphorylation in this setting was examined using the specific p70S6K inhibitor PF-4708671. The phosphorylation of MDM2 in response to NRTIs was inhibited by PF-4708671, as was phosphorylation of the ribosomal S6 protein, which served as a positive control for the inhibitor (FIG. 5B).

Figure 5C:
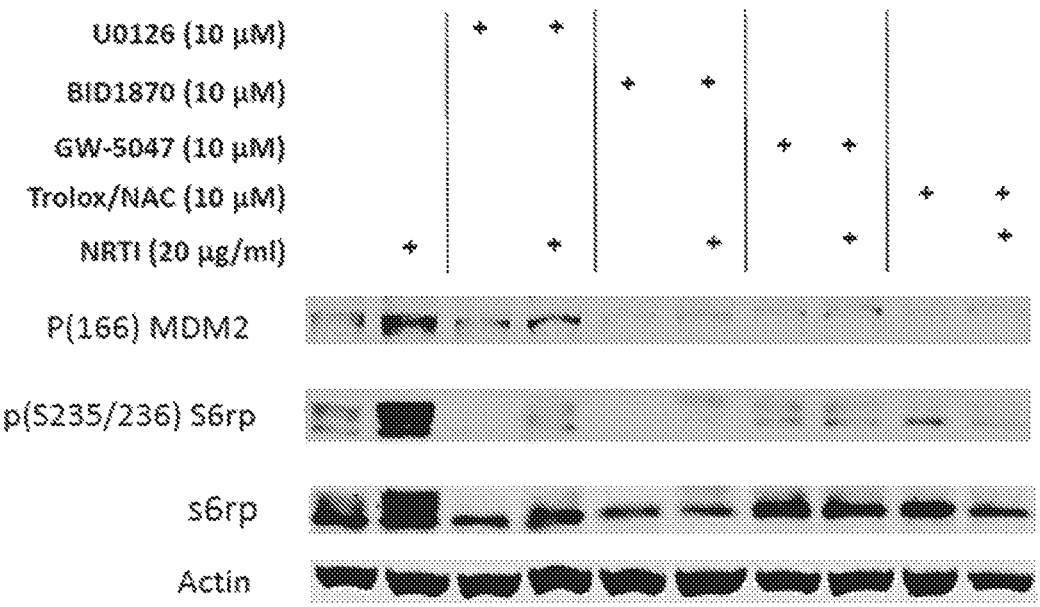
Figure 5D:
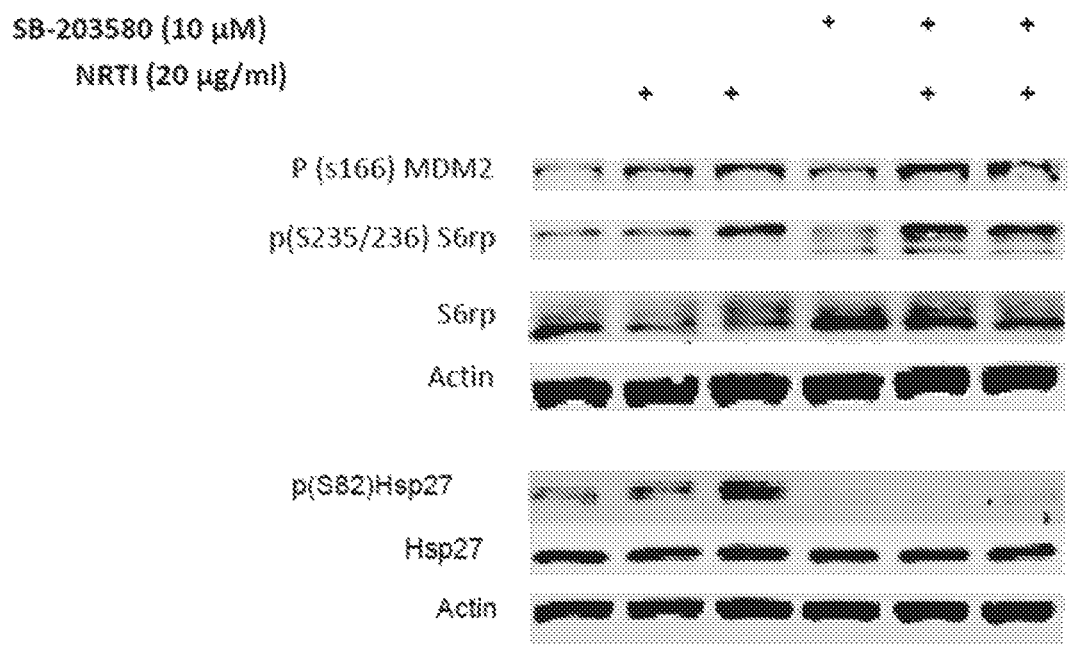

The impact of inhibitors of MAPK on ribosomal S6 and MDM2 phosphorylation in cells exposed to NRTIs was also examined. Cells exposed to NRTIs were treated with inhibitors of 3 members of the MAPK signaling pathway, MEK1 (U0126), Raf1 (GW5047), and p90RSK (BI-D1870). All 3 MAPK inhibitors caused some decrease in ribosomal S6 phosphorylation, but the p90RSK inhibitor, BI-D1870, had the greatest impact (FIG. 5C). In contrast, an inhibitor of the p38 stress activated kinase, SB-203580, had no effect on the phosphorylation of ribosomal protein S6 or MDM2 (FIG. 5D). The effects of rapamycin, the p70 S6 kinase inhibitor, the inhibitor of p90RSK, and Trolox/NAC on ribosomal S6 and MDM2 phosphorylation events in response to NRTIs were verified in human lung fibroblasts.

The dependence of NRTI-induced p70S6K activity on ROS was examined by treating cells exposed to NRTIs with trolox/N-acetylcysteine and examining ribosomal S6 phosphorylation. Both ribosomal S6 phosphorylation and MDM2 phosphorylation were decreased when cells exposed to NRTIs were treated with trolox/N-acetylcysteine (FIG. 5C). Involvement of the NADPH oxidase system was examined using apocyanin, an inhibitor of NADPH oxidases. However, treatment of NRTI-exposed cells with apocyanin did not prevent the increase in ribosomal S6 phosphorylation. Similar results in terms of p7-S6 kinase and MDM phosphorylation were obtained when human lung fibroblasts were exposed to NRTIs.

Figure 6A:
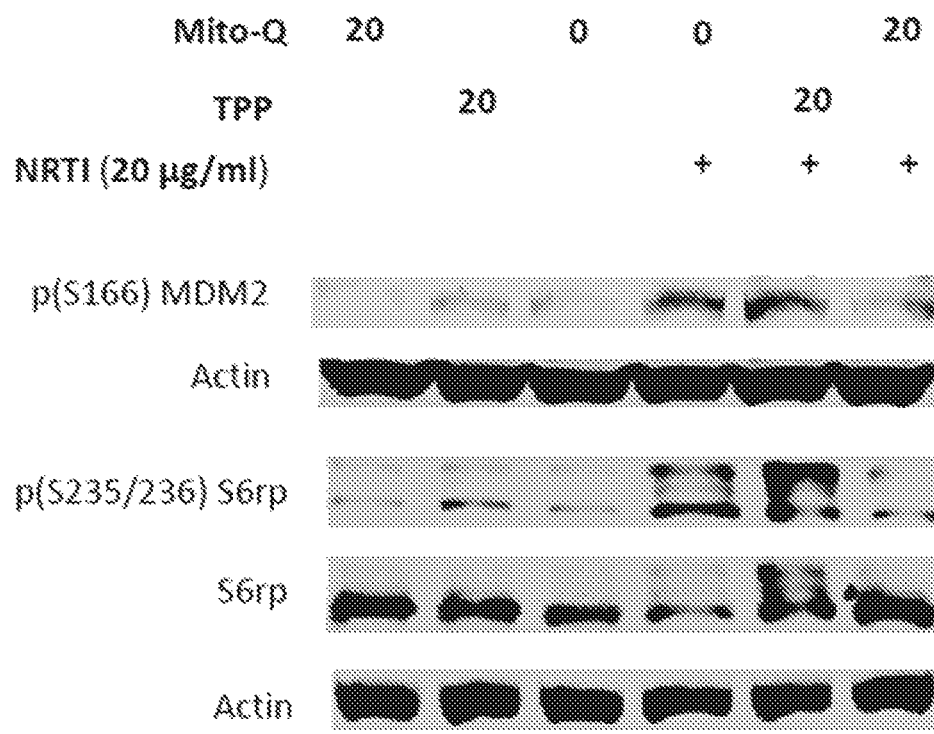
FIGS. 6A-6G illustrate effect of Mito-Q and mt-catalase on ribosomal S6 and MDM2 phosphorylation and mitochondrial activity in response to NRTIs.
Figure 6B:
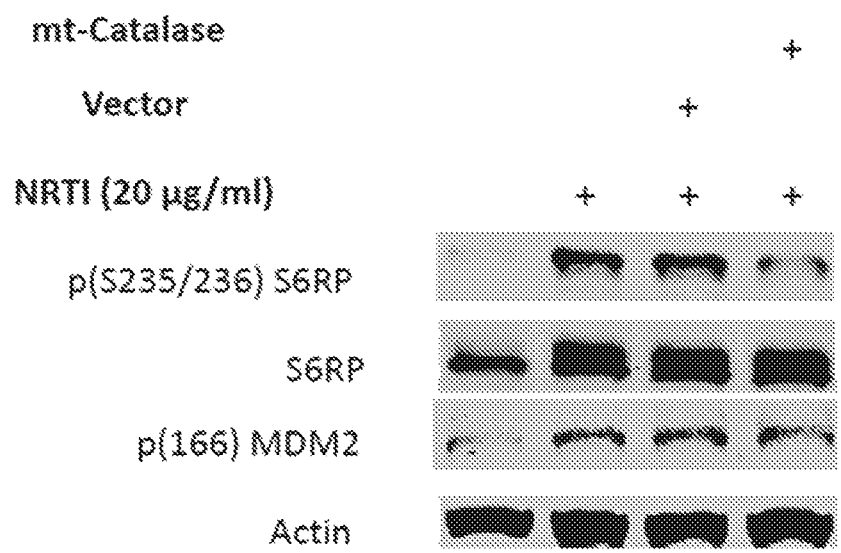
Figure 6C:
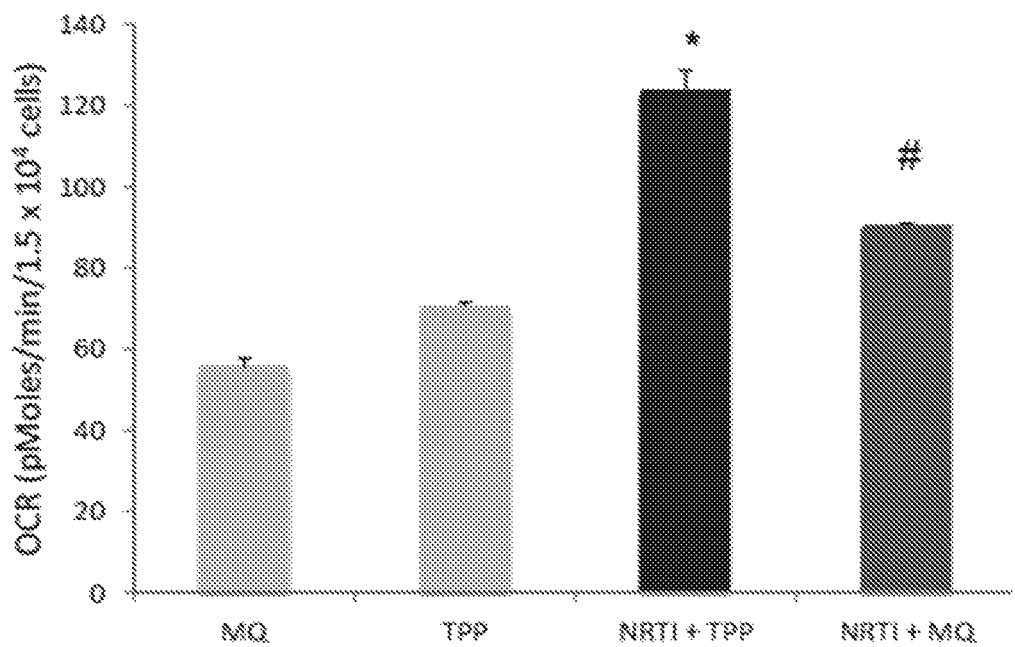
Figure 6D:
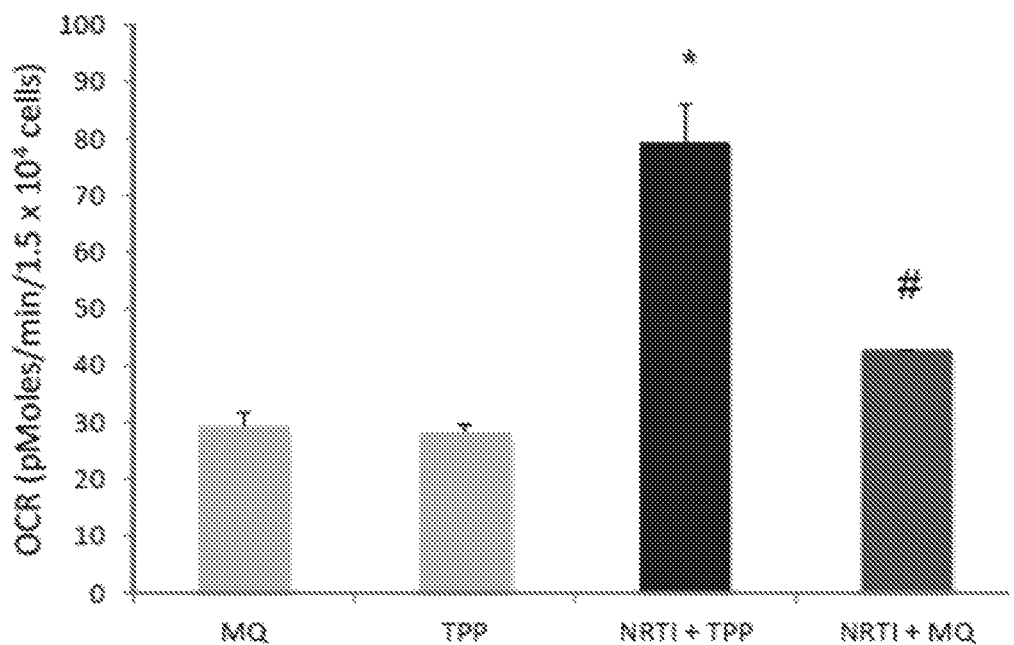
Figure 6E:
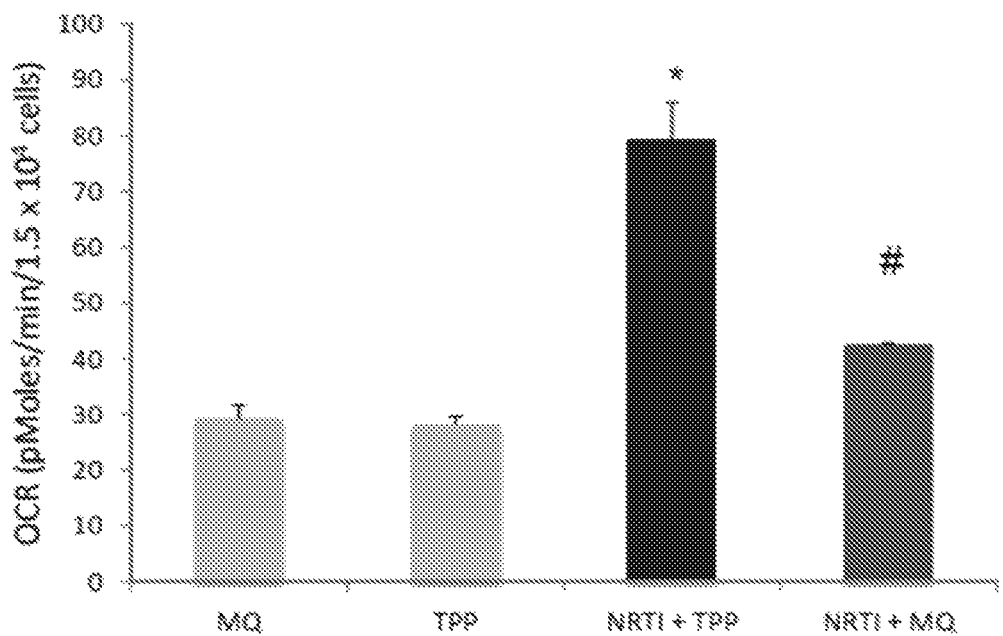
Figure 6F:
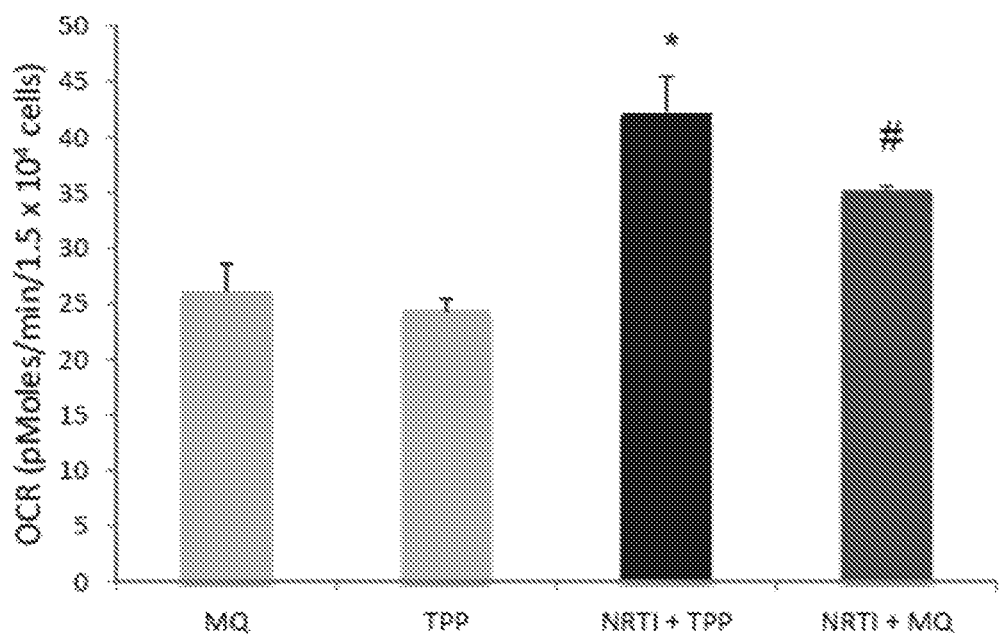
Figure 6G:
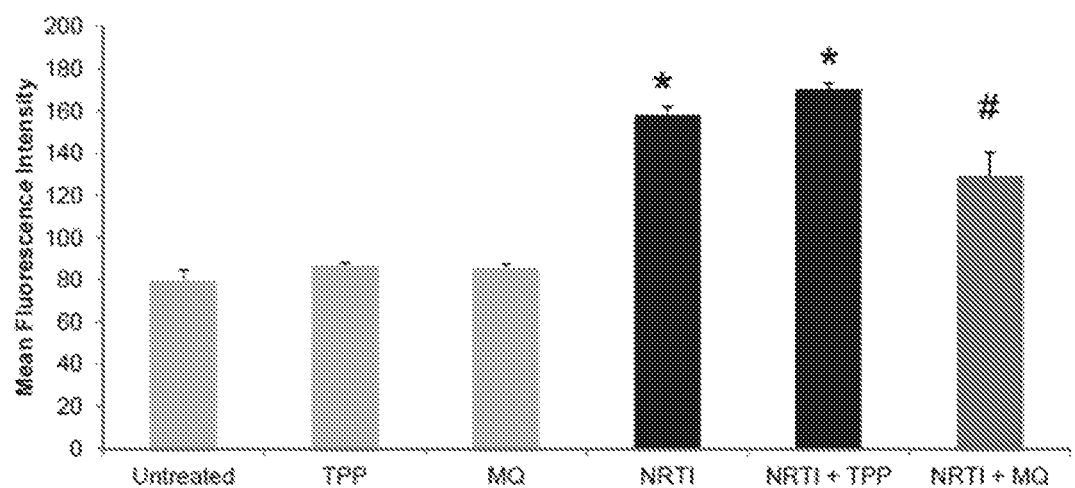

In order to examine the potential role of mitochondrial ROS in the activation of mTOR activity, cells were treated with either mito-Q during NRTI exposure or the mt-catalase adenovirus prior to exposure to NRTIs. Both of these interventions, mito-Q and expression of the mt-catalase, reduced ribosomal S6 phosphorylation and MDM2 phosphorylation following exposure to NRTIs (FIGS. 6A-6B). Additionally, mito-Q treated cells were examined by Seahorse Bioanalyzer to assess mitochondrial activity. This analysis revealed that mito-Q treatment partially alleviated the increase in basal respiration, ATP-linked respiration, and proton leak, while maximal respiration was less affected (FIGS. 6C-6F). In addition, mito-Q treated cells exhibited a lower level of mitochondrial ROS when exposed to NRTIs (FIG. 6G).

Figure 7A:
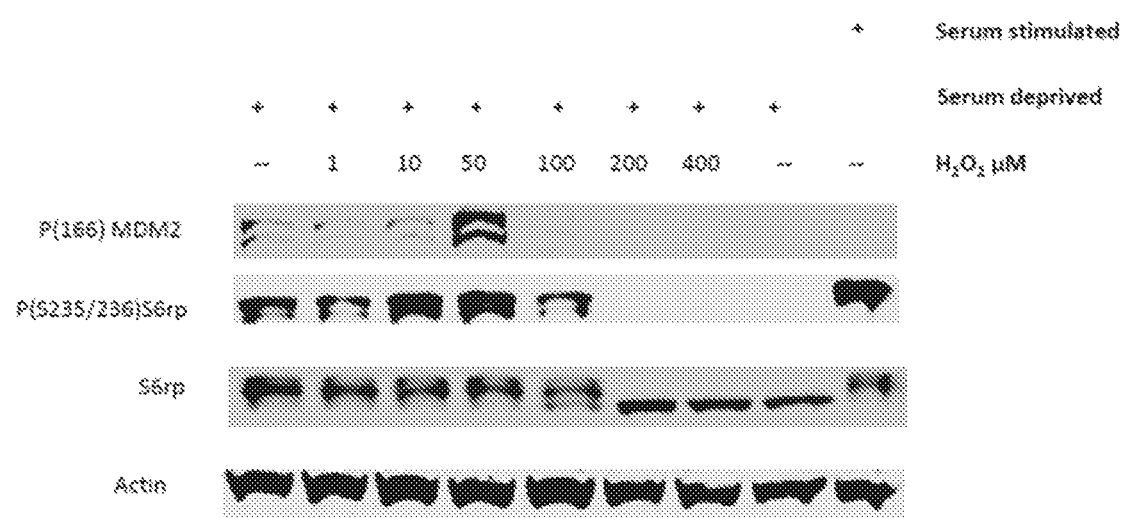
FIGS. 7A-7B illustrate phosphorylation status of the ribosomal S6 protein and MDM2 in response to oxidative stress.
Figure 7B:
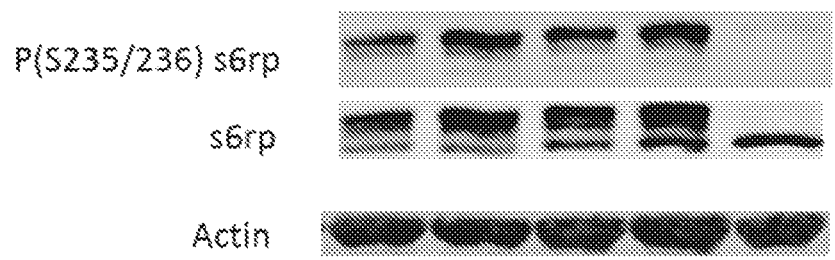

To determine whether increased ROS can directly induce phosphorylation of the ribosomal S6 protein, cardiac fibroblasts were placed in serum-free medium for 48 hours to abrogate growth factor signaling that might influence mTORC1 activity. The cells were then exposed to hydrogen peroxide at concentrations ranging from 1 to 400 µM for 2 hours. Both ribosomal S6 phosphorylation and MDM2 phosphorylation were increased at the lower concentrations of hydrogen peroxide, with maximal activation at 50 µM and inhibition of both ribosomal S6 phosphorylation and MDM2 phosphorylation occurred at concentrations above 100 µM (FIG. 7A). The response to hydrogen peroxide differed from the serum response which, consistent with a proliferative response, led to phosphorylation of the ribosomal S6 protein, but not MDM2 (FIG. 7A, far right). To determine whether an induction of mitochondrial ROS can lead to activation of mTOR signaling, cell were exposed to a range of concentrations of rotenone and the phosphorylation of the ribosomal S6 protein was examined. Exposure of cells to nanomolar concentrations of rotenone lead to increased S6 phosphorylation with a sharp inhibition of S6 phosphorylation occurring at 50 nM (FIG. 7B).

Figure 8A:
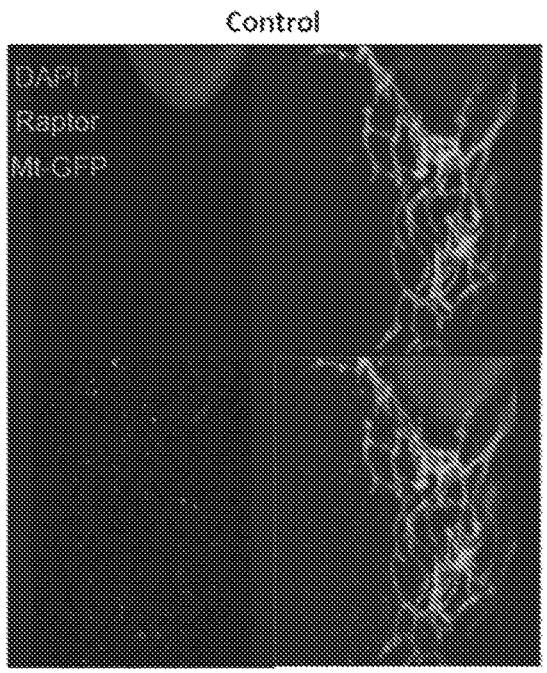
FIGS. 8A-8C illustrates localization of Raptor to mitochondria in the presence of NRTIs.
Figure 8B:
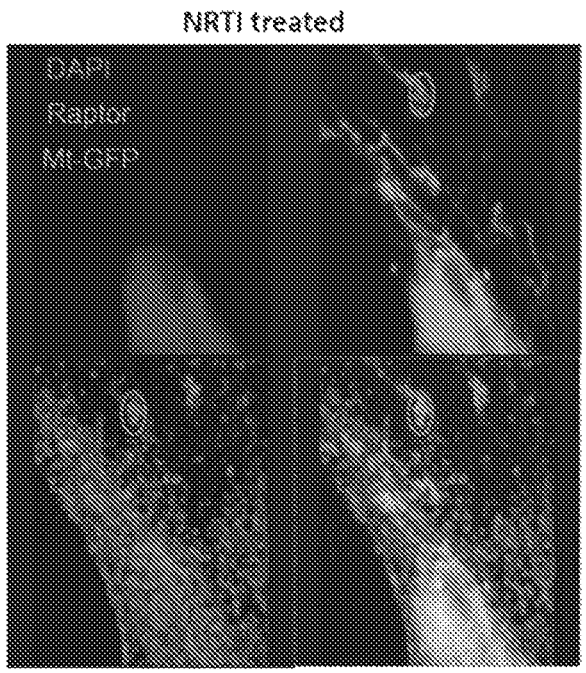
Figure 8C:
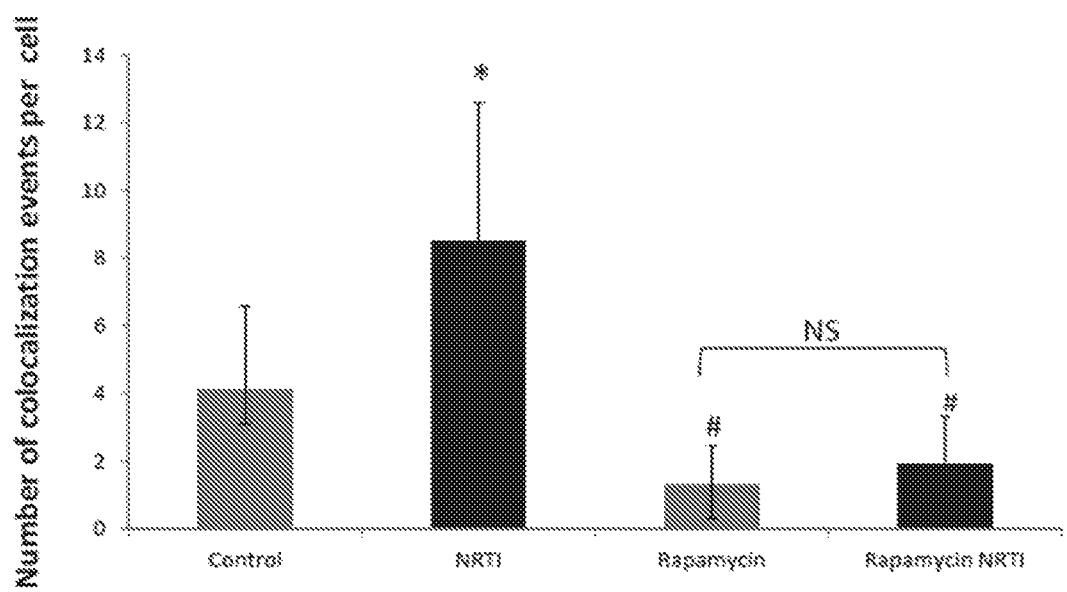

Example 5: Association of mTORC1 with Mitochondria in Response to Mitochondrial Stress The possibility that mitochondrial association with the mTORC1 complex is enhanced when cells are exposed to NRTIs was examined using human cardiac fibroblasts expressing a green fluorescent protein fused to a mitochondrial-targeting sequence (mt-GFP). These cells were exposed to NRTIs and fixed for immunofluorescence using antibodies that recognize the mTORC1-specific component. Raptor. In cells exposed to NRTIs, Raptor was associated with mitochondria to a greater degree than in untreated cells (FIGS. 8A-8C).

Figure 9A:
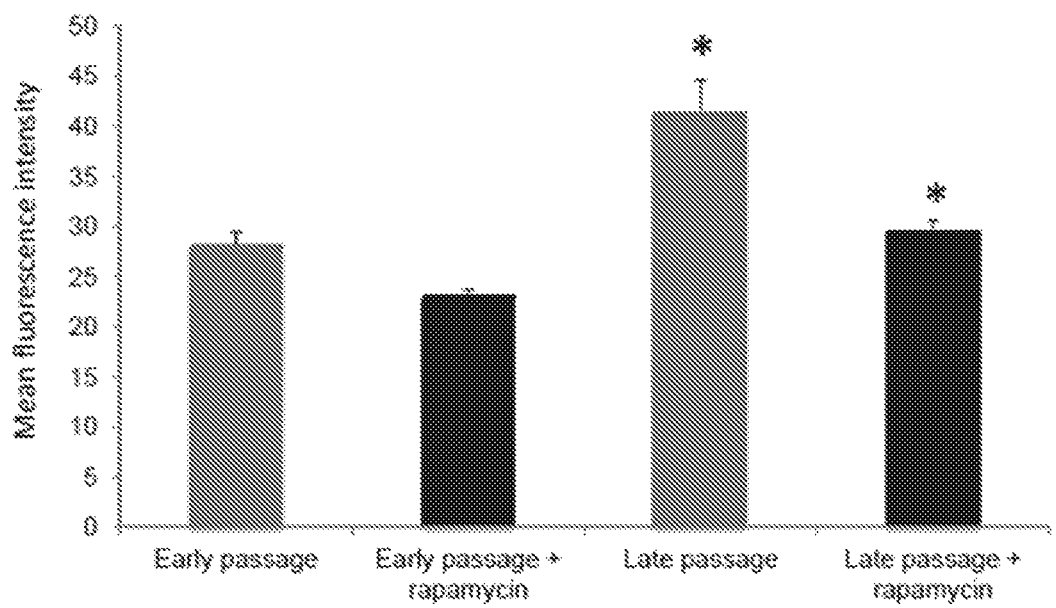
FIGS. 9A-9I illustrates the finding that fibroblasts display senescence elevated mitochondrial ROS and enhanced phosphorylation of ribosomal S6 protein and MDM2.
Figure 9B:
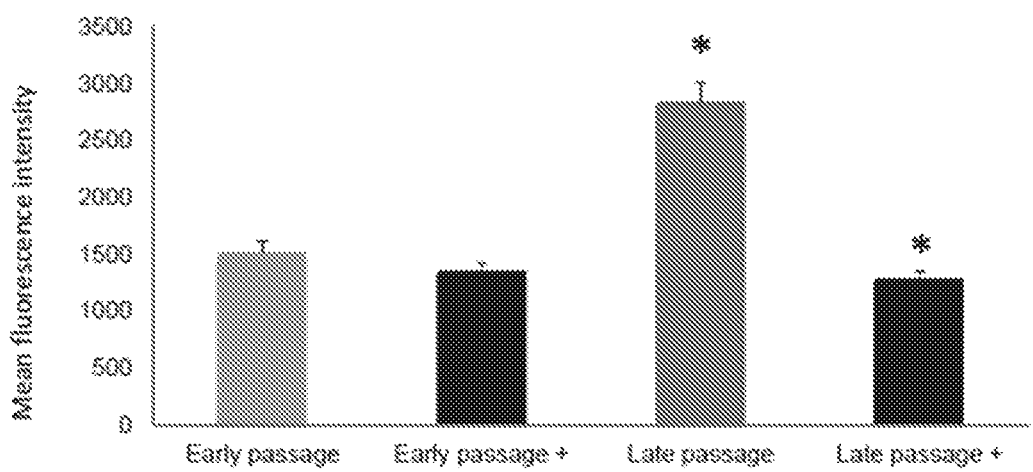
Figure 9C:
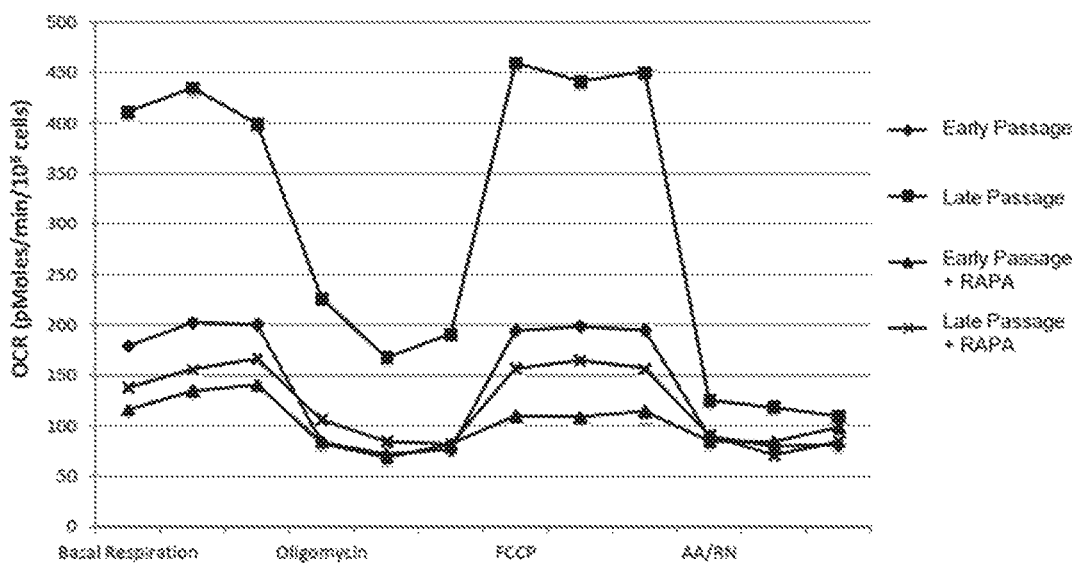
Figure 9D:
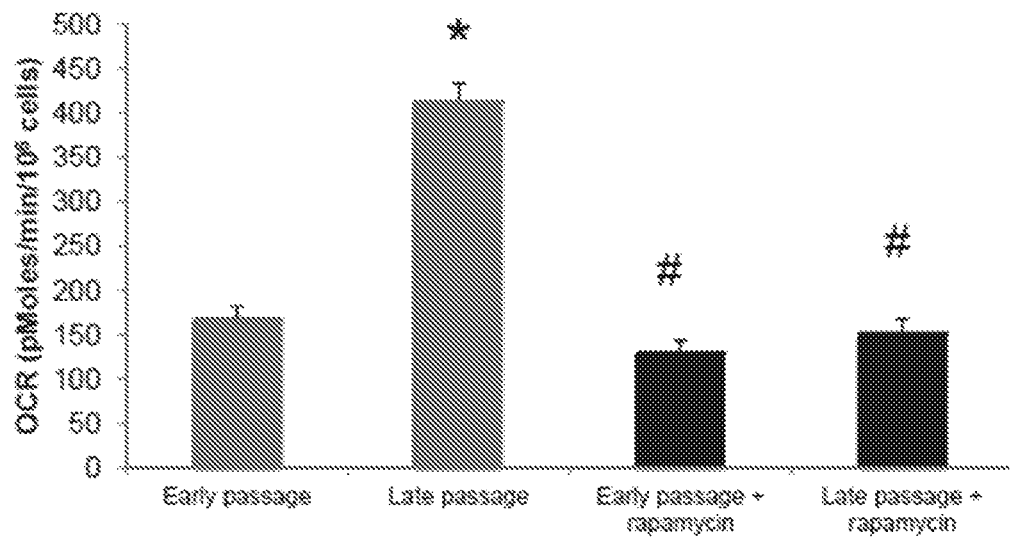
Figure 9E:
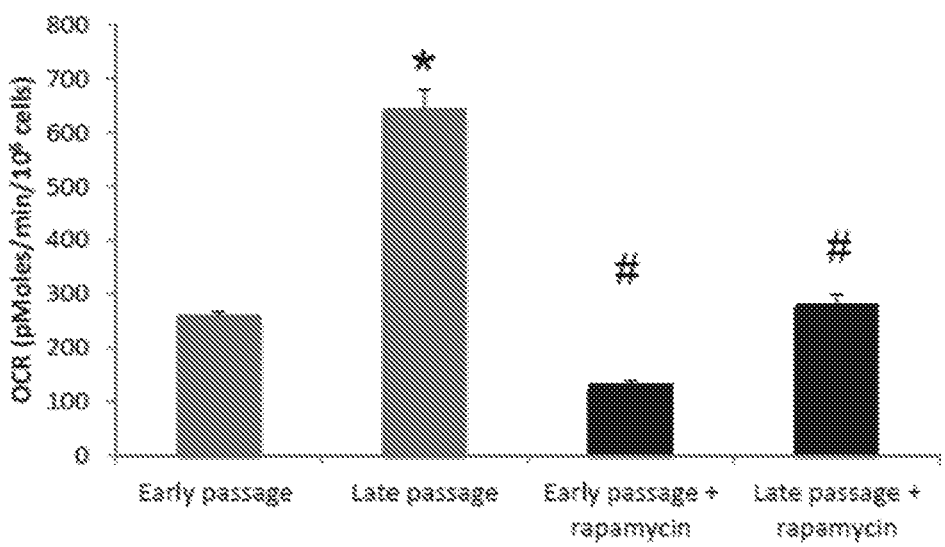
Figure 9F:
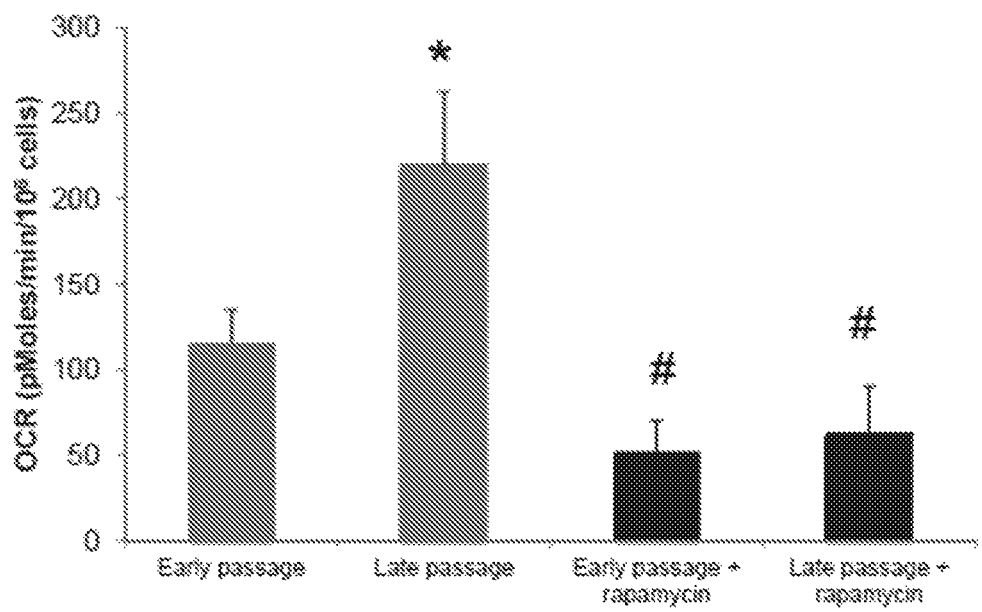
Figure 9G:
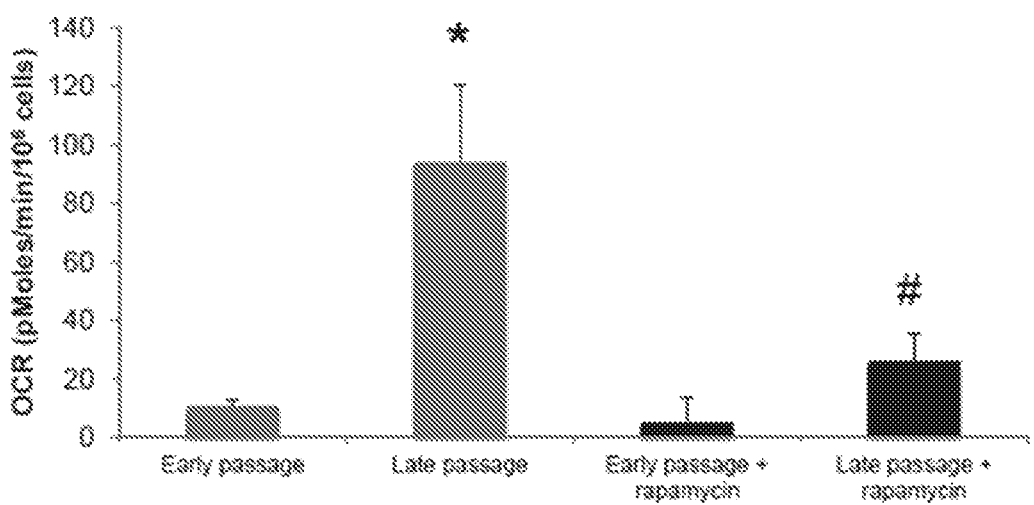

The role of mitochondrial ROS in senescence was examined by treating senescent cardiac fibroblasts with the mitochondrial ROS scavenger mito-Q or by introducing a mitochondrial targeted catalase. Initially, levels of mitochondrial and total cellular ROS were examined in late passage cells. This assessment revealed elevated levels of mitochondrial ROS and total cellular ROS in late passage cells (FIGS. 9A-9B). Assessment of mitochondrial activity by Seahorse Bioanalyzer revealed elevated respiration, consistent with previous studies in senescent cells using isolated mitochondria. Bioanalyzer analysis indicated that both basal and ATP-linked respiration rates were significantly increased in senescent cells compared to early passage cells, as was proton leak (FIGS. 9C-9G).

Figure 9H:
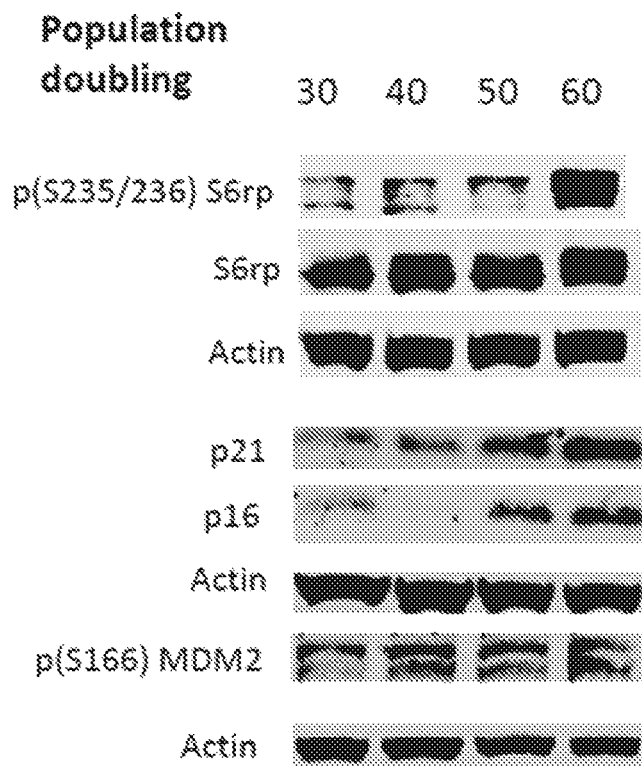
Figure 9I:
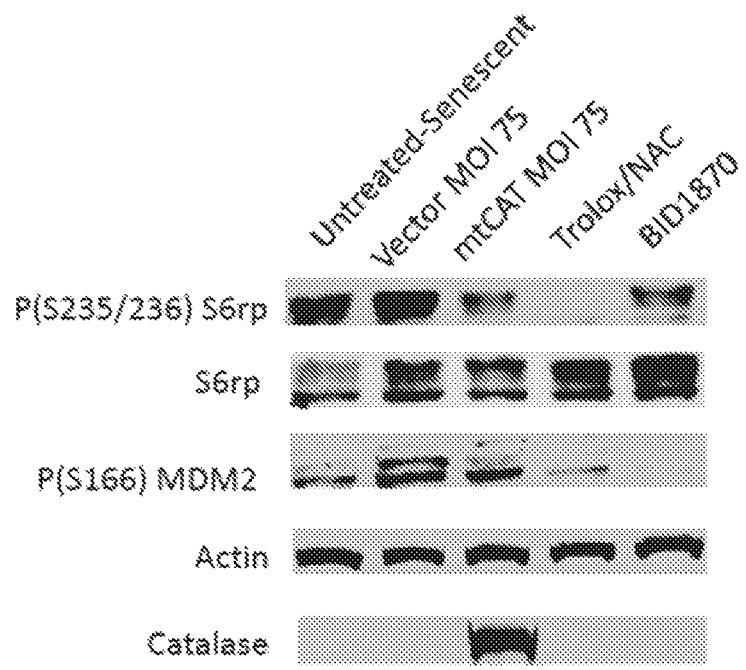
Figure 11A:
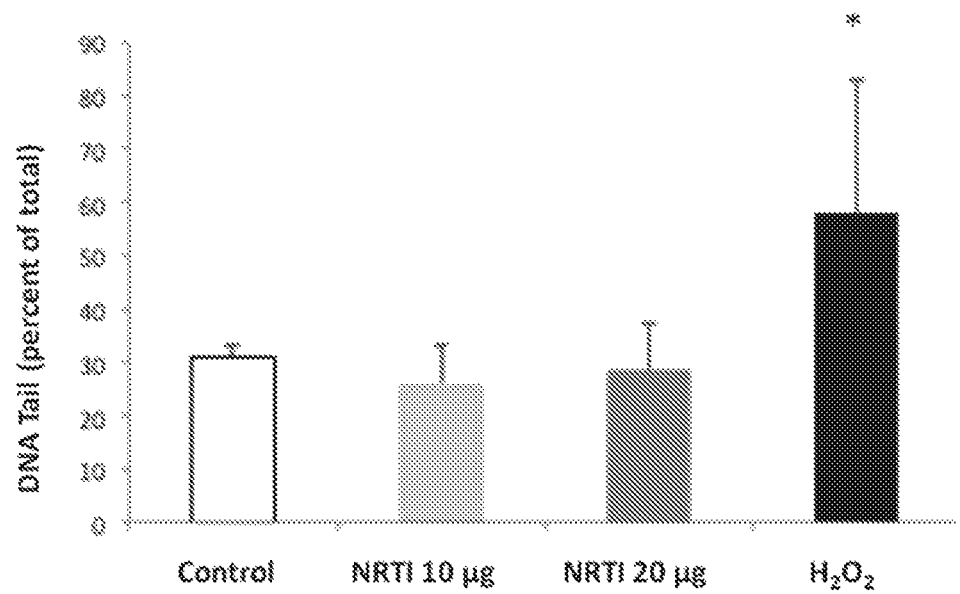
FIGS. 11A-11F illustrate status of p53 in human cardiac fibroblast cultures exposed to NRTIs and in rapamycin-treated cultures.
Figure 11B:
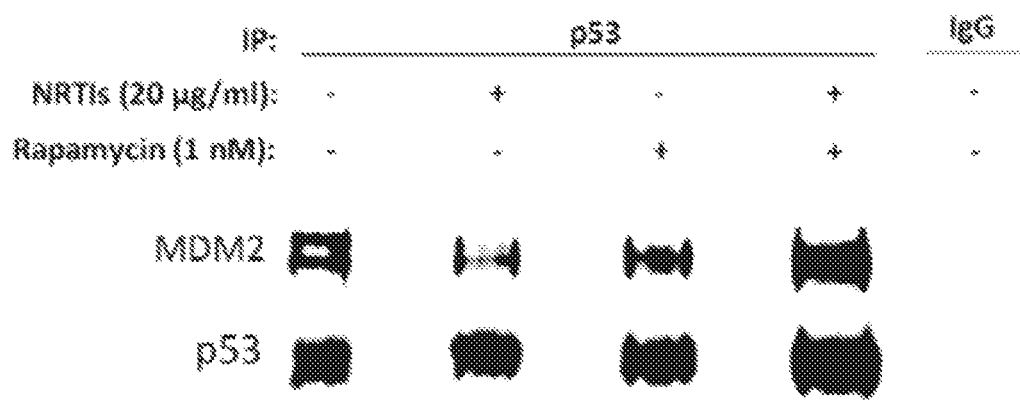
Figure 11C:
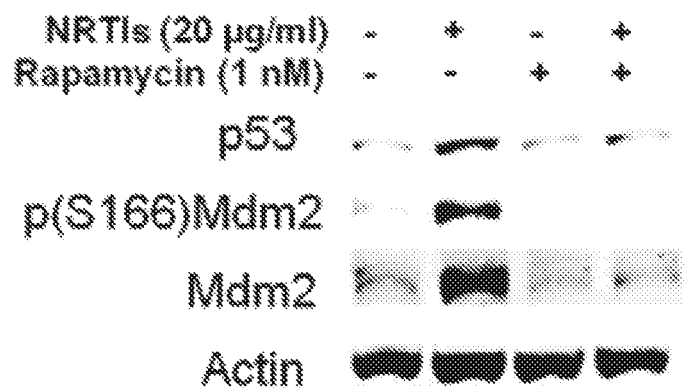
Figure 11D:
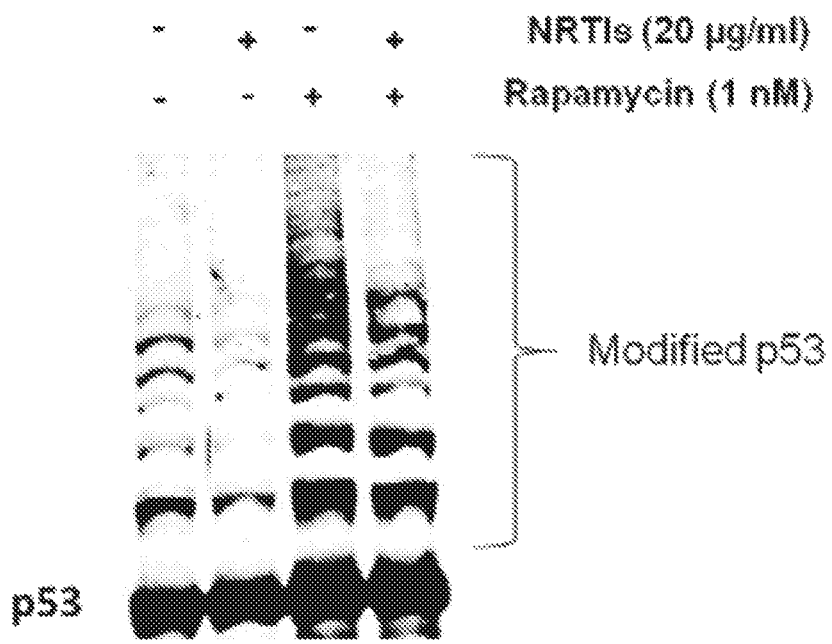
Figure 11E:
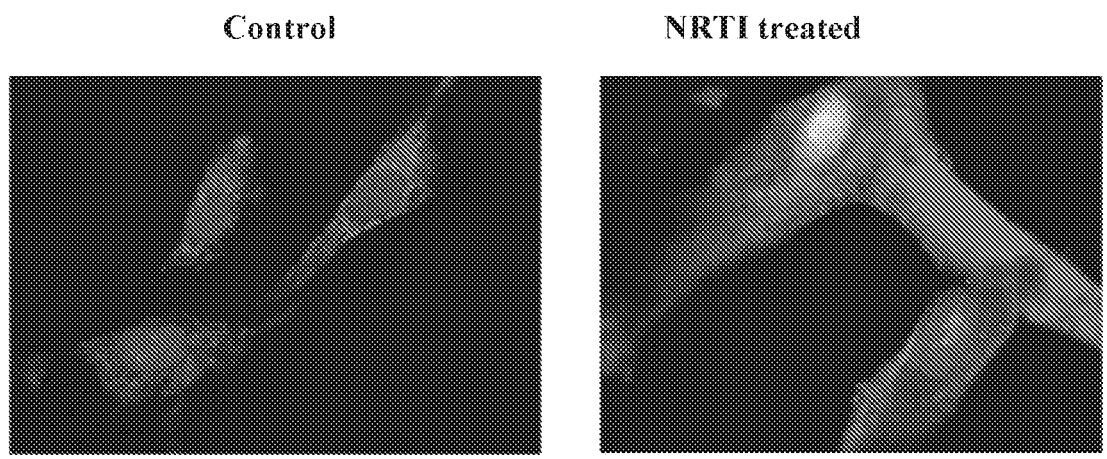
Figure 11F:
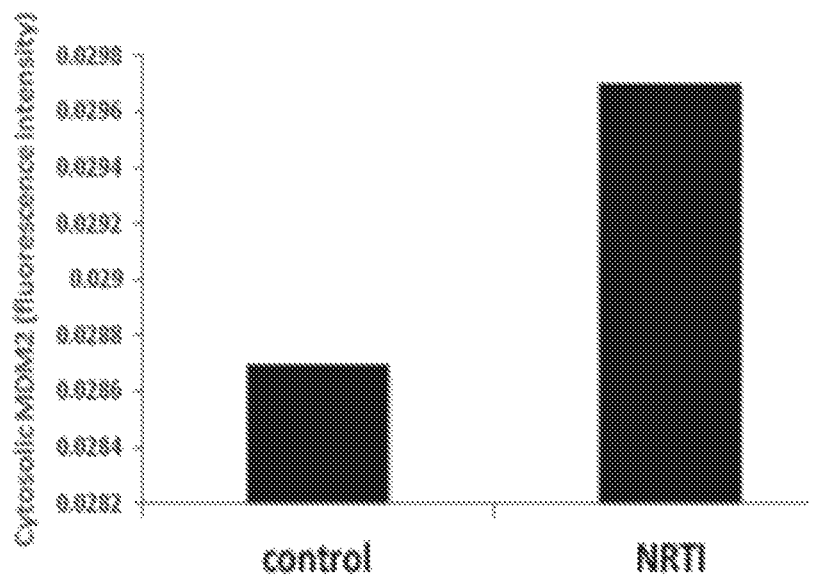
Figure 12A:
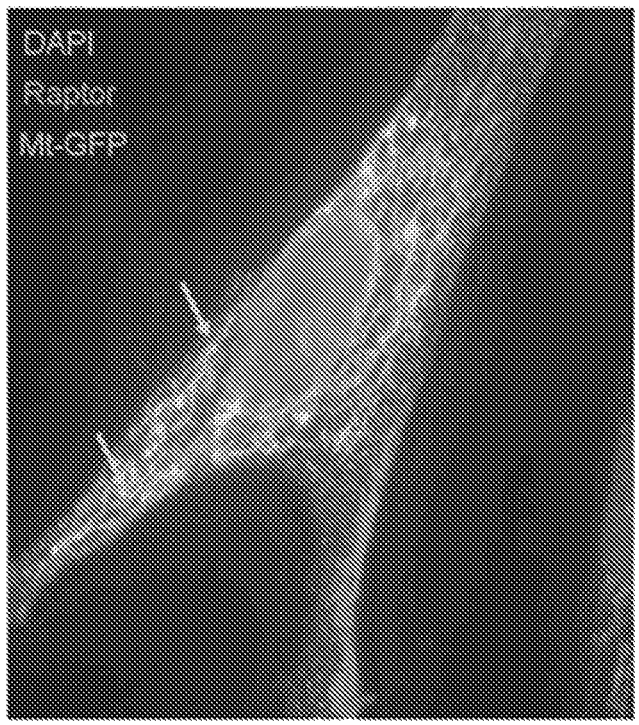
FIGS. 12A-12D are a set of images illustrating mitochondrial association of Raptor.
Figure 12B:
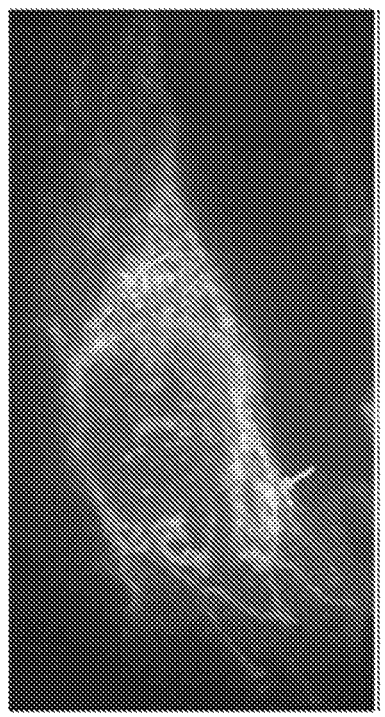
Figure 12C:
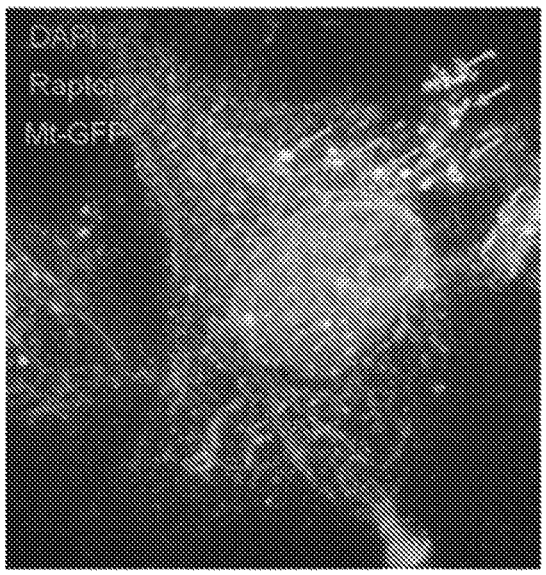
Figure 12D:
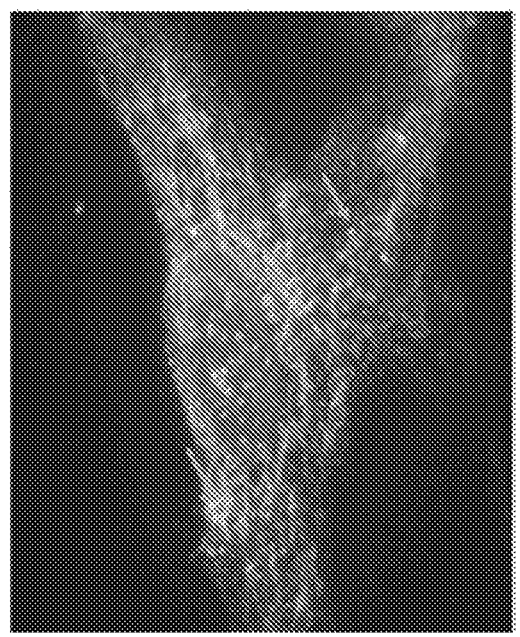
Figure 13:
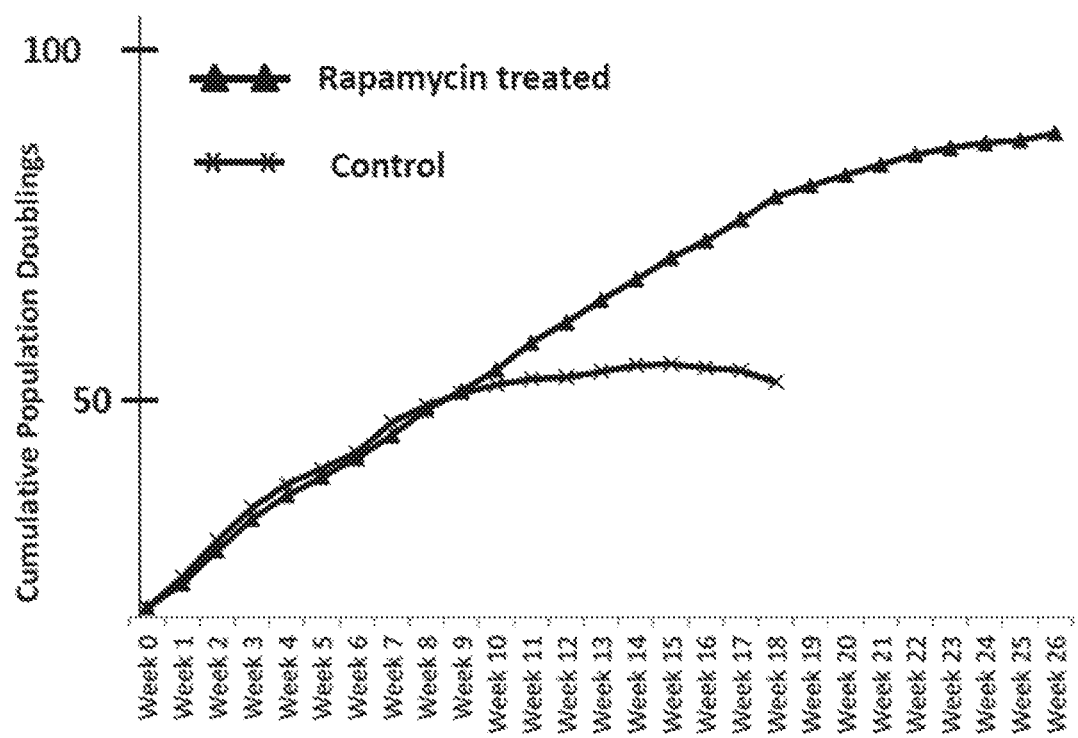
FIG. 13 is a graph illustrating the finding that rapamycin treatment provides lifespan extension in human fibroblasts. Human fibroblast cells were growth in culture medium with or without rapamycin (1 nM). Cultures were split every 7 days and reseeded at identical cell number/cm$^2$ each week. The lifespan of normal human fibroblasts is counted by the number of times that the cells double. Rapamycin treated grow well beyond the normal lifespan for these cells.
Figure 14:
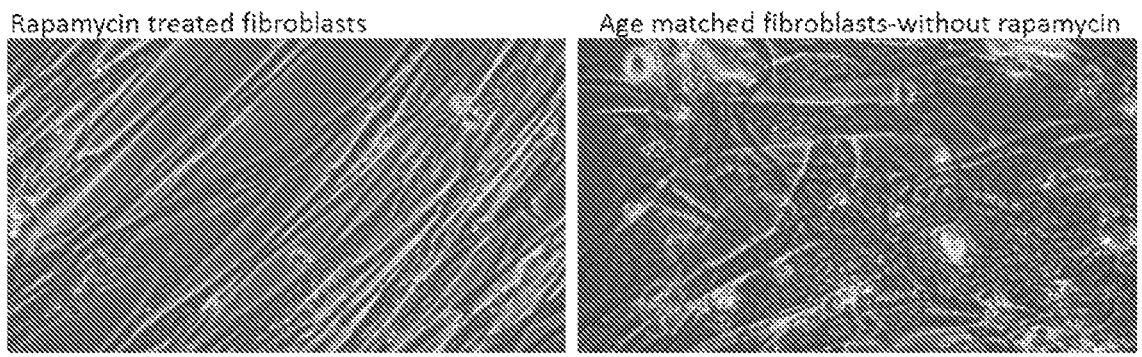
FIG. 14 illustrates the finding that rapamycin preserves cell organization during aging of human fibroblasts. Human fibroblasts maintained in the presence of low doses of rapamycin maintained an orderly growth pattern while untreated fibroblasts lost their ability to properly orient themselves with age. The ability to organize is a critical element of normal fibroblast function and contributes to tissue integrity in normal tissue. The disorganization which occurs with age contributes to functional decline.
Figure 15:
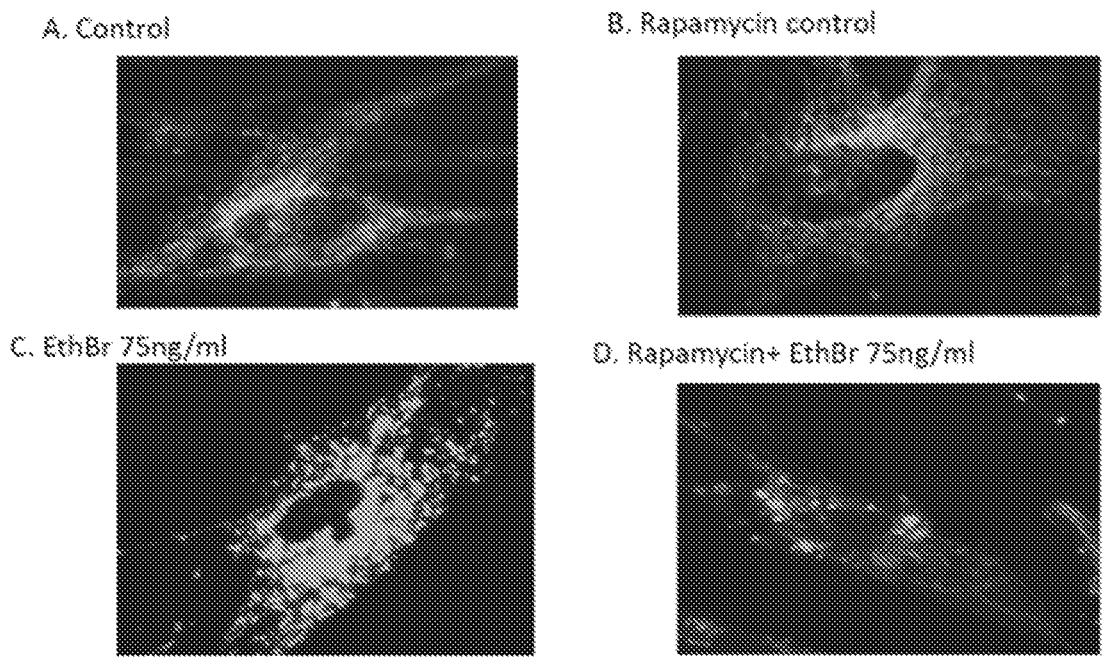
FIG. 15 are a set of images illustrating the finding that rapamycin preserves mitochondrial network in the face of damage. Panel A depicts that human fibroblasts expressing a fluorescent protein in the mitochondrial display a green mitochondrial network. Panel B depicts that rapamycin treated cells have a normal mitochondrial network. Panel C depicts that the mitochondrial network is destroyed by exposure to a mitochondrial toxin, ethidium bromide (EthBr). Panel D depicts that rapamycin treated cells are able to maintain their mitochondrial network following exposure to EthBr.
Figure 16:
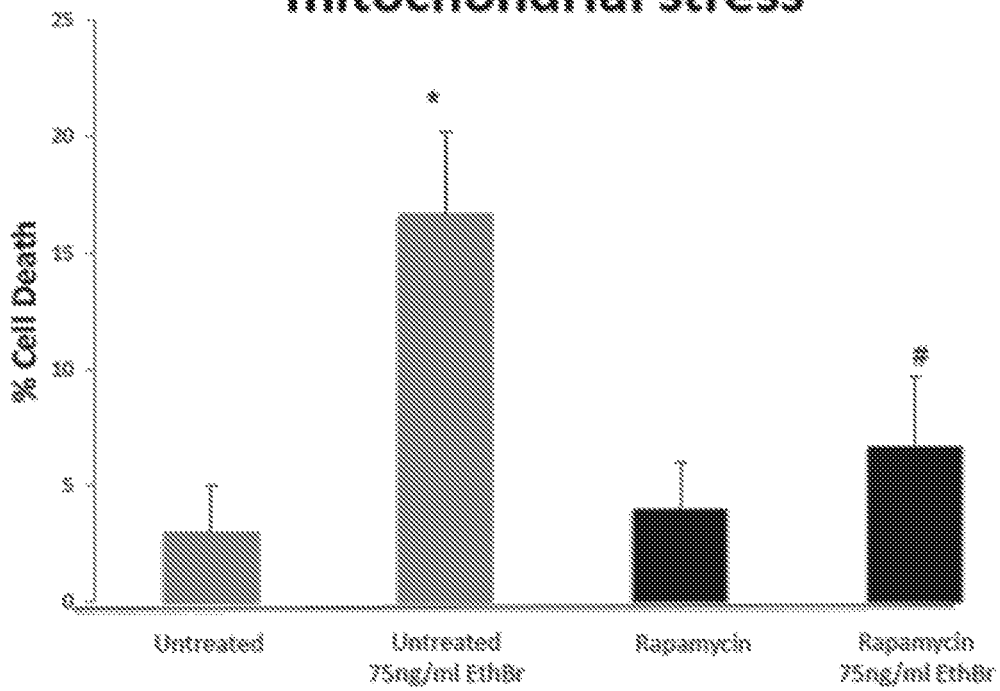
FIG. 16 is a bar graph illustrating the finding that rapamycin increases the survival of human fibroblasts following mitochondrial stress. Human fibroblasts were exposed to ethidium bromide for 7 days and cell viability measured at that time.
Figure 17:
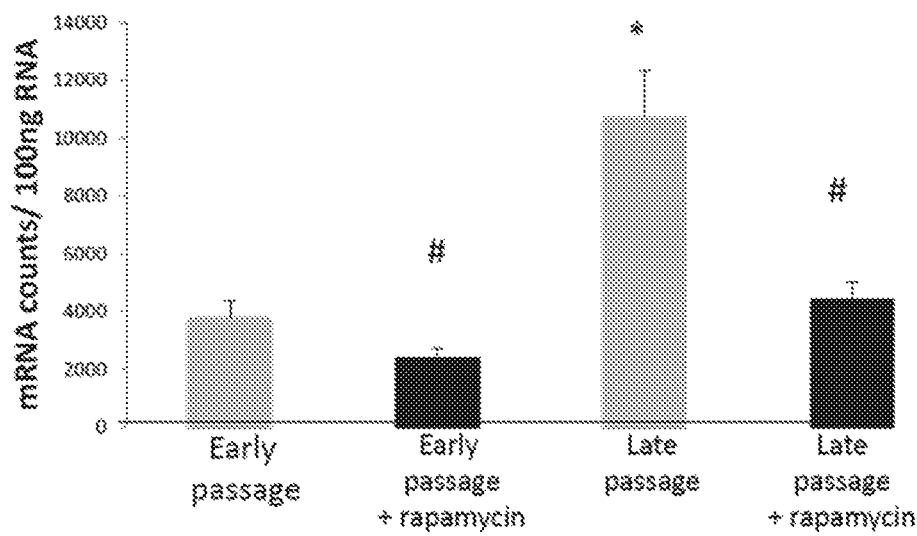
FIG. 17 is a bar graph illustrating the finding that rapamycin prevents the expression of genes that cause senescence. The p21 gene makes a protein that is critical for senescence of human fibroblasts. Cells grown in the presence of rapamycin do not produce p21 as they age while the control cells express p21 and enter senescence.
Figure 18:
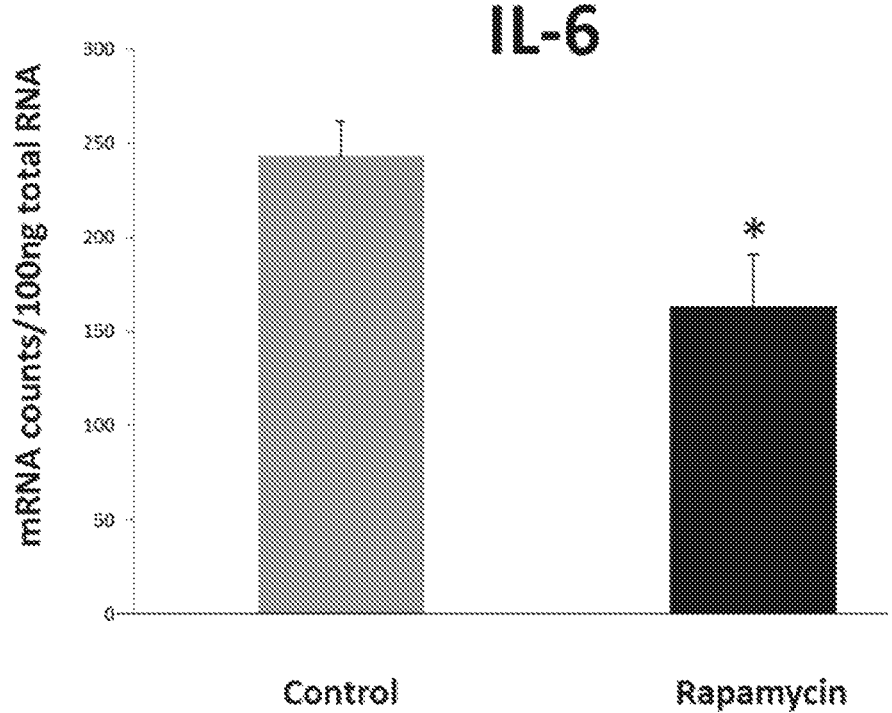
FIG. 18 is a bar graph illustrating the finding that rapamycin prevents the expression of genes related to inflammation. The IL-6 gene makes a protein that activates the immune system to recruit immune cells into an area of tissue damage. Cells grown in the presence of rapamycin do not produce IL-6 as they age while the control cells express IL-6 and enter senescence.
Figure 19:
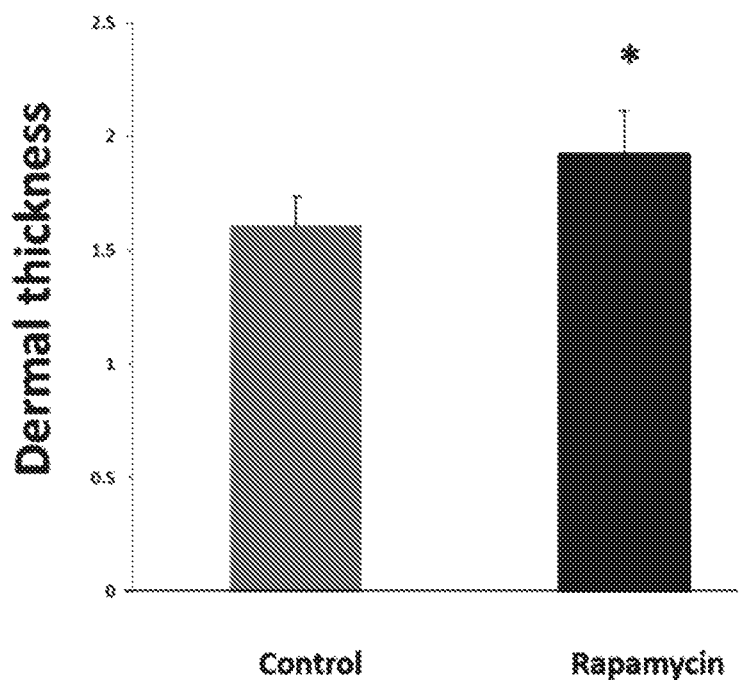
FIG. 19 is a bar graph illustrating the finding that rapamycin increases dermal thickness in atrophic skin. Dermal thickness was measured using a Mitoutoyo digital caliper with certified accuracy to 0.001 mm following 14 days of rapamycin treatment in an emulsified gel preparation.
Figure 20:
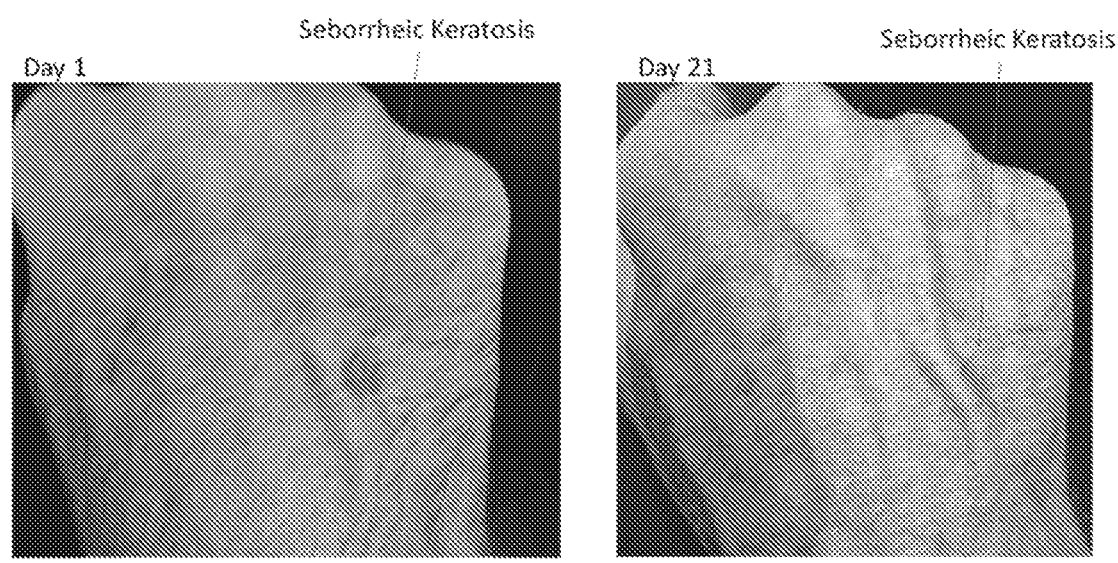
FIG. 20 is a photograph of a seborrheic keratosis lesion before and after 21 days of treatment with 10 µM rapamycin in an emulsified gel preparation as in FIG. 19. A significant reduction in severity of the lesion was apparent upon visual inspection.

The progressive increase in ribosomal S6 and MDM2 phosphorylation during replicative senescence was verified in cardiac fibroblasts (FIG. 9H). In order to test the dependence of phosphorylation of the ribosomal S6 protein in senescent cells on ROS, senescent cells were treated with the ROS scavengers trolox and N-acetylcysteine. In parallel, the mt-catalase was introduced into senescent cells to reduce mitochondrial ROS production. Both of these interventions reduced the high basal levels of ribosomal S6 phosphorylation typical of senescent fibroblasts and reduced levels of phosphorylated MDM2. In addition, treatment with the p90RSK inhibitor, BI-D1870, also reduced both ribosomal S6 and MDM2 phosphorylation in senescent cells (FIG. 9I).

Example 6: In Vivo Topical Application of Rapamycin

A single site open label study was performed. A patient presenting with an area of dermal atrophy and actinic keratosis on the hand was evaluated for application of Formulation R, the contralateral hand with similar dermal thickness but no actinic keratosis was used as a control. The patient was provided with Formulation R with instructions for twice daily application.

Following a 2-week (14 day) period, both actinic keratosis and dermal thickening showed signs of improvement as self-reported by the patient and found by study personnel. Evaluation of dermal thickness revealed an increase in dermal thickness of ~20% (1.6 SD 0.13 untreated versus 1.9 SD 0.19 treated). Actinic keratosis was improved from a rating of 3 to a rating of 2. No evidence of adverse reaction was observed or reported by the patient at 14 day follow-up visit. Continued application of Formulation R beyond the initial 14 day period provided continued benefit while administration of the carrier formulation without rapamycin has no influence on dermal thickness in the contralateral hand.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating an age-related dermal disorder in a mammalian subject, the method comprising topically administering to the subject a composition consisting essentially of about 0.001-0.01% (w/w) of a mTORC1 inhibitor wherein the mTORC1 inhibitor is rapamycin, or a salt, solvate, enantiomer, or diastereoisomer thereof, wherein the proliferative potential of dermal cells is maintained; and wherein the age-related dermal disorder is at least one selected from the group consisting of age-related dermal atrophy, seborrheic or actinic keratosis, pseudoscars, lentigines, focal areas of dermal thickening, and coarse wrinkles.

2. The method of claim 1, wherein the subject is a human.

3. The method of claim 1, wherein the composition further comprises a dermatologically acceptable carrier.

4. The method of claim 3, wherein the dermatologically acceptable carrier is at least one selected from the group consisting of a solvent, lubricant, emollient, emulsifier, moisturizer, thickening wax, softener, fragrance, preservative, and artificial color.

5. The method of claim 3, wherein the dermatologically acceptable carrier comprises petrolatum.

* * * * *